US005965544A

United States Patent [19]
Renkonen et al.

[11] Patent Number: 5,965,544
[45] Date of Patent: Oct. 12, 1999

[54] SYNTHETIC MULTIVALENT SLE$^X$ CONTAINING POLYLACTOSAMINES AND METHODS FOR USE

[75] Inventors: Ossi Renkonen; Risto Renkonen, both of Espoo, Finland

[73] Assignee: Glycim Oy, Espoo, Finland

[21] Appl. No.: 08/722,573

[22] Filed: Sep. 27, 1996

Related U.S. Application Data

[60] Provisional application No. 60/007,867, Dec. 1, 1995, and provisional application No. 60/004,623, Sep. 29, 1995.

[51] Int. Cl.$^6$ .................................................. A61K 31/715
[52] U.S. Cl. .......................... 514/54; 536/17.2; 536/18.7; 514/25
[58] Field of Search .................................. 536/17.2, 18.7; 514/25, 54

[56] References Cited

U.S. PATENT DOCUMENTS

| | | | |
|---|---|---|---|
| 5,352,670 | 10/1994 | Venot et al. | 514/54 |
| 5,374,541 | 12/1994 | Wong et al. | 435/74 |
| 5,409,817 | 4/1995 | Ito et al. | 435/74 |
| 5,426,178 | 6/1995 | Laine et al. | 536/1.11 |
| 5,559,103 | 9/1996 | Gaeta et al. | 514/56 |

FOREIGN PATENT DOCUMENTS

| | | |
|---|---|---|
| 0 319 253 | 6/1989 | European Pat. Off. . |
| 0 577 580 | 1/1994 | European Pat. Off. . |
| 0 627 442 | 12/1994 | European Pat. Off. . |
| WO 91/19501 | 12/1991 | WIPO . |
| WO 91/19502 | 12/1991 | WIPO . |
| WO 92/02527 | 2/1992 | WIPO . |
| WO 92/22565 | 12/1992 | WIPO . |
| WO 94/26760 | 11/1994 | WIPO . |
| WO 95/01361 | 1/1995 | WIPO . |
| WO 95/03059 | 2/1995 | WIPO . |
| WO 95/06057 | 3/1995 | WIPO . |
| WO 95/29681 | 11/1995 | WIPO . |

OTHER PUBLICATIONS

MAemura et al. J. Biol. Chem. Dec. 1992, 267(34), 24379–24386.

Arbonés, M. L. et al., "Lymphocyte Homing and Leukocyte Rolling and Migration Are Impaired in L–Selectin–Deficient Mice," *Immunity* 1(4):247–260 (Jul. 1994).

Baumhueter, S. et al., "Binding of L–Selectin to the Vascular Sialomucin CD34," *Science* 262:436–438 (Oct. 1993).

Bertozzi, C. R., "Cracking the carbohydrate code for selectin recognition," *Chem. and Biol.* 2(11):703–708 (Nov. 1995).

Buerke, M. et al., "Sialyl Lewis$^x$–containing Oligosaccharide Attenuates Myocardial Reperfusion Injury in Cats," *J. Clin. Invest.* 93(3):1140–1148 (Mar. 1994).

Crottet, P. et al., "Subsets of sialylated, sulfated mucins of diverse origins are recognized by L–selectin. Lack of evidence for unique oligosaccharide sequences mediating binding," *Glycobiol.* 6(2):191–208 (Mar. 1996).

DeFrees, S. A. et al., "Ligand Recognition by E–Selectin: Analysis of Conformation and Activity of Synthetic Monomeric and Bivalent Sialyl Lewis X Analogs," *J. Am. Chem. Soc.* 115(16):7549–7550 (1993).

DeFrees, S. A. et al., "Ligand Recognition by E–Selectin: Synthesis, Inhibitory Activity, and Conformational Analysis of Bivalent Sialyl Lewis x Analogs," *J. Am. Chem. Soc.* 117(1):66–79 (Jan. 1995).

de Vries, T. et al., "Efficient enzymatic synthesis of the sialyl–Lewis$^x$ tetrasaccharide: A ligand for selectin–type adhesion molecules," *FEBS Letters* 330(3):243–248 (Sep. 1993).

Hemmerich, S. et al., "Structure of the O–Glycans in GlyCAM–1, an Endothelial–derived Ligand for L–selectin," *J. Biol. Chem.* 270(20):12035–12047 (May 1995).

Hirota, K. et al., "Highly expressed human sialyl Lewis$^x$ antigen on cell surface of *Streptococcus gallolyticus*," *The Lancet* 347(9003):760 (Mar. 1996).

Hughes, S., "Carbohydrate research—a new source of therapeutics," *Scrip Magazine* 28–31 (Apr. 1994).

Ichikawa, Y. et al., "Chemical–Enzymatic Synthesis and Conformational Analysis of Sialyl Lewis x and Derivatives," *J. Am. Chem. Soc.* 114(24):9283–9298 (1992).

Lasky, L. A., "Selectin–Carbohydrate Interactions and the Initiation of the Inflammatory Response," *Ann. Rev. Biochem.* 64:113–139 (Jul. 1995).

Litscher, E. S. et al., "Oligosaccharide Constructs with Defined Structures That Inhibit Binding of Mouse Sperm to Unfertilized Eggs in Vitro," *Biochem.* 34(14):4662–4669 (Apr. 1995).

Maaheimo, H. et al., "Synthesis of a divalent sialyl Lewis x O–glycan, a potent inhibitor of lymphocyte–endothelium adhesion: Evidence that multivalency enhances the saccharide binding to L–selectin," *Eur. J. Biochem.* 234(2):616–625 (Dec. 1995).

Maaheimo, H. et al., "Enzyme–aided construction of medium–sized alditols of complete O–linked saccharides: The constructed hexasaccharide alditol Gal$\beta$1–4GlcNAc$\beta$1–6Gal$\beta$1–4GlcNAc$\beta$1–6(Gal$\beta$1–3)GalNAc–ol resists the action of endo–$\beta$–galactosidase from *Bacteroides fragilis*," *FEBS Letters* 349(1):55–59 (Jul. 1994).

(List continued on next page.)

*Primary Examiner*—Kathleen K. Fonda
*Attorney, Agent, or Firm*—Sterne, Kessler, Goldstein & Fox P.L.L.C.

[57] ABSTRACT

The present invention is directed to novel compositions and their use in the treatment of inflammatory responses. Specifically, the invention is directed to novel synthetic oligosaccharide constructs, especially multiple sLe$^x$ decorated poly-N-acetyllactosamines and their use to block lymphocyte binding to correspondent oligosaccharides on the endothelial surface, and thus reduce or otherwise ameliorate an undesired inflammatory response and other disease states characterized by lymphocyte binding. Furthermore the invention is directed to the use of the novel saccharides to block bacterial adherence to endothelium and thus prevent and/or treat bacterial infections. A further use of the present invention lies in the field of cancer treatment where metastasis of sLe$^x$-positive tumor cells is inhibited by these glycans.

36 Claims, 37 Drawing Sheets

OTHER PUBLICATIONS

Majuri, M.-L. et al., "Expression and Function of α2,3-Sialyl- and α1,3/1,4-Fucosyltransferases in Colon Adenocarcinoma Cell Lines: Role in Synthesis of E-Selectin Counter-Receptors," *Int. J. Cancer* 63(4):551–559 (Nov. 1995).

Majuri, M.-L. et al., "Recombinant E-selectin-protein mediates tumor cell adhesion via sialyl-Lea and sialyl-Lex," *Biochem. Biophys. Res. Comm.* 182(3):1376–1382 (Feb. 1992).

Malhotra, R. et al., "Anionic phospholipids bind to L-selectin (but not E-selectin) at a site distinct from the carbohydrate-binding site," *Biochem J.* 314(1):297–303 (Feb. 1996).

Mulligan, M. S. et al., "Protective effects of oligosaccharides in P-selectin-dependent lung injury," *Nature* 364(6433):149–151 (Jul. 1993).

Natunen, J. et al., "Enzymatic synthesis of two lacto-N-neohexaose-related Lewis x heptasaccharides and their separation by chromatography on immobilized wheat germ agglutinin," *Glyobiol.* 4(5):577–583 (Oct. 1994).

Niemelä, R. et al., "α1,3-Fucosylation of branched blood group I-type oligo-(N-acetyllactosamino) glycans by human milk transferases is restricted to distal N-acetyllactosamine units: The resulting isomers are separated by WGA-agarose chromatography," *Glycoconjugate J.* 12(1):36–44 (Feb. 1995).

Norgard, K. E. et al., "Characterization of a Specific Ligand for P-selectin on Myeloid Cells: A Minor Glycoprotein with Sialylated O-linked Oligosaccharides," *J. Biol. Chem.* 268(17):12764–12774 (Jun. 1993).

Paavonen, T. et al., "Selective Expression of Sialyl-Lewis X and Lewis A Epitopes, Putative Ligands for L-selectin, on Peripheral Lymph-node High Endothelial Venules," *Am. J. Pathol.* 141(6):1259–1264 (Dec. 1992).

Powell, L. D. et al., "Characterization of Sialyloligosaccharide Binding by Recombinant Soluble and Native Cell-associated CD22: Evidence for a Minimal Structural Recognition Motif and the Potential Importance of Multisite Binding," *J. Biol. Chem.* 270(13):7523–7532 (Mar. 1995).

Renkonen, O. et al., "*Escherichia coli* β-galactosidase unexpectedly cleaves the hexasaccharide Galβ1–4GlcNAcβ1–3(Galβ1–4GlcNAcβ1–6)Galβ1–4GlcNAc without branch specificity," *Biochem Cell Biol.* 68(7–8):1032–1036 (1990).

Renkonen, O. et al., "The Linear Tetrasaccharide, Galβ1–4GlcNacβ1–6Galβ1–4GlcNAc, Isolated from Radiolabeled Teratocarcinoma Poly–N–acetyllactosaminoglycan Resists the Action of E. freundii Endo–β–galactosidase," *Glycoconjugate J.* 6(1):129–140 (1989).

Renkonen, R. et al., "Characterization of High Endothelial-like Properties of Peritubular Capillary Endothelium During Acute Renal Allograft Rejection," *Am. J. Pathol.* 137(3):643–651 (Sep. 1990).

Renouf, D. V. et al., "Conformational studies of the backbone (poly-N-acetyllactosamine) and the core region sequences of O-linked carbohydrate chains," *Int. J. Biol. Macromol.* 15(1):37–42 (Feb. 1993).

Seppo, A. et al., "Synthesis of a tetravalent sialyl Lewis x glycan, a high-affinity inhibitor of L-selectin-mediated lymphocyte binding to endothelium," *Glycobiol.* 6(1):65–71 (Jan. 1996).

Seppo, A. et al., "Enzymatic Synthesis of Octadecameric Saccharides of Multiply Branched Blood Group I-Type, Carrying Four Distal α1,3-Galactose or β1,3-GlcNAc Residues," *Biochem.* 34(14):4655–4661 (Apr. 1995).

Seppo, A. et al., "Wheat germ agglutinin chromatography of GlcNAcβ1–3(GlcNAcβ1–6)Gal and GlcNAcβ1–3(GlcNAcβ1–6)Galβ1–4GlcNAc, obtained by in vitro synthesis and by partial cleavage of teratocarcinoma poly-N-acetyllactosaminoglycans," *Biochem. Cell Biol.* 68(1):44–53 (1990).

Turunen, J. P. et al., "De Novo Expression of Endothelial Sialyl Lewis$^a$ and Sialyl Lewis$^x$ during Cardiac Transplant Rejection: Superior Capacity of a Tetravalent Sialyl Lewis$^x$ Oligosaccharide in Inhibiting L-Selectin-dependent Lymphocyte Adhesion," *J. Exp. Med.* 182(4):1133–1141 (Oct. 1995).

Turunen, J. P. et al., "Sialyl Lewis$^x$- and L-selectin-dependent site-specific lymphocyte extravasation into renal transplants during acute rejection," *Eur. J. Immunol.* 24(5):1130–1136 (May 1994).

Turunen, J. P. et al., "Evidence That Lymphocyte Traffic into Rejecting Cardiac Allografts Is CD11a- and CD49d-Dependent," *Transplantation* 54(6):1053–1058 (Dec. 1992).

Vilkman, A. et al., "Elongation of both branches of biantennary backbones of oligo-(N-acetyllactosamino)glycans by human serum (1→3)-N-acetyl-β-D-glucosaminyltransferase," *Carbohydrate Res.* 226(1):155–174 (1992).

Welply, J. K. et al., "Multivalent sialyl-LeX: potent inhibitors of E-selectin-mediated cell adhesion; reagent for staining activated endothelial cells," *Glycobiol.* 4(3):259–265 (Jun. 1994).

Wilkins, P. P. et al., "Structures of the O-Glycans on P-selectin Glycoprotein Ligand-1 from HL-60 Cells," *J. Biol. Chem.* 271(31):18732–18742 (Aug. 1996).

English language abstract of WO 95/01361 (Document AO2), Dialog File 351, WPI Acc. No.: 95–060942/08, Jan. 1995.

English language abstract of WO 95/06057 (Document AP2), Dialog File 351, WPI Acc. No.: 95–115200/15, Mar. 1995.

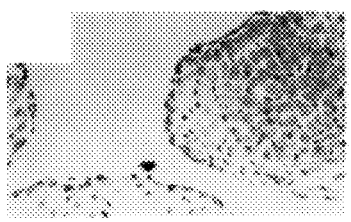 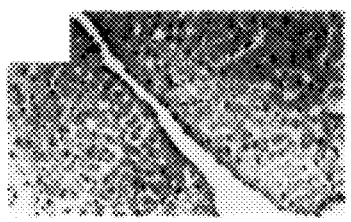 
FIG.1A   FIG.1B   FIG.1C
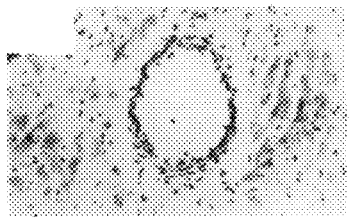 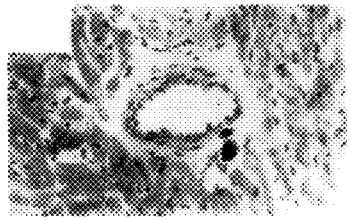 
FIG.1D   FIG.1E   FIG.1F

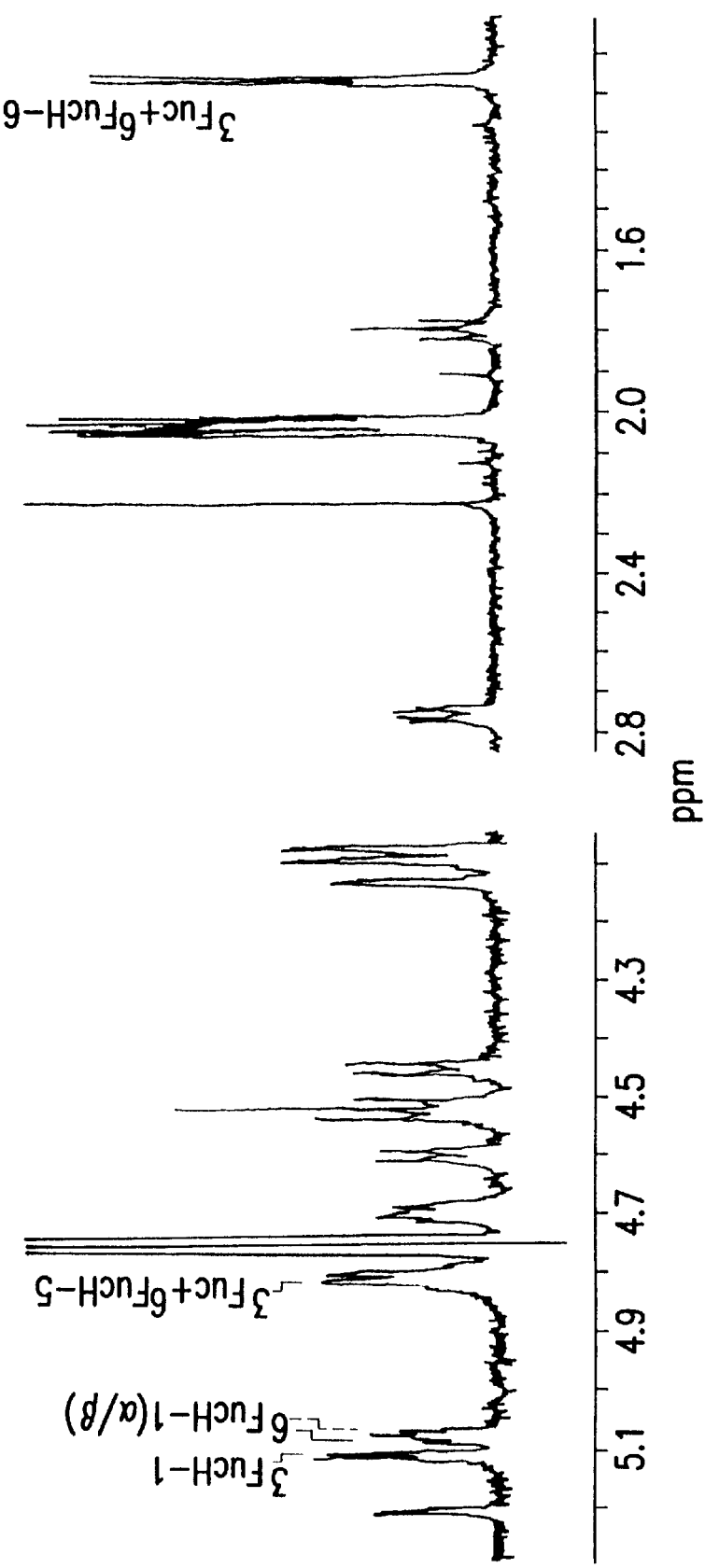

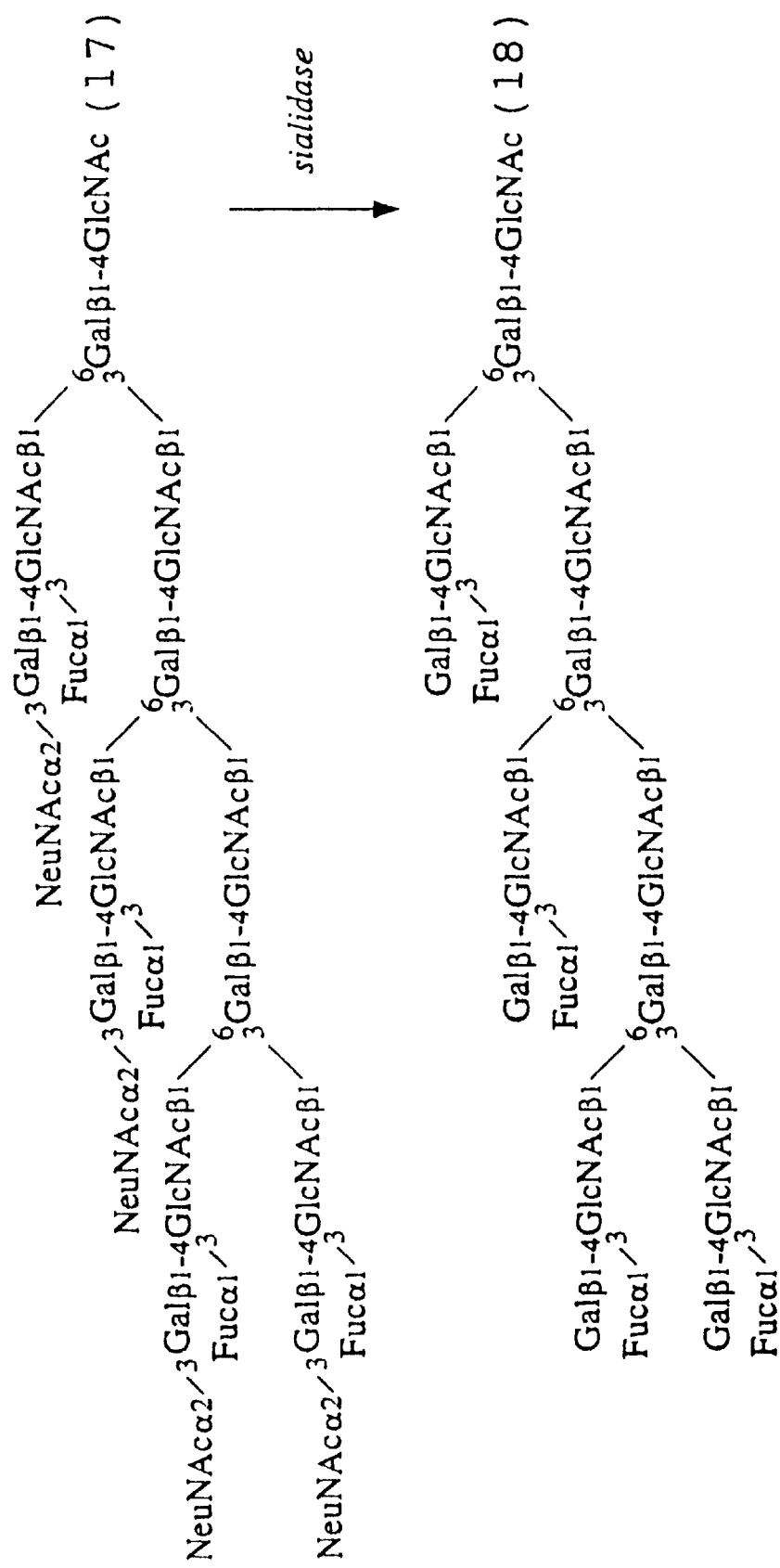

| $^1$H-NMR CHEMICAL SHIFTS OF STRUCTURAL REPORTER GROUPS OF GLYCANS 16 AND 17 AT 23 °C ||||||
| RESIDUE | n:o$^{a)}$ | PROTON | GLYCAN ||
| | | | 16 | 17 |
|---|---|---|---|---|
| GlcNAc | 1 (α) | H-1 | 5.214 | 5.214 |
| GlcNAc | 1 (β) | H-1 | 4.725 | 4.713 |
| Gal | 2,5,11 | H-1 | 4.458 | 4.452 |
| | | H-4 | 4.143 | 4.133 |
| GlcNAc$^{b)}$ | 3 | H-1 | 4.691 | 4.684/4.687 |
| GlcNAc$^{b)}$ | 4 | H-1 | 4.606/4.612 | 4.603 |
| GlcNAc | 8,14 | H-1 | 4.691 | 4.696 |
| GlcNAc | 9,15 | H-1 | 4.620 | 4.603 |
| Gal | 6,12,18 | H-1 | 4.544 | 4.517 |
| Gal | 17 | H-1 | 4.558 | 4.533 |
| | 6,12,17,18 | H-3 | 4.119 | 4.089 |
| Fuc | 7,13,20 | H-1 | – | 5.076 |
| | | H-5 | – | 4.820 |
| | | H-6 | – | 1.166 |
| Fuc | 19 | H-1 | – | 5.119 |
| | | H-5 | – | 4.820 |
| | | H-6 | – | 1.166 |
| Neu5Ac | 10,16,21,22 | H-3$_{ax}$ | 1.803 | 1.798 |
| | | H-3$_{eq}$ | 2.756 | 2.762 |

$^{a)}$NUMBERING OF THE RESIDUES IS AS FOLLOWS:

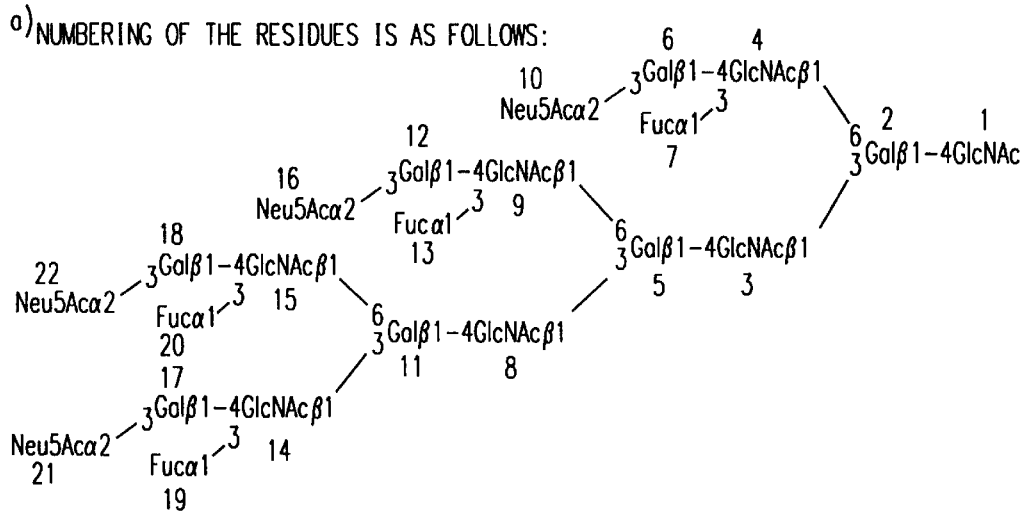

$^{b)}$ THE TWO CHEMICAL SHIFT VALUES GIVEN ARISE FROM SIGNALS REPRESENTING THE α- AND β- PYRANOSIC FORMS OF GLYCAN.

FIG.11C

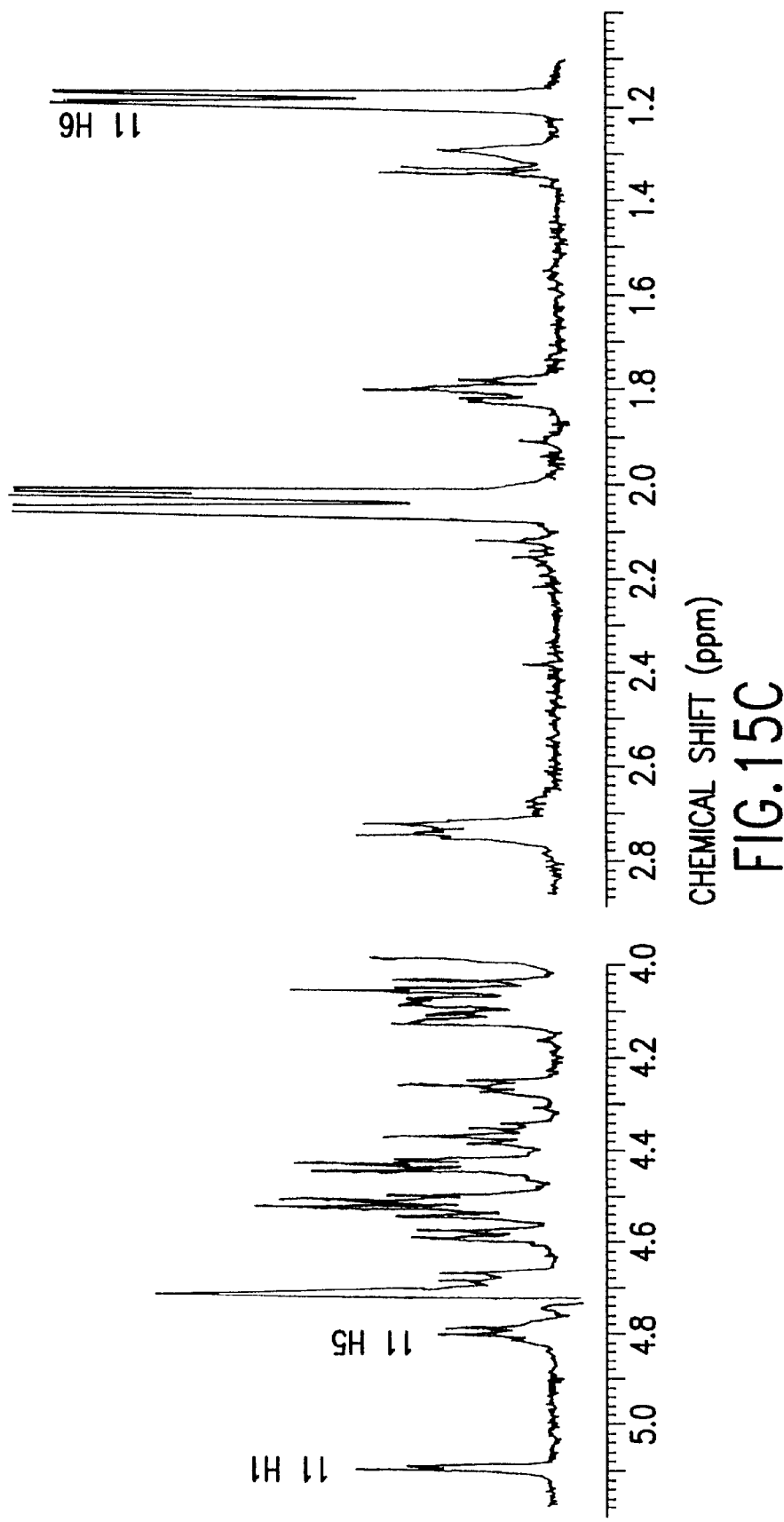

| RESIDUE | PROTON | SACCHARIDES | | | | | | | | | |
|---|---|---|---|---|---|---|---|---|---|---|---|
| | | 19 | 20 | 21 | 22 | 23 | 24 | 25 | 26 | 27 | 28 |
| 1 | H1 | 5.216(α)/4.693(β) | 5.197(α)/4.664(β) | 5.196(α)/4.664(β) | 3.793 | 3.793 | 3.794 | 3.792 | 3.793 | n.d. | 3.794 |
| | H1 | — | — | — | 3.735 | 3.732 | 3.732 | 3.732 | 3.733 | n.d. | 3.735 |
| | H2 | 4.277(α)/3.989(β) | 4.286(α)/3.972(β) | 4.287(α)/3.974(β) | 4.392 | 4.393 | 4.393 | 4.393 | 4.393 | 4.392 | 4.392 |
| | H3 | 4.032(α)/3.861(β) | 4.020(α)/3.850(β) | 4.020(α)/3.850(β) | 4.062 | 4.062 | 4.062 | 4.062 | 4.062 | n.d. | 4.063 |
| | H4 | 4.248(α)/4.181(β) | 4.214(α)/4.148(β) | 4.215(α)/4.147(β) | 3.467 | 3.465 | 3.461 | 3.462 | 3.463 | 3.462 | 3.464 |
| | H5 | 4.140(α)/3.712(β) | 4.228(α)/3.799(β) | 4.233(α)/3.768(β) | 4.281 | 4.280 | 4.284 | 4.284 | 4.284 | 4.284 | 4.281 |
| | H6 | 3.738(α)/3.79(β) | 4.011(α)/3.82(β) | 4.011(α)/3.82(β) | 3.933 | 3.930 | 3.933 | 3.931 | 3.931 | n.d. | 3.926 |
| | H6 | 3.76(β) | 3.774(α)/3.71(β) | 3.780(α)/3.76(β) | 3.683 | 3.687 | 3.687 | 3.683 | 3.683 | n.d. | 3.682 |
| 2 | H1 | 4.493/4.437 | 4.489/4.431 | 4.488/4.431 | 4.466 | 4.466 | 4.466 | 4.465 | 4.463 | 4.463 | 4.463 |
| | H2 | 3.524 | 3.520 | 3.523/3.522 | 3.561 | 3.562 | 3.562 | 3.563 | 3.565 | n.d. | 3.567 |
| | H3 | 3.621 | 3.625/3.614 | 3.621/3.614 | 3.662 | 3.672 | 3.671 | 3.670 | 3.670 | n.d. | 3.668 |
| | H4 | 3.912 | 3.914/3.907 | 3.912/3.907 | 3.902 | 3.902 | 3.903 | 3.901 | 3.904 | n.d. | 3.900 |
| 3 | H1 | — | 4.570/4.564 | 4.593/4.587 | 4.561 | 4.558 | 4.566 | 4.560 | 4.561 | 4.560 | 4.552 |
| | H2 | — | 3.704 | 3.759 | 3.755 | 3.757 | 3.788 | 3.780 | 3.776 | n.d. | 3.762 |
| | H3 | — | 3.543 | 3.704 | 3.696 | 3.682 | 3.696 | 3.696 | 3.699 | n.d. | 3.700 |
| | H4 | — | 3.436 | 3.719 | 3.698 | 3.695 | 3.642 | 3.645 | 3.639 | n.d. | 3.648 |
| | H5 | — | 3.465 | 3.602 | 3.599 | 3.596 | 3.599 | 3.595 | 3.597 | n.d. | 3.596 |
| | H6 | — | 3.748 | 3.837 | 3.998 | 3.995 | 3.988 | 3.987 | 3.986 | n.d. | 3.985 |
| | H6 | — | 3.926 | 3.992 | 3.831 | 3.820 | 3.824 | 3.823 | 3.823 | n.d. | 3.821 |
| 4 | H1 | — | — | 4.472 | 4.471 | 4.458 | 4.450 | 4.451 | 4.455 | 4.451 | 4.450 |
| | H2 | — | — | 3.541 | 3.538 | 3.584 | 3.573 | 3.571 | 3.568 | n.d. | 3.557 |
| | H3 | — | — | 3.669 | 3.661 | 3.724 | 3.710 | 3.710 | 3.711 | n.d. | 3.701 |
| | H4 | — | — | 3.929 | 3.927 | 4.450 | 4.138 | 4.144 | 4.140 | n.d. | 4.134 |
| | H5 | — | — | 3.729 | 3.72 | n.d. | n.d. | n.d. | n.d. | n.d. | n.d. |
| | H6 | — | — | 3.74 | 3.76 | n.d. | n.d. | n.d. | n.d. | n.d. | n.d. |

FIG. 15E

| | | 19 | 20 | 21 | 22 | 23 | 24 | 25 | 26 | 27 | 28 |
|---|---|---|---|---|---|---|---|---|---|---|---|
| 5 | H1 | — | — | — | — | 4.684 | 4.679 | 4.700 | 4.695 | 4.701 | 4.703 |
| | H2 | — | — | — | — | 3.756 | 3.750 | 3.800 | 3.800 | n.d. | 3.963 |
| | H3 | — | — | — | — | 3.567 | 3.567 | 3.73 | n.d. | n.d. | 3.878 |
| | H4 | — | — | — | — | 3.474 | 3.474 | 3.739 | 3.73 | n.d. | 3.917 |
| | H5 | — | — | — | — | 3.437 | 3.437 | 3.581 | 3.583 | n.d. | 3.568 |
| | H6 | — | — | — | — | 3.898 | 3.901 | 3.960 | 3.965 | n.d. | 3.98 |
| | H6 | — | — | — | — | 3.761 | 3.761 | 3.856 | 3.868 | n.d. | 3.897 |
| 6 | H1 | — | — | — | — | — | 4.585 | 4.618 | 4.608 | 4.607 | 4.606 |
| | H2 | — | — | — | — | — | 3.680 | 3.724 | 3.736 | n.d. | 3.907 |
| | H3 | — | — | — | — | — | 3.547 | 3.70 | n.d. | n.d. | 3.866 |
| | H4 | — | — | — | — | — | 3.427 | 3.710 | 3.711 | n.d. | 3.941 |
| | H5 | — | — | — | — | — | 3.452 | 3.591 | 3.591 | n.d. | 3.592 |
| | H6 | — | — | — | — | — | 3.916 | 3.975 | 3.975 | n.d. | 3.999 |
| | H6 | — | — | — | — | — | 3.740 | 3.827 | 3.840 | n.d. | 3.880 |
| 7 | H1 | — | — | — | — | — | — | 4.480 | 4.557 | 4.528 | 4.532 |
| | H2 | — | — | — | — | — | — | 3.542 | 3.571 | n.d. | 3.525 |
| | H3 | — | — | — | — | — | — | 3.665 | 4.116 | n.d. | 4.090 |
| | H4 | — | — | — | — | — | — | 3.926 | 3.960 | n.d. | 3.934 |
| 8 | H1 | — | — | — | — | — | — | 4.465 | 4.542 | 4.542 | 4.515 |
| | H2 | — | — | — | — | — | — | 3.546 | 3.573 | n.d. | 3.525 |
| | H3 | — | — | — | — | — | — | 3.665 | 4.116 | n.d. | 4.090 |
| | H4 | — | — | — | — | — | — | 3.926 | 3.960 | n.d. | 3.934 |

| | | 19 | 20 | 21 | 22 | 23 | 24 | 25 | 26 | 27 | 28 |
|---|---|---|---|---|---|---|---|---|---|---|---|
| 9 | H3ox | — | — | — | — | — | — | — | 2.756 | 2.760 | 2.762 |
| | H3eq | — | — | — | — | — | — | — | 1.800 | 1.794 | 1.796 |
| | H4 | — | — | — | — | — | — | — | 3.689 | n.d. | 3.684 |
| | H5 | — | — | — | — | — | — | — | 3.849 | n.d. | 3.851 |
| | H6 | — | — | — | — | — | — | — | 3.636 | n.d. | 3.660 |
| | H7 | — | — | — | — | — | — | — | 3.593 | n.d. | 3.597 |
| | H8 | — | — | — | — | — | — | — | 3.892 | n.d. | 3.897 |
| | H9 | — | — | — | — | — | — | — | 3.875 | n.d. | 3.877 |
| | H9 | — | — | — | — | — | — | — | 3.645 | n.d. | 3.648 |
| 10 | H3ox | — | — | — | — | — | — | — | 2.756 | 2.754 | 2.763 |
| | H3eq | — | — | — | — | — | — | — | 1.800 | 1.801 | 1.796 |
| | H4 | — | — | — | — | — | — | — | 3.689 | n.d | 3.684 |
| | H5 | — | — | — | — | — | — | — | 3.849 | n.d | 3.851 |
| | H6 | — | — | — | — | — | — | — | 3.636 | n.d | 3.660 |
| | H7 | — | — | — | — | — | — | — | 3.593 | n.d | 3.597 |
| | H8 | — | — | — | — | — | — | — | 3.892 | n.d | 3.897 |
| | H9 | — | — | — | — | — | — | — | 3.875 | n.d | 3.877 |
| | H9 | — | — | — | — | — | — | — | 3.645 | n.d | 3.648 |
| 11 | H1 | — | — | — | — | — | — | — | — | 5.116 | 5.117 |
| | H2 | — | — | — | — | — | — | — | — | n.d. | 3.676 |
| | H3 | — | — | — | — | — | — | — | — | n.d. | 3.901 |
| | H4 | — | — | — | — | — | — | — | — | n.d. | 3.783 |
| | H5 | — | — | — | — | — | — | — | — | 4.819 | 4.819 |
| | H6 | — | — | — | — | — | — | — | — | 1.167 | 1.167 |

| | 19 | 20 | 21 | 22 | 23 | 24 | 25 | 26 | 27 | 28 |
|---|---|---|---|---|---|---|---|---|---|---|
| H1 | — | — | — | — | — | — | — | — | — | 5.086 |
| H2 | — | — | — | — | — | — | — | — | — | 3.687 |
| H3 | — | — | — | — | — | — | — | — | — | 3.889 |
| H4 | — | — | — | — | — | — | — | — | — | 3.779 |
| H5 | — | — | — | — | — | — | — | — | — | 4.816 |
| H6 | — | — | — | — | — | — | — | — | — | 1.167 |

SYNTHETIC MULTIVALENT SLE$^x$ CONTAINING POLYLACTOSAMINES AND METHODS FOR USE

CROSS-REFERENCE TO RELATED APPLICATION

This application claims priority to the earlier-filed U.S. Provisional Application Ser. Nos. 60/007,867, filed Dec. 1, 1995, and 60/004,623, filed Sep. 29, 1995.

FIELD OF THE INVENTION

The present invention is directed to novel compositions and their use in the treatment of inflammatory responses. Specifically, the invention is directed to novel synthetic oligosaccharide constructs, especially multiple sLe$^x$ decorated poly-N-acetyllactosamines and their use to block lymphocyte binding to correspondent oligosaccharides on the endothelial surface, and thus reduce or otherwise ameliorate an undesired inflammatory response and other disease states characterized by lymphocyte binding. Furthermore the invention is directed to the use of the novel saccharides to block bacterial adherence to endothelium and thus prevent and/or treat bacterial infections. A further use of the present invention lies in the field of cancer treatment where metastasis of sLe$^x$-positive tumor cells is inhibited by these glycans.

BACKGROUND OF THE INVENTION

Selectin Mediated Cell Adhesion

The migration of white blood cells from the blood to regions of pathogenic exposure in the body is called the inflammatory cascade. Cell adhesion events allow for specific binding of a leukocyte to the endothelium of the vessel that is adjacent to the inflammatory insult; such adhesion events counteract the high vascular shear forces and high blood flow rates that tend to keep the leukocyte circulating, and help guide the leukocyte to the required site.

Four families of vascular adhesion molecules are involved in the migration of leukocytes during the inflammatory response: (1) the integrin family, (2) the counterreceptors of the integrin family, the immunoglobulin superfamily, (3) the selectin family, and (4) the counterreceptors of the selectin family, specialized carbohydrates displayed by the sialomucin adhesion family.

Selectins are also known as "lectin cell adhesion molecules" (LEC-CAMs). Selectins are classified into three groups: L-selectin (LECAM-1, LAM-1, gp90$^{MEL}$, Leu-8, TQ-1, CD62L and DREG) is expressed on various leukocytes, and is constitutively expressed on lymphocytes, monocytes, neutrophils, and eosinophils. E-selectin (LECAM-2, CD62E and ELAM-1) is expressed on endothelium activated by inflammatory mediators. P-selectin (GMP-140, PADGEM, LECAM-3 and CD62P) is stored in alpha granules of platelets and Weibel-Palade bodies of endothelial cells and is also expressed on endothelium activated by inflammatory stimuli. All members of the selectin family appear to mediate cell adhesion through the recognition of carbohydrates.

The current concept of leukocyte extravasation is based on the consecutive action of several adhesion molecules located on the surface of leukocytes and the endothelium. Lymphocyte extravasation is initiated by the interaction of members of the selectin family and their oligosaccharide-containing counterreceptors. For a review of the current knowledge on lymphocyte adhesion, see e.g., Springer, T. A., *Annu. Rev. Physiol.* 57: 827–872 (1995).

All selectins bind to sialyl Lewis x (NeuNAcα2-3Galβ1-4(Fucα1-3)GlcNAc) (sLe$_x$ or sLex) and sialyl Lewis a (NeuNAcα2-3Galβ1-3(Fucα1-4)GlcNAc) (sLe$^a$ or sLea) as well as related carbohydrate sequences (Bertozzi, C., *Chemistry and Biology* 2:703–708 (1995)). L-selectin-dependent recognition precedes normal lymphocyte extravasation into peripheral lymph nodes (Gallatin, W. M. et al., *Nature* 303:30–34 (1983)) and into sites of inflammation (Ley, K. et al., *Blood* 77:2553–2555 (1991)), both of which are impaired in L-selectin deficient mice (Arbones, M. L. et al., *Immunity* 1:247–260 (1994)).

Three glycoprotein ligands for L-selectin are currently known: GlyCAM-1, CD34 and MAdCAM-1. The exact structures of the biological ligands of L-selectin are not yet known, but the principal carbohydrate epitopes share some structural features. They are O-glycosidically linked mucin type oligosaccharides with an N-acetyllactosamine backbone, which is 3N-sialylated or 3N-sulphated, 3-fucosylated and sometimes 6- or 6N-sulphated at the distal N-acetyllactosamine termini.

Multivalency of the saccharide ligands enhances selectin binding. Past studies have shown that the ability of an oligosaccharide to inhibit L-selectin-mediated leukocyte adhesion to the endothelium increases with increasing numbers of sialyl L$^x$ groups (Turunen, J. P. et al., *J. Exp. Med.* 182(4):1133–1141 (1995)), and multivalent sialyl Le$^x$ structures are particularly potent as E-selectin inhibitors (DeFrees, S. A. et al., *J. Am. Chem. Soc.* 115:7549–7550 (1993); Welply, J. K. et al., *Glycobiology* 4:259–265 (1994); DeFrees, S. A. et al, *J. Am. Chem. Soc.* 117:66–79 (1995)). The polylactosamine backbone of P-selectin ligand PSGL-1 is branched and contains several fucoses (Wilkins, P. P. et al., *J. Biol. Chem.* 271:18732–18742 (1996)), and the presence of multiply fucosylated and multiply sulphated glycans in GlyCAM-1 (Hemmerich, S. et al., *J. Biol. Chem.* 270:12035–12047 (1995)) suggest that also the single natural carbohydrate ligands for selectins may be multivalent.

High endothelial cells in peripheral lymph nodes express sialyl Lewis a and sialyl Lewis x (sLe$^a$ and sLe$^x$) epitopes (Paavonen and Renkonen, *Am. J. Pathol.* 141:1259–1264 (1992); Munro, J. M. et al., *Am. J. Pathol.* 141:1397–1408 (1992); Sawada, M. et al., *Biochem. Biophys. Res. Comm.* 193:337–347 (1993)) which are parts of the L-selectin counterreceptor. The endothelial cells in several other locations are sLe$^a$ and sLe$^x$ negative, but inflammatory stimuli can induce previously negative endothelium to express these oligosaccharide structures de novo (Turunen, J. et al., *Eur. J. Immunol.* 24:1130–1136 (1994)). It has been shown that cultured endothelial cells possess the machinery to generate at least sLe$^x$, since they have several functional α2,3 sialyl- and α1,3 fucosyltransferases, enzymes involved in generating sLe$^x$ from (poly)lactosamines (Majuri, M. et al., *Eur. J. Immunol.* 24:3205–3210 (1994)).

A number of studies have proposed that selectins are involved in a wide variety of acute and chronic inflammatory conditions in many tissues. It has been proposed that drugs might be designed to impede the deleterious migration of leukocytes that damage tissue in many abnormal inflammatory conditions. However, only very high concentrations (in the mM range) of monomeric charged sugars blocked the adhesion. It has been shown that a specific subset of polyvalent, anionic sugars, such as fucoidin (a polymer of fucose-4-sulfate) and yeast cell wall polyphosphomannan ester (PPME), blocked this adhesion at concentrations in the nM range (Stoolman, L. M. et al., *J. Cell Biol.* 99:1535–1540 (1984)). In addition, it has been reported that oligosaccharides derived from the sLe$^x$ structure have anti-inflammatory activities. Both the sialic acid-containing (sLe$^x$) and the sulfate (sulfo-Le$^x$) forms of this oligosaccharide have been reported to have anti-inflammatory activity in vivo (Lasky, L. A., *Annu. Rev. Biochem.* 64:113–139 (1995); Mulligan, M. S. et al., *Nature* 364:149–151 (1993); Mulligan, M. S. et al., *J. Exp. Med.* 178:623–631 (1993); Buerke, M. et al., *J. Clin. Invest.* 91:1140–1148 (1994); and Nelson, R. M. et al., *J. Clin. Invest.* 91:1157–1166 (1993)).

Since lymphocyte infiltration is essential for acute organ transplant rejection (Renkonen, R. et al., *Cell. Immunol.* 77:188–195 (1983)) analysis of the regulation of lymphocyte traffic into the graft is important. It has been shown that peritubular capillary endothelium (PTCE) in kidney transplants begin to express sLe$^x$ de novo and bind an increased number of lymphocytes during rejection (Turunen, J. et al., *Eur. J. Immunol.* 24:1130–1136 (1994)).

U.S. Pat. No. 5,352,670 to Venot et al. discloses a method for the enzymatic synthesis of an α-sialylated oligosaccharide glycoside using sialyltransferase, a CMP-sialic acid analogue as the sialic acid donor and an oligosaccharide glycoside acceptor molecule, having a βGal(1-3)βGlcNAc or βGal(1-4)βGlcNAc disaccharide on the nonreducing terminus.

International Patent Publication No. WO 95/03059 (Gaeta et al.) discloses a synthetic saccharide that contains two glycosidically linked sLe$^x$ moieties, that are useful in blocking cellular adhesion, especially by inhibiting E-selectin binding. These sLex containing oligosaccharides are synthesized on a galactose backbone.

SUMMARY OF THE INVENTION

The recognition of cell surface L-selectin by its carbohydrate ligands causes lymphocytes to roll on capillary endothelium at sites of inflammation. As this primary contact is a prerequisite for extravasation of the leukocytes to the tissue, its inhibition by free oligosaccharides capable of competing with the natural L-selectin ligands is an attractive therapeutic option.

Recognizing the importance of controlling abnormal inflammatory conditions, and cognizant of the need for drugs to mediate the same, the inventors synthesized oligosaccharides that are capable of inhibiting selectin-mediated responses. These studies culminated in the identification of novel oligosaccharides that block lymphocyte L-selectin from binding to correspondent oligosaccharides on the endothelial surface and in clinical treatments designed to reduce inflammation as a result of administration of such oligosaccharides in a patient in need of such treatment.

Accordingly, the invention is first directed to synthetic oligosaccharides, especially divalent sLe$^x$ and tetravalent sLe$^x$ oligosaccharides and other sLe$^x$ containing oligosaccharides of increasing multivalency, essentially free of natural contaminants, and compositions containing the same. The synthetic oligosaccharides of the present invention comprise a linear or branched polylactosamine backbone (LacNac)$_n$, where n≧1 and the interresidual links are β1-3' and/or β1-6', to which NeuNacα2-3Galβ1-4(Fuc1-3)GlcNac (sLe$^x$)epitopes are linked by β1-3' and/or β1-6'bonds, where Neu-Nac: sialic acid, Gal: galactose, Fuc: fucose, GlcNac: N-acetylglucosamine. Such oligosaccharides are shown to be capable of binding selectin molecules that are on the outer surface of lymphocytes, especially L-selectin, thereby preventing the lymphocytes from binding to selectin correspondent oligosaccharides on the endothelial surface.

The invention is further directed to the tetravalent sLe$^x$ glycan of a branched polylactosamine backbone. Compared to monovalent sLe$^x$ tetrasaccharide, it proved to be a 100-fold more potent inhibitor of L-selectin-mediated lymphocyte adhesion to endothelium in rejecting cardiac and renal transplants of rats.

The invention is further directed to the tetravalent sLe$^x$ glycan, which carries the sLe$^x$ residues on a linear polylactosamine backbone. The tetravalent sLe$^x$ glycan having a linear backbone of three LacNac residues is a powerful inhibitor of L-selectin-mediated cell adhesion.

The invention is further directed to oligosaccharides fulfilling several of the features characteristic to the L-selectin ligands: specifically, a dodecameric O-glycosidic core 2 type oligosaccharide alditol with a branched polylactosamine backbone carrying two distal α2,3' sialylated and α1,3 fucosylated N-acetyllactosamine groups (sialyl Lewis x, sialyl Le$^x$). In this embodiment, the NeuNacα2-3Galβ1-4 (Fuc1-3)GlcNac (sLe$^x$)epitopes may be bonded by β1-3'-, β1-6'-, or β1-6-linkage to the disaccharide alditol. The mono-fucosylated alditol (i.e., monovalent sialyl Le$^x$) significantly inhibited L-selectin-dependent lymphocyte binding, and the difucosylated dodecasaccharide alditol (i.e., divalent sialyl Le$^x$) was a very potent inhibitor (IC$_{50}$, inhibitory concentration preventing 50% of binding=0.15 μM).

The invention is also directed to a method of enzymatically synthesizing such oligosaccharides and alditols.

The invention is further directed to a method for inhibiting lymphocyte selectin-mediated binding to endothelial surfaces, especially L-selectin-mediated binding, but also E- and P-selectin binding, by the administration of the oligosaccharide compositions of the invention, including the aforementioned enzymatically synthesized alditols, especially where such lymphocyte-endothelial cell adhesion reaction is associated with chronic or acute inflammation that is the result of transplantation rejection, arthritis, rheumatoid arthritis, infection, dermatosis, inflammatory bowel disease, and autoimmune disease.

The invention is further directed to a method for preventing and/or treating bacterial infections by the administration of the oligosaccharide compositions of the invention.

The invention is further directed to a method for treating cancer by the administration of the oligosaccharide compositions of the invention.

The invention is further directed to a method for blocking or impeding the deleterious migration of leukocytes to the site of pathogenic exposure in any inflammatory condition.

A. Analysis of the products of galactosyltransferase reaction of saccharide 24 by HPAEC with 60 mM NaOH as eluent. The calculated positions of non-, mono-, and digalactosylated products are indicated.

B. Analysis of the reaction mixture after sialyltransferase reaction of saccharide 25 by anion exchange chromatography on a Mono Q column. Disialyldecasaccharide 26 was obtained as major product. The other two peaks on the area of charged oligosaccharides are CMP (a) and NeuAc (b)

C. Separation of mono- and difucosylated saccharides (27 and 28, respectively) resulting from fucosyltransferase reaction of 26 by HPAEC. A linear gradient of NaAc was applied from 100 mM NaOH, 25 mM NaAc at 0 min to 100 mM NaOH, 100 mM NaAc at 20 min.

FIG. 15 (panels A–E). Expansions of $^1$H-NMR spectra of saccharides 25 (panel A), 26 (B), 27 (C), 28 (D), and $^1$H chemical shifts of saccharides 19–28 at 300 K (E). The resonances indicated by an asterisk are of non-carbohydrate origin.

Figure 16A:
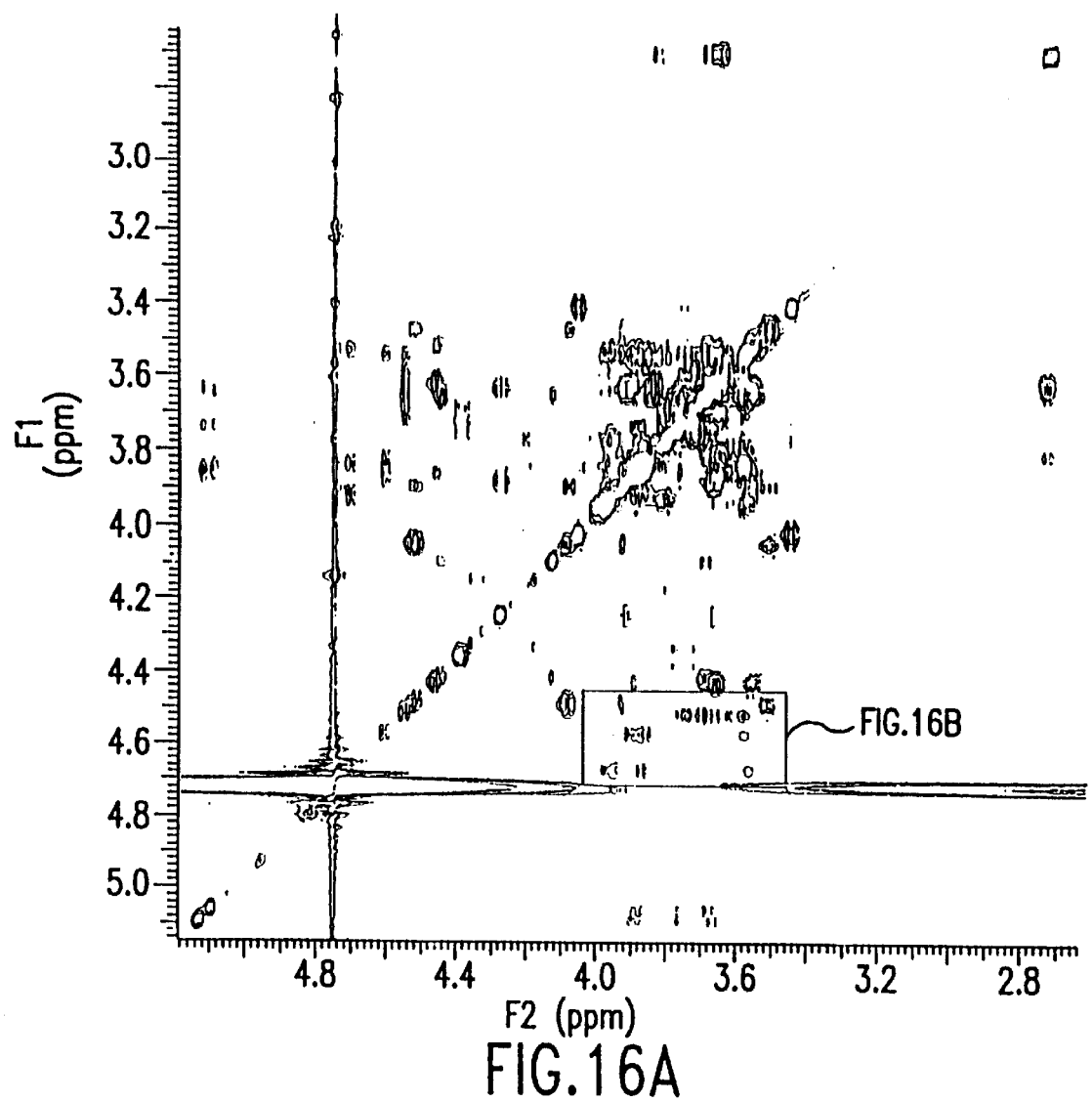
Figure 16B:
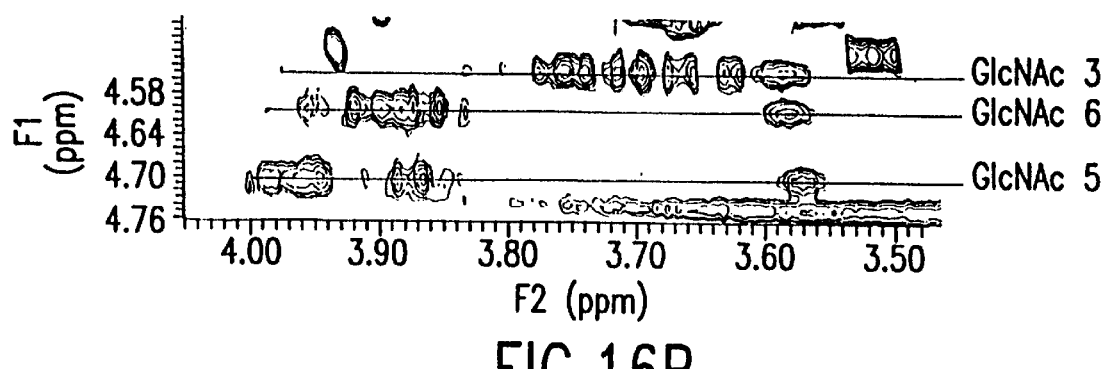

FIG. 16. Part of the TOCSY spectrum of the O-glycosidic divalent sLe$^x$ alditol 28 (spin-lock time 80 ms). From the expansion showing the correlation peaks between the anomeric and non-anomeric protons of the GlcNAc residues, the down field shift of most of the protons due to the fucosylation of the residue is evident for GlcNAc residues 5 and 6, but not for residue 3.

Figure 17:
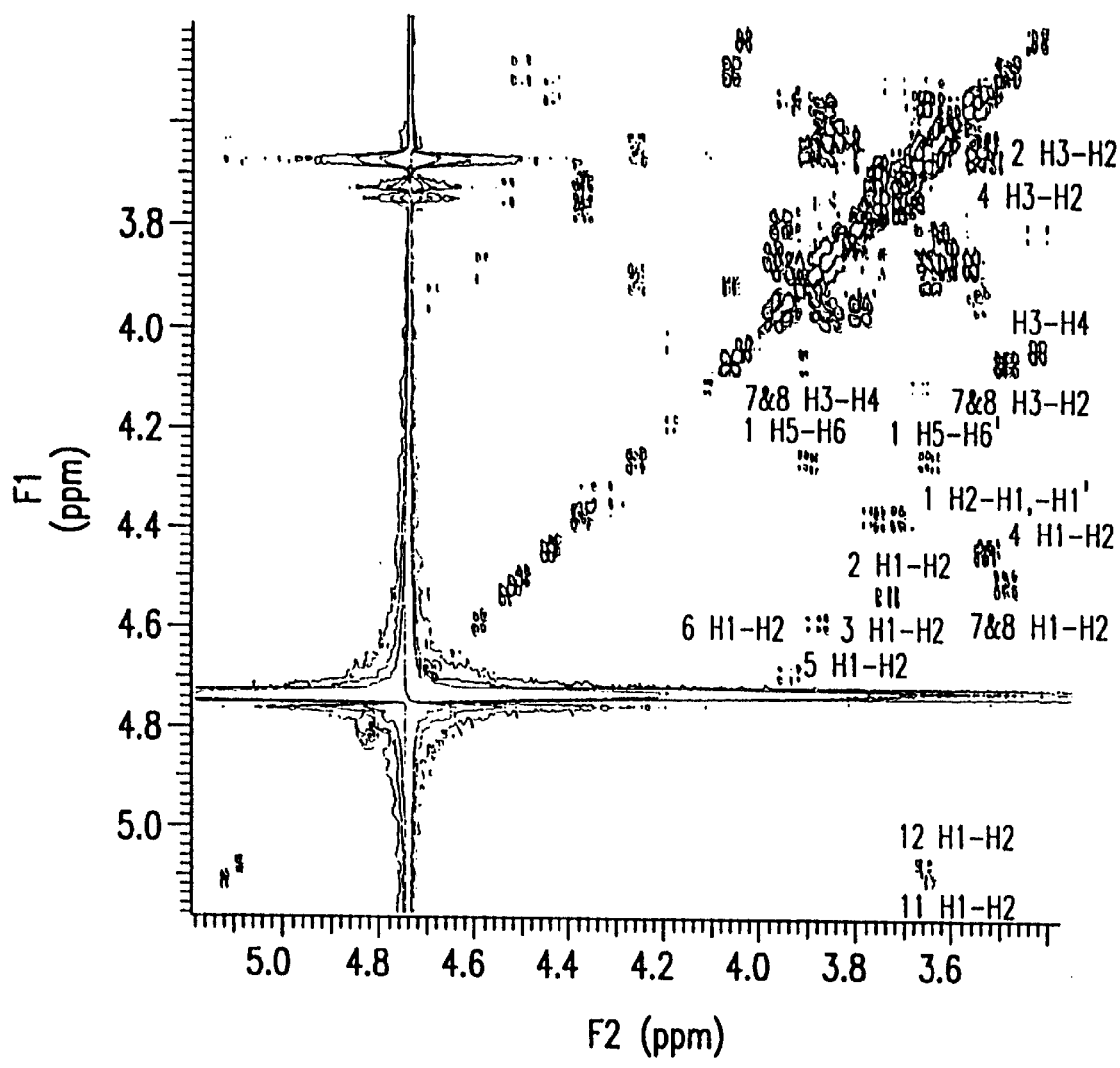

FIG. 17. The DQFCOSY spectrum of the divalent sLe$^x$ O-glycan alditol 28 employed for assigning the overlapping $^1$H-NMR resonances.

Figure 18:
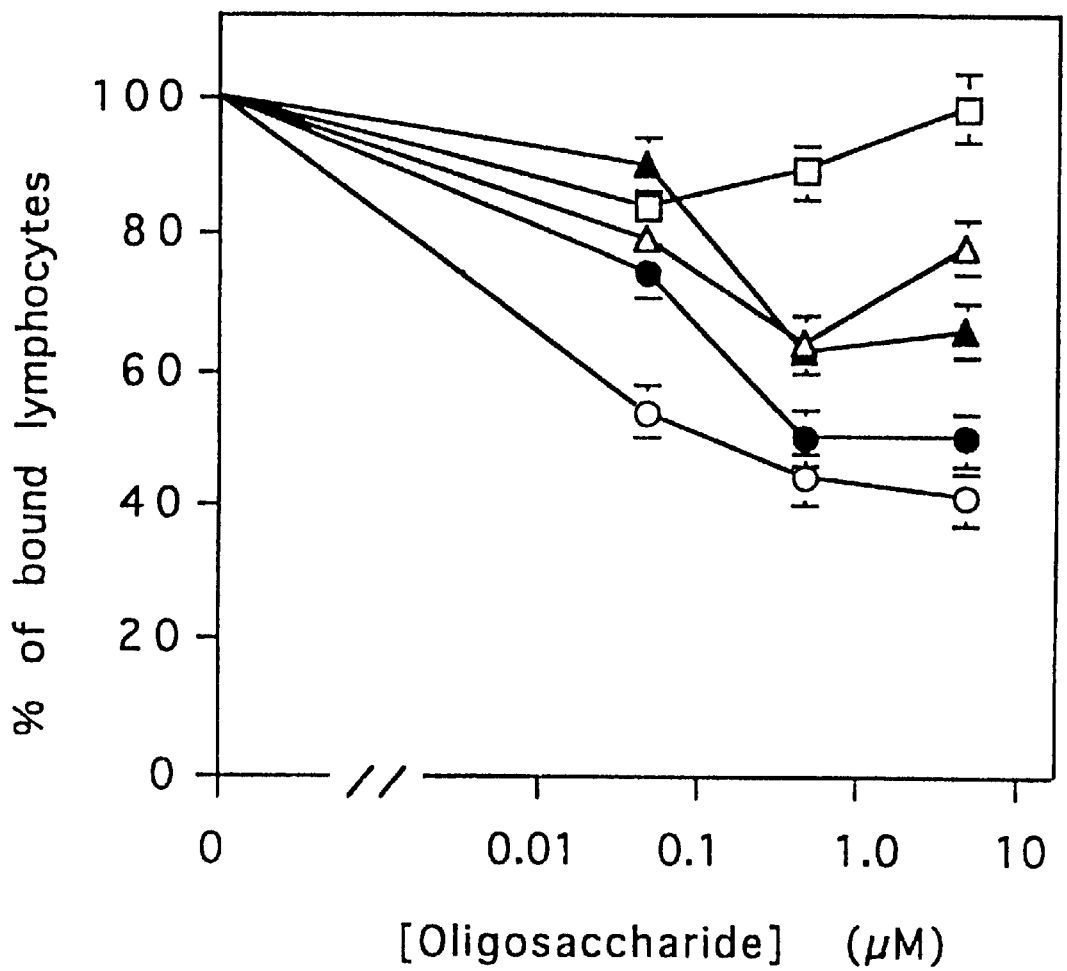

FIG. 18. Effect of enzymatically synthesized oligosaccharide constructs on the lymphocyte adhesion to peritubular capillary endothelium of rejecting kidney allografts. The symbols used are: □ O-glycan carrying two sialyl LacNAc units 26, △ monovalent sialyl Le$^x$ O-glycan 27, ○ divalent sialyl Le$^x$ O-glycan 28, ▲ monovalent sialyl Le$^x$ tetrasaccharide 1, ● divalent sialyl Le$^x$ glycan 4. The O-glycosidic type divalent dodecasaccharide alditol 28 was clearly a more potent inhibitor compared to the monovalent analog 27 lacking the fucose residue in the 6-linked arm. Concomitantly, the glycan 26, carrying no fucoses, did not inhibit the lymphocyte binding at all. The saccharide 4, lacking the reduced O-glycosidic core sequence of 28, was a slightly weaker inhibitor than 28, showing that also the O-glycosidic core sequence is important for the binding. Mean±SEM of a representative experiment of three independent ones is shown.

DETAILED DESCRIPTION OF THE PREFERRED EMBODIMENTS

The present invention relates to novel synthetic oligosaccharides and pharmaceutically acceptable compositions containing the same, and to their use in a therapeutic method for the treatment of acute or chronic inflammatory conditions. The synthetic oligosaccharides of the present invention comprise a linear or branched polylactosamine backbone (LacNac)$_n$, where n≧1 and the interresidual links are β1-3' and/or β1-6', to which NeuNacα2-3Galβ1-4(Fuc1-3)GlcNAc (sLe$^x$)epitopes are linked by β1-3' and/or β1-6'bonds, where Neu-Nac: sialic acid, Gal: galactose, Fuc: fucose, GlcNac: N-acetylglucosamine. Such oligosaccharides are preferably multimers of monovalent sLex, and especially divalent and tetravalent multimers of sLe$^x$ as diagrammed in Table 2 and in FIGS. 9 and 13. In a preferred embodiment, the synthetic oligosaccharide is the 22-saccharide tetravalent sLe$^x$ construct as shown in Table 2 and in FIG. 9. Synthesis of such multimeric forms of sLex is achieved by chemical and/or enzymatic means. For example, the construction of monovalent sLex tetrasaccharide, divalent sLex decasaccharide and tetravalent sLex 22-saccharide having a branched polylactosamine backbone can be achieved by utilizing N-acetyllactosamine, the hexasaccharide Galβ1-4GlcNAcβ1-6(Galβ1-4GlcNAcβ1-3)Galβ1-4GalNAc (Wilkman, A. et al., *Carbohydrate Res.* 226:155–174 (1993)) and the tetradecasaccharide Galβ1-3GlcNAcβ1-6(Galβ1-4GlcNAcβ1-3)Galβ1-4GlcNAcβ1-6[Galβ1-4GlcNAcβ1-6(Galβ1-4GlcNAcβ1-3)Galβ1-4GlcNAcβ1-3]Galβ1-4GlcNac (Seppo et al., *Biochem.* 34:4655–4661 (1995)) as acceptors for the mono-, di-, and tetravalent sLe$^x$ saccharides, respectively (Also see Example 2). The acceptors are first α2,3 sialylated by incubating them exhaustively with CMP-NeuNAc and α2,3 sialyltransferase from human placenta. The isolated, fully sialylated saccharides are then α1,3fucosylated exhaustively with GDP-Fucose and a partially purified preparation of human milk α1,3 fucosyltransferase(s) as in Natunen, J. et al., *Glycobiol.* 4:577–583(1994) (herein incorporated by reference). The sample sizes are estimated by UV-absorption against external N-acetylglucosamine. The characterization of the constructs was carried out by ion exchange chromatography and 1D $^1$H NMR-spectroscopy at 500 MHz. Tetravalent sLex 22-saccharide having a linear polylactosamine backbone can be achieved in five-step synthesis starting from the octameric polylactosamine LacNAcβ1-3'(GlcNAcβ1-6') LacNAcβ1-3'(GlcNAcβ1-6')LacNAc (where LacNAc is the disaccharide Galβ1-4GlcNAc) by first elongating it in a β1,3-GlcNac transferase reaction. The isolated saccharide mixture is subjected to a reaction catalyzed by β1,6-GlcNac transferase from hog gastric mucosa. The resulting oligosaccharide is then converted in a β1,4-galactosyl transferase reaction into a branched array of seven LacNac units, which is further sialylated and fucosylated to the tetravalent sLex saccharide (also see Example 6).

The present invention further relates to the enzymatic synthesis of oligosaccharide alditols which share several of the features characteristic of the L-selectin ligands, and which are capable of acting as potent inhibitors of L-selectin ligand binding. In this embodiment, the NeuNacα2-3Galβ1-4(Fuc1-3)GlcNac (sLe$^x$)epitopes may be bonded by β1-3'-, β1-6'-, or β1-6-linkage to the disaccharide alditol. Such alditols are preferably multimers of monovalent sLex, and especially divalent multimers of sLex as diagramed in FIG. 13. In a highly preferred embodiment, the alditol is a dodecameric O-glycosidic core 2 type oligosaccharide alditol with a branched polylactosamine backbone carrying two distal α2,3' sialylated and α1,3 fucosylated N-acetyllactosamine groups (sialyl Lewis x, sialyl Le$^x$) as diagramed in FIG. 13. The structure of each saccharide on the synthesis route from disaccharide Galβ1-3GalNAc to the dodecasaccharide alditol was established by several methods including 1- and 2-dimensional $^1$H-NMR spectroscopy. The last step of the synthesis, the α1,3 fucosylation of the 6-linked arm, proceeded sluggishly and was associated with a noticeable shift in H-1 resonance of the GlcNAc residue of the branch-bearing N-acetyllactosamine unit.

After analyzing several of the structural features of selectin ligands, it was decided to synthesize sialylated O-glycosidic polylactosamine alditols decorated with zero, one or two α1,3 bonded fucose residues on the sialylated N-acetyllactosamine residues. The inventors disclose here the enzymatic synthesis of the appropriate deca- to dodecasaccharides, their structural characterization by chromatography and 1- and 2-dimensional $^1$H-NMR, and their use as inhibitors for L-selectin mediated binding of lymphocytes to endothelium in a well documented model of rat kidney transplant rejection (see, e.g., Renkonen, R. et al., *Am. J. Pathol.* 137:643–651 (1990); Turunen, J. P. et al., *Eur. J. Immunol.* 24:1130–1136 (1994)).

The final synthesis product and its analogs lacking one or both of the fucose residues were tested as inhibitors of L-selectin mediated lymphocyte-endothelium interaction in vitro in rejecting rat kidney transplant. While the non-fucosylated O-glycosidic oligosaccharide alditol did not possess any inhibitory activity, the mono-fucosylated alditol (i.e., monovalent sialyl Le$^x$) prevented the binding significantly and the difucosylated dodecasaccharide alditol (i.e., divalent sialyl Le$^x$) was a very potent inhibitor (IC$_{50}$, inhibitory concentration preventing 50% of binding=0.15 μM).

In addition to the multivalency, the Galβ1-3GalNAc-ol sequence of the O-glycosidic core appeared to increase the affinity of the glycan to L-selectin. This was indicated by parallel inhibition experiments, where a disialylated and difucosylated branched polylactosamine decasaccharide, similar to the divalent dodecasaccharide alditol, but lacking the reduced O-glycosidic core, was shown to be a less effective inhibitor ($IC_{50}=0.5$ $\mu M$) than the O-glycosidic dodecasaccharide alditol. Thus, in an especially preferred embodiment of the invention, the alditol contains a Galβ1-3GalNAc-ol sequence in the O-glycosidic core.

The non-fucosylated O-glycosidic construct 26, (for saccharide numbers, see FIG. 13) did not possess any inhibitory activity, while the mono-fucosylated one (27) prevented 37% of the L-selectin-dependent lymphocyte binding at 0.5 $\mu M$. The difucosylated molecule (28) was a very potent inhibitor ($IC_{50}=0.15$ $\mu M$). Hence, the presence of multiple sialyl $Le^x$ epitopes in the distal end increases the affinity of the saccharide to L-selectin. In addition, a previously synthesized divalent sialyl $Le^x$ glycan (4), lacking the proximal Galβ1-3GalNAc-ol sequence of compound 28, revealed in parallel experiments a lesser inhibitory capacity than the alditol 28.

In the method of treating inflammation of the invention, the patient (animal and especially human) in need of such treatment is administered efficacious levels of the synthetic carbohydrate of the invention, generally in a pharmaceutically acceptable composition. The patient may also be administered compositions containing mixtures of multivalent forms, especially efficacious mixtures of the divalent and tetravalent sLex compounds shown in Table 2 and in FIGS. 9 and 13. Such pharmaceutical compositions may further contain other desired ingredients, such as, for example, antibodies or conjugates thereof that recognize and bind to leukocyte L-selectin, so as to act in concert with and enhance the efficacious ability of the synthetic carbohydrates of the invention.

By "inflammatory condition" is meant a physiological or pathological condition which is accompanied by an inflammatory response. Such conditions include, but are not limited to the various organ/tissue transplants such as skin grafts, kidney, heart, lung, liver, bone marrow, cornea, pancreas, small bowel, organ/tissue rejection, arthritis, an infection, a dermatose, inflammatory bowel disease and autoimmune diseases.

The inflammatory condition may be chronic or acute, and may be centralized in tissues that express the L-selectin counterreceptor either constitutively or in an inducible manner. As shown herein, tissues that otherwise do not express the L-selectin counterreceptors can be induced to do so in certain physiological states. For example, as shown herein, sLex expression is induced on the capillary endothelium of acutely rejected organ transplants, and this de novo sLex expression pulls lymphocytes from the circulation to the transplants, thus generating inflammation and rejection. However, the method of the invention blocks lymphocyte L-selectin from binding to correspondent oligosaccharides on the endothelial surface.

By "essentially free of contaminants" is meant that the multivalent sLex is purified to a degree such that the product contains no, or acceptable levels of, undesired or unnecessary substances that had been present during the in vitro or in vivo synthesis of said multivalent sLex.

The term "treatment" or "treating" is intended to include the administration of the synthetic oligosaccharides of the invention to a subject for purposes which may include prophylaxis, amelioration, prevention or cure of disorders mediated by selectin adhesion events, especially L-selectin-mediated adhesion events. Such treatment need not necessarily completely ameliorate the inflammatory response. Further, such treatment may be used in conjunction with other traditional treatments for reducing the inflammatory condition known to those of skill in the art.

The methods of the invention may be provided as a "preventive" treatment before detection of, for example, an inflammatory state, so as to prevent the same from developing in patients at high risk for the same, such as, for example, transplant patients.

When administered to a human or animal patient, the composition of the invention may be formulated in any manner which makes it suitable for oral, parenteral, including intravenously, intramuscularly, or subcutaneously, intracisternal, intravaginal, intraperitoneal, local, including powders, ointments, or drops, nasal, including sprays, topical, enteric, or rectal administration. Thus, the reagent may be in the form of, for instance, an injectable formulation, aerosol formulation, suspension, solution, dispersions, suspensions, emulsions, sterile powders, enema, etc. The reagent may be formulated with pharmaceutically acceptable excipients, carriers, solvents, or vehicles, e.g., isotonic saline, ethanol, polyol, polyethylene glycol, glycerol and the like, in accordance with conventional pharmaceutical practice. The dosage level of the reagent will be sufficient to provide an anti-inflammatory effect by the blocking of selectin, and especially L-selectin-mediated adhesion events in the patient.

Solid dosage forms for oral administration include capsules, tablets, pills, powders, and granules. In such solid dosage forms, the active compound may be admixed with at least one inert customary excipient, filler or extender, binder, humectant, disintegrating agent, solution retarder, wetting agent, adsorbent, lubricant, and/or buffering agent. Solid dosage forms such as tablets, dragees, capsules, pills, and granules can be prepared with coatings and shells. The active compounds can also be in microencapsulated form with one or more excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers.

Besides such inert diluents, the compositions can also include adjuvants, such as wetting agents, emulsifying and suspending agents, sweetening, flavoring, and perfuming agents.

Suspensions, in addition to the active compounds, may contain suspending agents.

The compositions of this invention can also be administered in the form of liposomes. As is known in the art, liposomes are generally derived from phospholipids or other lipid substances. Liposomes are formed by mono or multi-amellar hydrated liquid crystals that are dispersed in an aqueous medium. Any nontoxic, physiologically acceptable, and metabolizable lipid capable of forming liposomes can be used. The present compositions in liposome form can contain, in addition to the synthetic multivalent $sLe^x$ containing polylactosamines of the invention, stabilizers, preservatives, excipients, and the like. The preferred lipids are the phospholipids, and the phosphatidyl cholines (lecithins), both natural and synthetic. Methods of forming liposomes are well known in the art.

The compositions and methods of the invention are suitable for treating any condition involving a selectin, and especially an L-selectin-mediated adhesion increased inflammatory reaction. Thus, the reagent is useful for treating conditions including but not limited to septic shock, chronic inflammatory diseases such as psoriasis, and rheumatoid arthritis and reperfusion injury that occurs following heat attacks, strokes and organ transplants, traumatic shock, multi-organ failure, autoimmune diseases, asthma, inflammatory bowel disease, tissue rejection, arthritis, an infection, especially local infections, dermatoses, etc. In each case, an effective amount of the compounds of the present invention is administered either alone or as part of a pharmaceutically acceptable composition to a patient in need of such treatment. It is also recognized that a combination of the compounds may be administered to a patient in need of such administration.

Cell adhesion involving sLe$^x$ and sLex$^a$ has been shown to play a role in the metastasis of certain cancers. Accordingly, a further use of the present invention is in cancer treatment where metastasis of sLe$^x$ positive tumor cells can be inhibited by these glycans.

In another embodiment, efficacious levels of the compositions of the invention are administered so as to provide therapeutic benefits against the secondary harmful inflammatory effects of inflammation. By an "efficacious level" of a composition of the invention is meant a level at which some relief is afforded to the patient who is the recipient of the treatment. By an "abnormal" host inflammatory condition is meant a level of inflammation in the subject at a site which exceeds the norm for the healthy medical state of the subject, or exceeds a desired level. By "secondary" tissue damage or toxic effects is meant the tissue damage or toxic effects which occurs to otherwise healthy tissues, organs, and the cells therein, due to the presence of excessive selectin, and especially L-selectin, adhesion events, including as a result of a "primary" stimulus elsewhere in the body.

In the methods of the invention, infusion of the compositions of the invention into a patient results in a lessening of the ability of selectin-expressing leukocytes to "roll" and thus attach to the endothelium, thus preventing or inhibiting adherence of such cells to the site of the inflammation and the localized damage to the endothelium, and thus preventing undesired lymphocyte trafficking or influx into the affected tissues or cells.

Accordingly, the pharmaceutical compositions of the invention provide for compositions containing the synthetic carbohydrates and/or alditols of the invention, in amounts sufficient to antagonize (fully or partially) the patient's native selectin, and especially L-selectin, binding to biological targets of such selectin in such patient, and specifically to endothelial cells.

The oligosaccharides of the invention may be conjugated, either chemically or by genetic engineering, to fragments of other agents which provide a targeting of such selectin-binding compounds to a desired site of action. Alternatively, other compounds may be conjugated, either chemically or by genetic engineering, to the oligosaccharides of the invention so as to enhance or provide additional properties to such oligosaccharides or compositions containing the same, especially properties which enhance the compound's ability to promote relief of adhesion-mediated toxic effects, or promote clearance of the compound from the bloodstream, or other advantageous properties.

Amounts and regimens for the administration of selectin-binding oligosaccharides and compositions comprising the oligosaccharides of the invention can be determined readily by those with ordinary skill in the clinical art of treating inflammation-related disorders such as arthritis, tissue injury and tissue rejection. Generally, the dosage of the composition of the invention will vary depending upon considerations such as: type of synthetic carbohydrate employed; age; health; medical conditions being treated; kind of concurrent treatment, if any, frequency of treatment and the nature of the effect desired; extent of tissue damage; gender; duration of the symptoms; and, counter indications, if any, and other variables to be adjusted by the individual physician. A desired dosage can be administered in one or more applications to obtain the desired results. Pharmaceutical compositions containing the oligosaccharides of the invention, such as the tetravalent sLex 22-saccharide, or the difucosylated dodecasaccharide alditol, may be provided in unit dosage forms.

Preferably, the synthetic multivalent sLex containing polylactosamines of the present invention, e.g., the tetravalent sLex oligosaccharide, are administered to a patient in a dosage sufficient to achieve a 0.1 nM to 10,000 nM serum concentration, or higher if desired, in said patient. More preferably, the synthetic multivalent sLex containing polylactosamines of the present invention are administered to a patient in a dosage sufficient to achieve a 0.1 nM to 500 nM serum concentration in said patient.

Similarly, the synthetic sLex alditols of the present invention, e.g., the divalent sLex alditol, are preferably administered to a patient in a dosage sufficient to achieve a 0.1 nanomolar to 5.0 $\mu$M concentration, or higher if desired, in said patient. More preferably, the synthetic sLex alditols of the present invention are administered to a patient in a dosage sufficient to achieve a 0.1 nanomolar to 1.5 $\mu$M concentration in said patient.

The pharmaceutical compositions containing the synthetic oligosaccharides of the invention can be administered in any appropriate pharmacological carrier for administration. They can be administered in any form or dosage that effects prophylactic, palliative, preventative or curing conditions of selectin, and especially L-selectin, mediated events in humans and animals. For the purpose of definition, it is intended that the expression "a method of treatment" of a disease, and like expressions, throughout the specification and claims, be taken to include a method for the prevention of such disease.

The method of the invention is useful for the prevention of rejection or inflammation of transplanted tissue or organs of any type, for example, heart, lung, kidney, liver, skin grafts, tissue grafts, etc.

The compositions of the invention, may include sterile aqueous or non-aqueous solvents, suspensions and emulsions, especially when intended for parenteral administration. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles include fluid and nutrient replenishers, electrolyte replenishers, such as those based upon Ringer's dextrose and the like.

The compositions of the invention may also be administered by means of pumps, or in sustained-release form, especially, when the primary injury is prolonged or delayed rather than acute. An example in which the primary injury is often prolonged or delayed rather than acute is an infection or sprain wherein the damage to the tissue or muscle is not revealed (or persists) until days after the primary infection or damage. The selectin-binding molecules of the invention may also be delivered to specific organs in high concentration by means of suitably inserted catheters, or by providing such molecules as a part of a chimeric molecule (or complex) which is designed to target specific organs.

Administration in a sustained-release form is more convenient for the patient when repeated injections for prolonged periods of time are indicated. For example, it is desirable to administer the compositions of the invention in a sustained-release form when the methods of the invention are being used to treat a genetic or chronic inflammatory disease that is based upon a selectin-mediated disorder, so as to maximize the comfort of the patient.

The compositions of the invention can be employed in dosage forms such as tablets, capsules, powder packets, or liquid solutions for oral administration if the biological activity of the active multimeric carbohydrate is not destroyed by the digestive process and if the characteristics of the compound allow it to be absorbed across the intestinal tissue.

The pharmaceutical compositions of the present invention are manufactured in a manner which is in itself known, for example, by means of conventional mixing, granulating, dragee-making, dissolving, lyophilizing or similar processes. The compositions of the present invention, in and of themselves, find utility in the control of inflammation-mediated physiological damage, be it chronic or acute. The compositions of the invention obviate the body's own mechanisms for recognizing selectin-mediated adhesion to its maximum potential.

In intravenous dosage form, the compositions of the present invention have a sufficiently rapid onset of action to be useful in the acute management of potential tissue damage.

Additionally, a low potency version is useful in the management of mild or chronic selectin-mediated inflammatory disorders.

Acute organ transplant rejection is characterized by a heavy lymphocyte infiltration. It has previously been shown that alterations in the graft endothelium lead to increased lymphocyte traffic into the graft. The examples herein demonstrate that not only is selectin, and especially L-selectin, induced as a result of such graft in tissue that does not otherwise express such selectin, but also, that lymphocytes adhere to endothelium of rejecting cardiac transplants, but not to endothelium of syngeneic grafts or normal hearts analyzed with the in vitro Stamper-Woodruff binding assay. Several members of the sLex-family have been synthesized enzymatically and analyzed for their ability to block lymphocyte adhesion to cardiac endothelium. Monovalent sLex (tetramer), divalent sLex (decamer) and tetravalent sLex (22-mer) all significantly reduce lymphocyte binding, but the inhibition by tetravalent sLex-construct is clearly superior to other members of the sLex family. The crucial control oligosaccharides, sialyl lactosamines (sLN) lacking fucose, but being as charged as the members of sLex family, have no effect on lymphocyte binding.

Furthermore, methods of synthesizing sialylated O-glycosidic polylactosamine alditols which are potent inhibitors of L-selectin mediated lymphocyte-endothelium binding are herein disclosed. In particular, the difucosylated dodecasaccharide alditol (divalent sLe$^x$) inhibited 50% of binding at a concentration of 0.1 5 $\mu$M. The divalent sLe$^x$ alditol contains a Gal$\beta$1-3GalNAc-ol sequence in the O-glycosidic core which appears to increase the affinity of the glycan to L-selectin.

The following examples represent the first synthesis of complex oligosaccharides in sufficiently large amounts (as described in the examples) such that one can routinely conduct the types of experiments described in this application. The present invention overcomes previous difficulties in this regard.

The following examples are merely intended to illustrate the present invention and not in any way to limit its scope.

EXAMPLES

Example 1

Animal Models for L-selectin Mediated Transplant Rejection and an Assay for Adhesion Inhibition Transplant rejection is an inflammatory process characterized by lymphocyte infiltration. Earlier observations have shown that peritubular capillary endothelium (PTCE) is the site of lymphocyte entry into the rejecting renal allograft. During rejection, PTCE begins to express sialyl Lewis x de novo, and binds lymphocytes by a mechanism largely dependent on L-selectin. Hence, inhibiting the lymphocyte-endothelial interaction with oligosaccharide ligands of L-selectin offers an attractive alternative to prevent the inflammation and rejection. It has been shown previously that the number of graft-infiltrating lymphocytes increase dramatically during acute rejection from background levels of $5$–$10^6$ to over $30 \times 10^6$.

The animal models for cardiac transplant rejection and kidney transplant rejection utilized inbred WF (RT1$^v$) and DA (RT1$^a$) rat strains that were maintained in a colony and regularly tested for intrastrain acceptance of transplants as well as for the absence of intrastrain mixed lymphocyte culture. DA transplants into WF recipients were allografts, WF grafts to WF and DA grafts to DA served as syngeneic controls. The animal models are described in more detail in (Renkonen, R. et al., *Transplantation* 47:577–579 (1989); Renkonen, R. et al., *Am. J. Pathol.* 137:643–651 (1990); Turunen J. P. et al., *Transplantation* 54:1053–1058 (1992); Turunen, J. P. et al., *Eur. J. Immunol.* 24:1130–1136 (1994); Turunen, J. P. et al., *J. Exp. Med.*, 182:1133–1142 (1995)).

Stamper-Woodruff Binding Assay

Small pieces of the removed syngeneic (DA to DA and WF to WF), allogeneic (DA to WF) transplants were mounted in Tissue Tek medium (Lab-Tek Productions, Naperville, Ill.) and snapfrozen in liquid nitrogen. Eight $\mu$m thick frozen sections were prepared within one hour prior to the use of the sections in the lymphocyte—endothelium binding assay (Renkonen, R. et al., *Transplantation* 47:577–579 (1989); Renkonen, R. et al., *Am. J. Pathol.* 137:643–651 (1990); Turunen J. P. et al., *Transplantation* 54:1053–1058 (1992); Turunen, J. P. et al., *Eur. J. Immunol.* 24:1130–1136 (1994); Turunen, J. P. et al., *J. Exp. Med.*, 182:1133–1142 (1995)).

Single cell suspensions of mesenterical lymph node lymphocytes were made by mechanical disaggregation in RPMI 1640 medium (Gibco, Grand Island, N.Y.) supplemented with Hepes (25 mM) and 0.5% fetal calf serum and the cells were passed through a 50 $\mu$m pore size mesh. Over 99% of the cells were lymphocytes, and the lymphocyte population consisted of 80–90% CD3-positive T cells, 50–60% CD4-positive T cells, 25–35% CD8-positive T cells and 10–20% CD19-positive B cells, as analyzed by flow cytometric analyses and immunoperoxidase stainings from cytocentrifuge preparations.

$3 \times 10^6$ cells in 100 $\mu$l of the medium were plated on top of the tissue sections using a wax pen circle to avoid escape of the fluid. The sections were rotated horizontally on a shaker at 60 rpm for 30 minutes at +4° C. After incubation, the medium was gently tapped away by an absorbent paper and the slides were fixed in 1.5% cold glutaraldehyde overnight. The slides were stained with thionine for 30 min. The excess thionine was gently washed away from the slides in PBS, and the slides were mounted with PBS-glycerol (1:1) or Aquamount Mountant, (BHD Limited, Poole, England). From these preparations the number of lymphocytes bound to various structures was determined. At least 10–20 high power fields were analyzed from each sample and 3–4 animals were included in each group.

Lymphocyte Extravasation During Rejection of Heart Transplant

Endothelium in the tissue sections prepared from allografts bound significantly more lymphocytes compared to endothelium in sections prepared from syngeneic grafts of normal hearts (Table 1, FIG. 1).

TABLE 1

Number of in vitro adherent lymphocytes per one high-power microscopic field on normal hearts, and on syngeneic or allogeneic heart grafts at day 3 after transplantation. The mean ± SEM of seven independent experiments is presented.

|  | Normal | Syngraft | Allograft |
| --- | --- | --- | --- |
| Total area | 47.4 ± 4.3 | 71.1 ± 5.6 | 151.6 ± 16.1 |
| Endocardium | 0.1 ± 0.1 | 2.1 ± 0.7 | 2.8 ± 1.3 |
| Arterioles | 0.1 ± 0.1 | 2.1 ± 0.1 | 1.6 ± 0.7 |
| Venules | 5.2 ± 0.4 | 7.6 ± 0.5 | 12.2 ± 1.6 |
| Intermuscular Capillaries | 23.8 ± 3.1 | 42.7 ± 3.8 | 119.4 ± 12.4 |
| Myocardium | 17.3 ± 0.0 | 16.6 ± 1.1 | 15.6 ± 1.9 |

When the anatomical location was analyzed in more detail the endothelium was divided into several categories according to the size of the vascular structure: (i) endocardium, (ii) arterioles, (iii) venules, and (iv) intermuscular capillaries. Lymphocyte adhesion was assayed in these various compartments and found to be increased onto the intermuscular capillaries and venules during rejection (Table 1, FIG. 1). There was a constant low background binding of lymphocytes to the myocardium in all heart specimens.

The specificity of lymphocyte-endothelial adhesion was demonstrated in several ways: i) it was practically absent in syngeneic grafts or normal non-treated hearts (Table 1), ii) it was not affected by the origin of adherent lymphocytes (i.e both DA and WF cells adhered equally well to DA to WF grafts), and iii) it was inhibited by treating the tissue sections with sialidase prior to adding lymphocytes.

Increased Lymphocyte Binding to Endotlielium of Kidney Allografts

In the in vitro Stamper-Woodruff assay the lymphocyte binding to allograft endothelium increased four-fold compared to endothelium of syngraft or control kidneys. Majority of bound lymphocytes in the allografts was located on peritubular capillary endothelitum (PTCE), while on the other hand endothelium of major vessels and glomeruli in allografts did not adhere significantly more lymphocytes than the same structures in syngeneic grafts or normal kidneys. Lymphocyte adhesion to PTCE during kidney transplant rejection has been shown to be for the major part L-selectin-dependent. Concomitantly PTCE of rejecting kidneys showed morphological features similar to lymph node high endothelium and began to react de novo with anti-sLex mAbs and L-selectin-IgG fusion protein (Renkonen, R. et al., *Am. J. Pathol.* 137:643–651 (1990); Turunen, J. et al., *Eur. J. Immunol.* 24:1130–1136 (1994)).

Testing of Novel Adhesion Inhibiting Molecules

All novel oligosaccharide contructs according to the present invention were tested for their ability to inhibit adhesion of lymphocytes to endothelium of rat heart and kidney transplants undergoing acute rejection, which represent models where L-selectin plays an essential role. The oligosaccharides were dissolved in the binding buffer, and the lymphocytes were incubated in these solutions for 30 min in +4° C. Thereafter, the lymphocytes at the saccharide solutions were added to the Stamper-Woodruff binding assay without further washings and the assay was conducted as described above.

Example 2

Synthesis and Characterization of Synthetic Glycans (Bolded numbering corresponds to glycan structures in Table 2)

Material and Methods

Acceptor saccharides

N-acetyllactosamine (Galβ1-4GlcNAc) was purchased from Sigma. The glycans 2 and 7 were synthesized by enzyme-aided in vitro synthesis as described in (Renkonen, O. et al., *Biochem. Cell Biol.* 68:1032–1036 (1990); Seppo, A. et al., *Biochemistry* 34:4655–4662 (1995)).

Enzyme preparations

Human placental microsomes, containing α2,3-sialyltransferase activity (van den Eijnden & Schiphorst, *J. Biol. Chem.* 256:3159–3162 (1981)), were prepared as follows: 100 g of fresh human placenta was homogenized in 500 ml of cold 0.1M Tris-maleate, pH 6.7 at +4° C. The homogenate was centrifuged at 3400 g at +4° C. for 30 min and the supernatant was further centrifuged at 200,000 g +4° C. for 60 min. The microsome pellet was suspended in 10 ml of 0.1M Tris-maleate, pH 6.7, yielding a suspension containing 80 mg/ml protein (Bradford, M. M., *Anal. Biochem.* 72:248–254 (1976)).

α1,3/4-Fucosyltransferase was extracted from human milk by use of SP-Sephadex C-50 as described (Eppenberger-Castori, S. et al., *Glycoconjugate J.* 6:101–114 (1989)). Starting from 1L of thawed milk, a fucosyltransferase pool of 100 ml was obtained. The pool was concentrated to 5 ml by the use of Amicon ultrafiltration apparatus equipped with a 30 kD cut-off membrane cartridge. This preparation contained a 8 mU/ml of total fucosyltransferase and 0.79 mg/ml of protein.

Transferase Reactions

α2,3-Sialyltransferase reactions were performed in 100 μl of 0.1M tris-maleate, pH 6.7 containing the oligosaccharide acceptor corresponding to 100–200 nmol of acceptor sites (i.e. non-reducing terminal galactose residues), 10-fold molar excess CMP-NeuNAc and 25 μl of human placental microsomes containing the α2,3 sialyl transferase activity. The reaction mixtures were incubated for 12–18 hours at 37° C. and the reactions were terminated by addition of 100 μl of water and heating in a boiling water bath for 2 min. The precipitating protein was removed by centrifugation, the supernatant and washings were lyophilized and oligosaccharides were purified from the mixture by gel filtration on a Superdex 75 HR column. The α1,3/4-fucosyltransferase reactions were performed as described (Palcic, M. M. et al., *Carbohydr. Res.* 190:1–11 (1989)) and terminated by gel filtration on the Superdex 75 HR column.

Glycosidase Digestions

For sialidase reactions 1–4 nmol of oligosaccharide was dissolved in 16 μl of 0.1M sodium acetate buffer pH 5.0. The reaction was started by the addition of 40 mU (4 μl) of sialidase from *Arthrobacter ureafaciens* (Boehringer), the reaction mixture was incubated for 16 h at 37° C. and terminated by gel filtration on a Superdex 75 HR column.

For concomitant β-N-acetylhexosaminidase and β-galactosidase reaction 1–20 nmol of oligosaccharide was dissolved in 30 μl of sodium citrate buffer pH 4.0. The reaction was started by adding 150 mU (2.4 μl) of jack bean β-N-acetylhexosaminidase (Sigma) and 100 mU (15 μl) of jack bean β-galactosidase (Sigma) to the reaction mixture. After incubation (16 h at 37° C.) the reaction was terminated by heating in a boiling water bath for 3 min.

Chlromatographic methods

High pH anion exchange chromatography with pulsed amperometric detection (HPAEC-PAD) on a (4×250 mm) Dionex CarboPac PA-1 column was carried out as described in Helin, J. et al., *Carbohydr. Res.* 266:191–209 (1995). The column was eluted at a rate of 1 ml/min and was equilibrated with the starting buffer prior to sample injection. Peaks were collected manually and were neutralized immediately with the addition of 0.5 volumes of cold 0.4 acetic acid and dried with a vacuum centrifuge. The dried material was desalted by high performance liquid chromatography (HPLC) gel filtration on a Superdex 75 HR column.

Figure 5A:
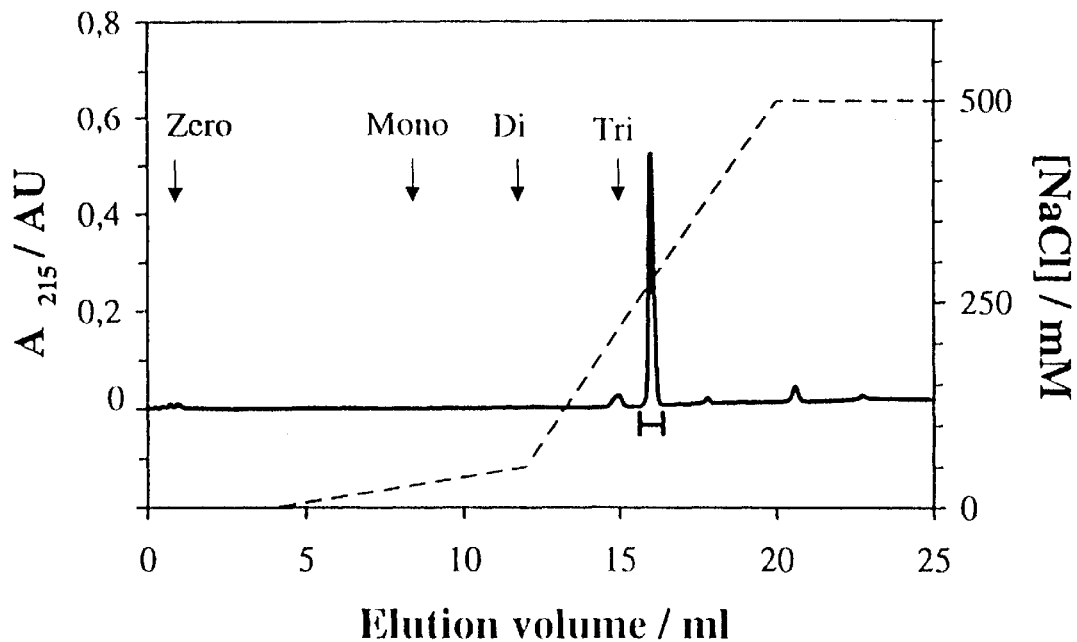
FIG. 5 (panels A–B). Chromatography analysis of intermediates and final products in the synthesis of glycan 9. A) Ion-exchange chromatography on a MonoQ 5/5HR-column of saccharides obtained from α2,3-sialyltransferase reaction of 7. Arrows marked Zero, Mono, Di and Tri denote the elution Positions of GlcNAc, 3'-sialyllactose, a disialylated and trisialylated oligosaccharide marker, respectively. UV-absorbance at 214 nm is represented by the thick line and NaCl gradient by the dashed line. The bar indicates material pooled at tetrasialo saccharide 8. B) HPAE-PAD chromatography of fucosyltransferase products of saccharide 8. Peaks labeled T1, T2 and T3 represent tetra, -tri and difucosyl products of 8, respectively. Tailing of the peaks is believed to be due to the base catalyzed 2-epimerisation of the reducing end GlcNAc of the saccharides. PAD response is indicated as a solid line, Na-acetate gradient as a dashed line.
Figure 5B:
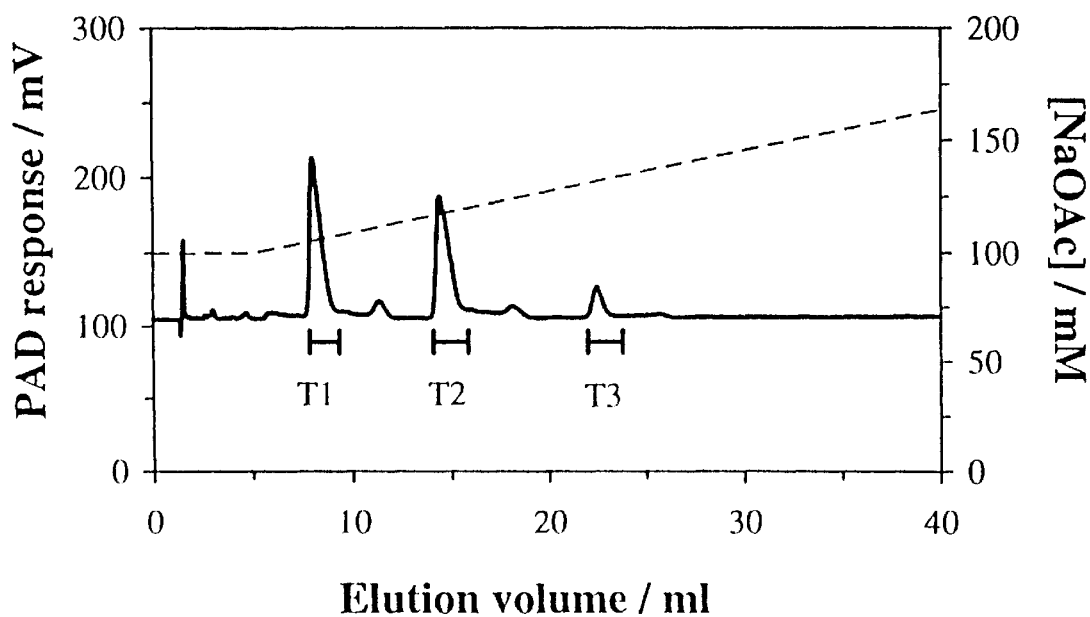

Anion exchange chromatography on a MonoQ (5/5) column (Pharmacia) was performed using a LKB 2150 HPLC pump and a LKB 2152 HPLC controller equipped with a low pressure mixer system. The column, equilibrated with water was eluted at a rate of 1 ml/min, first isocratically with water and then with linear gradients of NaCl as indicated in FIG. 5. The effluent was monitored with a Kratos Spectroflow 757 UV monitor at 214 nm or 205 nm. Mono-, di- and trisialylated markers indicated in FIG. 5 were NeuNAcα2-3Galβ1-4GlcNAc (Oxford Glycosystems), NeuNAcα2-6Galβ1-4GlcNAcβ1-2Manα1-6(NeuNAcα2-6Galβ1-4GlcNAcβ1-2Manα1-3)Manβ1-4GlcNAc and NeuNAcα2-6Galβ1-4GlcNAcβ1-2Manα1-6(NeuNAcα2-3Galβ1-4GlcNAcβ1-4[NeuNAcα2-6Galβ1-4GlcNAcβ1-2]Manα1-3)Manβ1-4GlcNAc, respectively. The latter two were generous gifts from Dr. Gerard Strecker (University of Lille, France).

HPLC gel filtration chromatography on a Superdex 75 HR (10/30) column (Pharmacia, Sweden) was performed using a LKB 2150 HPLC pump. The column was eluted at 1 ml/min using 50 mM $NH_4HCO_3$ to suppress ion exchange effects of the column. The effluent was monitored with a Spectra-Physics 8450 UV monitor at 214 nm or 205 nm. The amount of saccharide in each peak was estimated from peak areas by reference to an external calibrant (GlcNAc or NeuNAc), taking into account the number of carbonyl groups in each peak. The accuracy of quantitation is estimated to be better than ±20%.

NMR spectroscopy

Prior to NMR analysis the oligosaccharide samples were repeatedly dissolved in 99.96% $D_2O$ (C.I.L., MA, USA) and lyophilized. Finally the samples were dissolved in 99.996% $D_2O$ and passed through a nylon membrane filter. $^1$H-NMR spectra were recorded using a Varian Unity-500 spectrometer operating at a proton frequency of 500 MHz. The probe temperature was thermostated to 23 or 27° C. The carrier frequency was placed on top of the residual $H_2O$/HDO signal and solvent suppression was achieved using a modified WEFT sequence. The chemical shift values are expressed in ppm scale by reference to internal acetone signal set to 2.225 ppm. Individual monosaccharide residues in the oligosaccharide are referred to by superscripts indicating in the shortest most unambiguous way the glycosidic linkages from the monosaccharide to the reducing end of the glycan.

Mass spectroscopy

Matrix assisted laser desorption ionization mass spectroscopy (MALDI-MS) of the underivatized oligosaccharides was performed with a LASERMAT instrument (Finnigan MAT Ltd., U.K.). Operating conditions and procedures were modeled from the work of Karas (Karas & Hillenkamp, *Anal. Chem.* 60:2299–2301 (1988)). The sample was dissolved in 50 mM 2,5-dihydroxy benzoic acid (in acetonitrile/water 70:30 by volume) and 1 μl of the mixture containing 10–30 pmol of oligosaccharide was applied to a standard stainless steel target. The droplet was allowed to dry in a microcrystalline form before insertion to the instrument. Oligomannose 9 ($Man_9GlcNAc_2$; Mw=1884; source: porcine thyroglobulin) from Oxford Glycosystems, U.K., was used as an external calibrant.

Enzymatic Synthesis of Oligosaccharides

Oligosaccharides representing mono- and oligovalent sialyl Lewis x glycans (sLex) as well as their fucose-free analogues (sialyl LN) for cell adhesion experiments were enzymatically synthesized. The syntheses involved the use of previously generated poly-N-acetyllactosamine backbones (Renkonen, O. et al., *Biochem. Cell Biol.* 68:1032–1036 (1990); Seppo, A. et al., *Biochemistry* 34:4655–4662 (1995)) that were convertcd into mono-, di- and tetravalent sLex glycans 1, 4 and 9 (see Table 2 for structures) by using enzymatic α2,3-sialylation and α1,3-fucosylation reactions. Glycan 9 represents the largest known pure oligosaccharide constructed so far starting effectively from a monosaccharide primer. Like the other synthesis products, it was characterized extensively using a number of techniques including NMR-spectroscopy and mass spectrometry. All fucose residues were transferred to the sialylated rather than to the proximal and "inner" Galβ1-4GlcNAc residues of glycans 3 and 8, as expected (Niemela, R. et al., *Glycoconjugate J.* 12:36–44 (1995)), but one of the four sialylated Galβ1-4GlcNAc units of glycan 8 reacted much more slowly than its companions, leading to the formation of a trifucosyl intermediate (either glycan 10 or 11) in an unexpectedly pure form.

Synthesis of monovalent sLex glycan 1

Glycan 1 was prepared from Galβ1-4GlcNAc by enzymatic α2,3-sialylation followed by enzymatic α1,3-fucosylation essentially as described (de Vries et al., *FEBS Lett.*, 330:243–248 (1993)). The purified product was characterized by $^1$H-nuclear magnetic resonance (NMR) spectroscopy at 500 MHz, and a spectrum identical to those described previously was observed (data not shown) (Ball et al., *J. Am. Chem. Soc.* 114:5449–5451 (1992); de Vries et al., *FEBS Lett.*, 330:243–248 (1993)).

Synthesis of glycan 3

The enzymatic generation of the biantennary glycan 2 has been previously described (Renkonen, O. et al., *Biochem. Cell Biol.* 68:1032–1036 (1990). Here, its distal Galβ1-4GlcNAc units were decorated with terminal α2,3-linked sialic acid. Glycan 2 (100 nmol) was incubated with CMP-NeuNAc and α2,3 sialytransferase present in human placental microsomes, and the resulting mixture was fractionated by anion-exchange HPLC. The fraction (85 nmol) eluting like a disialylated oligosaccharide marker was pooled, lyophilized, desalted by gel filtration and subjected to NMR analysis.

Figure 3A:
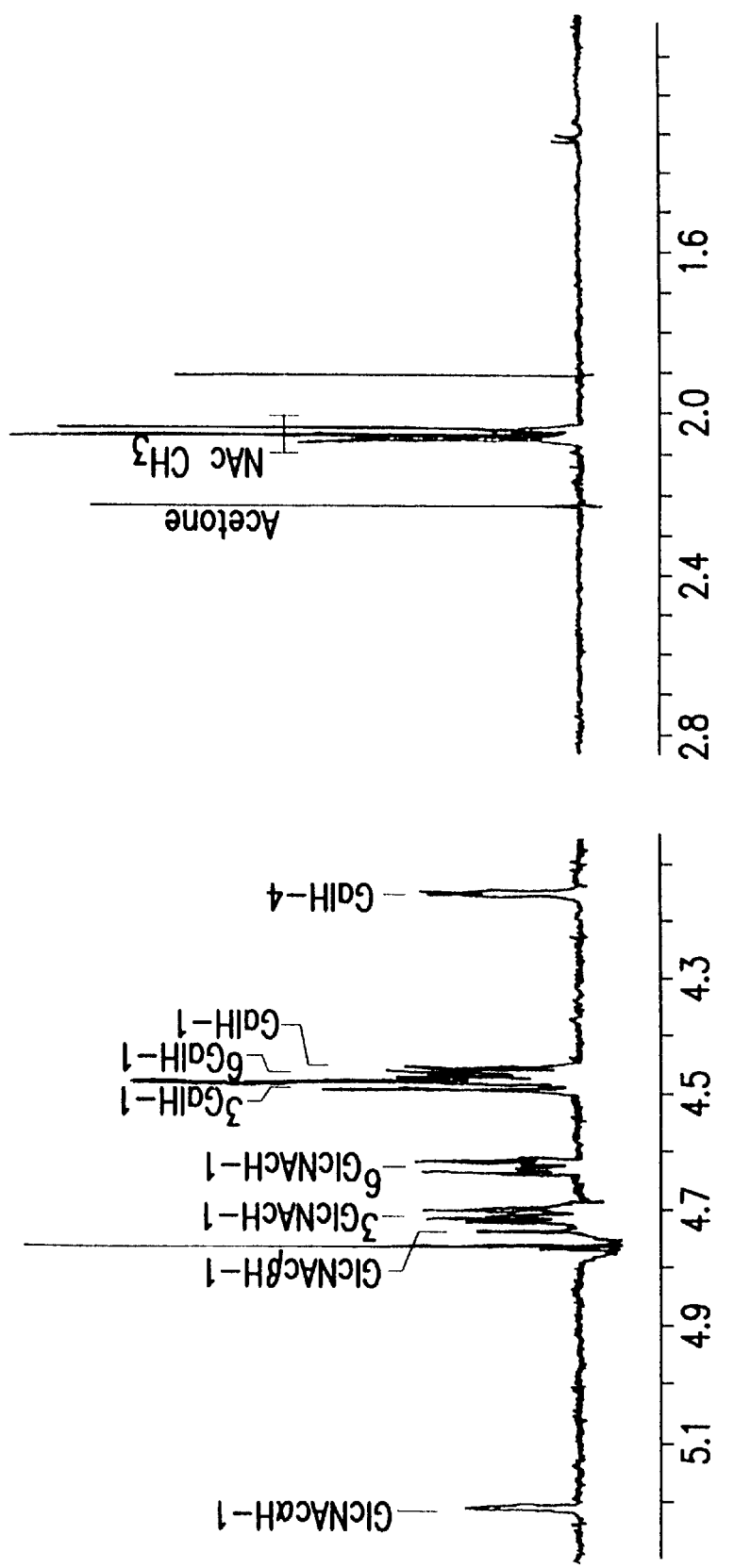
FIG. 3 (panels A–D). Expansions of 500 MHz $^1$H-NMR spectra of diantennary glycans. A) Glycan 2. B) Glycan 3. C) Glycan 4. D) A mixture of glycans 5 and 6. Intensity in the left expansions is twice the intensity of the right ones. HOD and ssb denotes the position of residual water signal and its spinning side band, respectively. Signals marked with an asterisk arise from an impurity present in deuterated water. The indicator lines in the figure are positioned at the chemical shift values of the specified signal multiplets. For exact chemical shift values see Table 3.
Figure 3B:
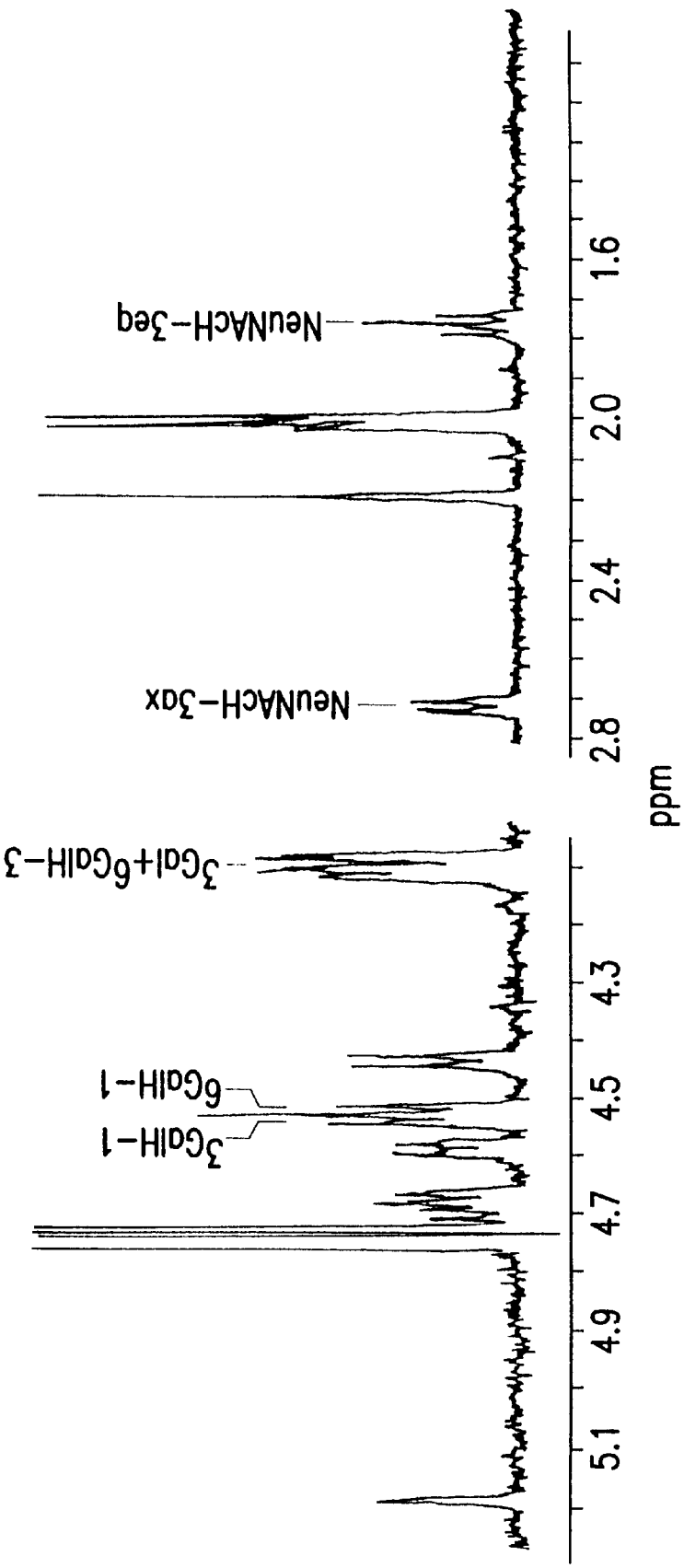
Figure 3D:
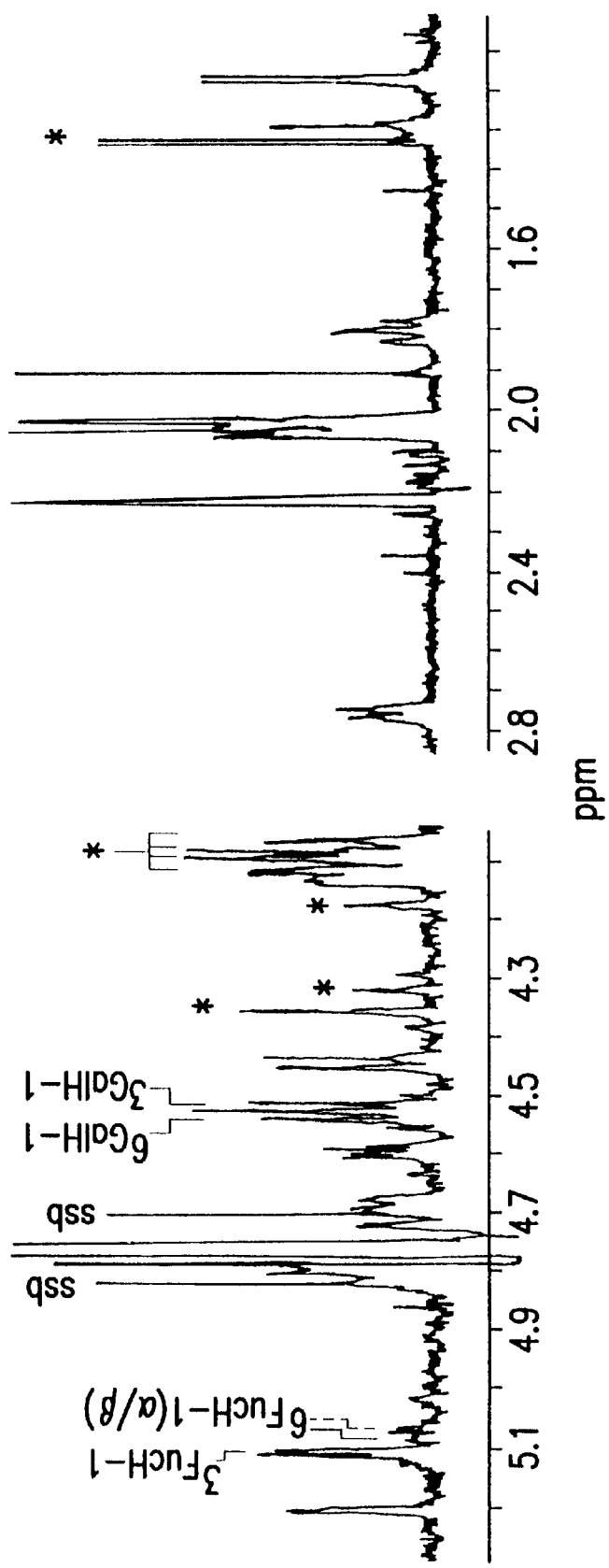

The $^1$H-NMR spectrum of the disialylated product (FIG. 3B, see Table 3 for chemical shift values) shows that it represented glycan 3. In comparison to the spectrum of glycan 2 (FIG. 3A, Table 3) the addition of two NeuNAc's is shown by the appearance of the signals of NeuNAc H-3ax and H-3eq, two equivalents each at 2.757 and 1.799 ppm, respectively (FIG. 3B). The H-1 signals of acceptor residues $^3$Gal and $^6$Gal are shifted downfield +0.081 and +0.079 ppm, respectively, and a new signal of two equivalents appears at 4.117 ppm; it is assigned to H-3's of the α2,3-sialylated galactoses. These reporter group signals are characteristic to α2,3-sialylation of distal galactoses (Vliegenthart, J. F. G. et al., *Adv. Carbohydr. Chem. Biochem.* 41:209–374 (1983); Kamerling & Vliegenthart, *Biol. Magn. Res.* 10:1–287 (1992); Machytka, D. et al., *Carbohydr. Res.* 254:289–294 (1994)).

Synthesis of glycan 4

Figure 4A:
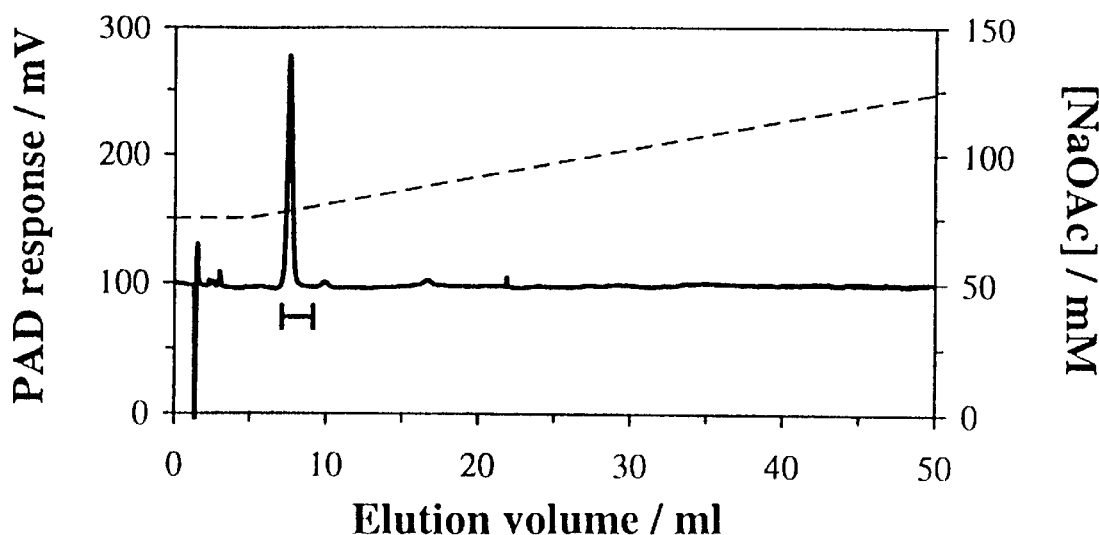
FIG. 4 (panels A–C). Chromatographic analysis of fucosyltransferase products of glycan 3. A) HPAE-PAD chromatography of product from a complete reaction. The bar shows how glycan 4 was collected. PAD response is indicated as a solid line, Na-acetate gradient as a dashed line. B) HPAE-PAD chromatography from a partial reaction. Peaks labeled D1, D2 and D3 represented saccharide 4, a mixture of saccharides 5 and 6, and saccharide 3, respectively. C) Paper chromatography of a concomitant β-galactosidase and β-N-acetylhexosaminidase digest of a mixture of desialylated saccharides 5 and 6. Chromatography was performed with the upper phase of (4:1:5) n-butanol-acetic-water on Whatman III Chromatography paper as described in (Niemela, R. et al., *Glycoconjugate J.* 12:36–44 (1995)). The arrows A and B indicate elution positions of Galβ1-4(Fucα1-3)GlcNAcβ1-6Galβ-4GlcNAc and Galβ1-4(Fucα1-3)GlcNAcβ1-3Galβ-4GlcNAc, respectively.

A sample of glycan 3 (75 nmol) was incubated with GDP-Fuc and human milk α1,3-fucosyltransferase. MonoQ ion-exchange chromatography of the reaction mixture yielded a peak eluting like a disialylated marker oligosaccharide (not shown). This material was subjected to HPAE chromatography, yielding a single major peak (74 nmol, FIG. 4A). This material eluted earlier than the starting material or the monofucosylated product obtained in a partial reaction (see below), indicating that it represented a difucosylated product (Hardy, M. R. & Townsend, R. R., *Proc. Natl. Acad. Sci. USA* 85:3289–3293 (1988)).

The $^1$H-NMR spectrum of the difucosylated product (FIG. 3C, Table 3) showed that two fucoses had been transferred to the acceptor, yielding the glycan 4. The H-1 signals of the fucoses resonated at 5.117 ppm and 4.078($\alpha$)/5.091($\beta$) ppm ($^3$FucH-1 and $^6$FucH-1, respectively). In glycan 4 also the H-1 signals of $^3$Gal and $^6$Gal were shifted (−0.027 and −0.028 ppm, respectively) compared to the corresponding signals in glycan 3. In contrast, the H-1 signal of the branching galactose was practically unaffected, showing that the GlcNAc in the reducing end was not fucosylated. This confirms and extends previous data showing that branch forming Gal$\beta$1-4GlcNAc residues of polylactosamines are not fucosylated under the conditions used (Niemelä et al., *Glycoconjugate J.* 12: 36–44 (1995)).

Synthesis of glycans 5 and 6

Figure 4B:
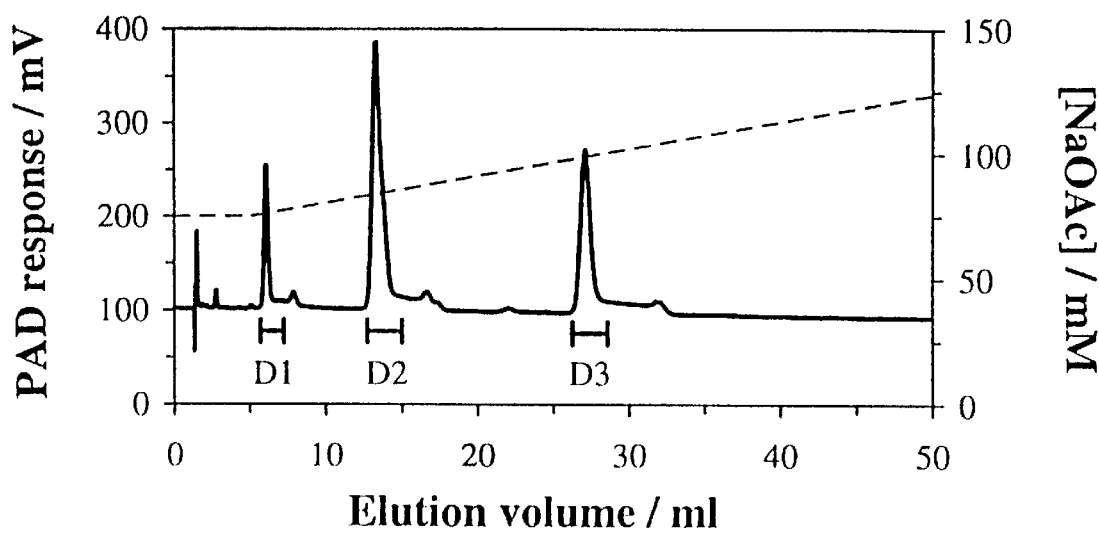
Figure 4C:
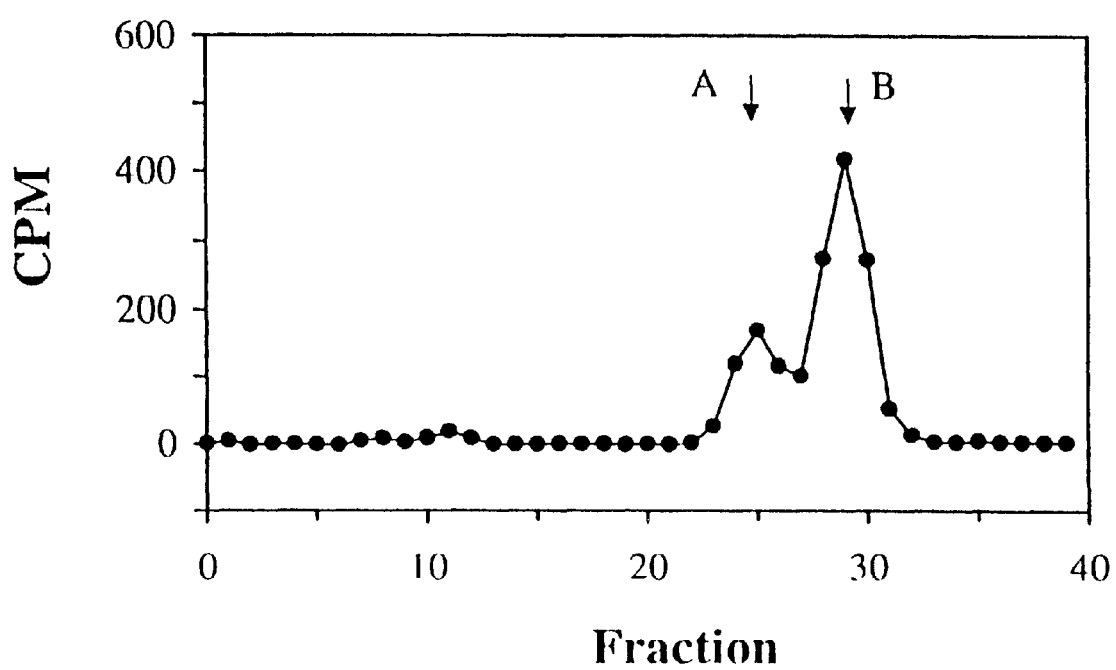

A partial fucosyltransferase reaction with glycan 3 was also performed by limiting the reaction time and the amount of GDP-[$^{14}$C]Fuc donor. HPAE-chromatography of the reaction mixture (FIG. 4B) revealed peaks D1 and D3, which eluted like the difucosylated product 4 and the unreacted acceptor 3, respectively; the intermediate peak D2 represented a mixture of monofucosylated products 5 and 6. To reveal its composition the D2 mixture was desialylated and then incubated with $\beta$-N-acetylglucosaminidase and $\beta$-galactosidase, which eroded the non-fucosylated branches (Kobata, A., *Anal. Biochem.* 100:1–14 (1979)) but left the fucosylated arms intact (i.e. upper branch of desialylated "5" and lower branch of desialylated 6 remained intact). The resulting mixture of isomeric pentasaccharides was finally separated by paper chromatography (FIG. 4C) (Niemelä, R. et al., *Glycoconjugate J.* 12:36–44 (1995)). The data revealed that peak D2 represented a 1:3 mixture of 5 and 6. The NMR-spectrum of Peak D2 showed a strong Fuc H-1 signal at 5.117 ppm and a weak signal at 5.078/5.091 ppm, making possible the unambiguous assignments of the corresponding signals in glycan 4 (Table 3). We have shown previously that besides 3, also the bi-antennary glycan 2 is $\alpha$1,3 fucosylated in a partial reaction preferentially in the 1,3-linked branch under the conditions used (Niemelä, R. et al., *Glycoconjugate J.* 12:36–44 (1995)).

TABLE 3

$^1$H-NMR Chemical shifts[a] of structural reporter group signals of synthetic glycans 2–4 and 6

| Residue[b] | pro-ton | Glycan 2 | Glycan 3 | Glycan 4 | Glycan 6 |
|---|---|---|---|---|---|
| GlcNAc | H-1 | 5.209/4.729 | 5.215/4.726 | 5.215/4.712 | 5.214/4.724 |
| Gal | H-1 | 4.457/4.455 | 4.459 | 4.454 | 4.455 |
|  | H-4 | 4.151 | 4.142 | 4.135 | N.D. |
| $^3$GlcNAc | H-1 | 4.700/4.695 | 4.699/4.695 | 4.706 | 4.708/4.697 |
| $^6$GlcNAc | H-1 | 4.624/4.618 | 4.612/4.606 | 4.607 | 4.612/4.605 |
| $^3$Gal | H-1 | 4.478 | 4.559 | 4.532 | 4.533 |
|  | H-3 | N.D. | 4.117 | 4.088 | N.D. |
| $^6$Gal | H-1 | 4.463/4.467 | 4.544 | 4.516 | 4.545 |
|  | H-3 | N.D. | 4.117 | 4.088 | N.D. |
| $^3$NeuNAc | H-3ax | — | 2.757 | 2.762 | 2.764 |
|  | H-3eq | — | 1.799 | 1.796 | 1.797 |
| $^6$NeuNAc | H-3ax | — | 2.757 | 2.762 | 2.755 |
|  | H-3eq | — | 1.799 | 1.796 | 1.801 |
| $^3$Fuc | H-1 | — | — | 5.117 | 5.117 |
|  | H-5 | — | — | 4.819 | N.D. |
|  | H-6 | — | — | 1.663 | 1.667 |
| $^6$Fuc | H-1 | — | — | 5.078/5.091 | — |
|  | H-5 | — | — | 4.819 | — |
|  | H-6 | — | — | 1.663 | — |

[a] Chemical shifts are given in ppm scale by reference to internal acetone signal set to 2.225 ppm. If two values separated by a slash are given for a resonance, they refer to $\alpha/\beta$ anomers of the molecule in question.
[b] For pinpointing the monosaccharide residues see the materials and methods section.
N.D. Not determined.

Synthesis of glycan 8

The enzymatic generation of the tetra-antennary glycan 7 has been previously described (Seppo, A. et al., *Biochemistry* 34:4655–4662 (1995)); here, its distal Gal$\beta$1-4GlcNAc units were decorated with terminal $\alpha$2,3-NeuNAc residues. A sample of 7 (75 nmol) was incubated with CMP-NeuNAc and $\alpha$2,3 sialyltransferase and then processed as above. Ion exchange chromatography on a MonoQ column (FIG. 5A) gave a minor product eluting like a trisialo-oligosaccharide marker, while the major product (59 nmol) eluted more slowly.

Figure 6A:
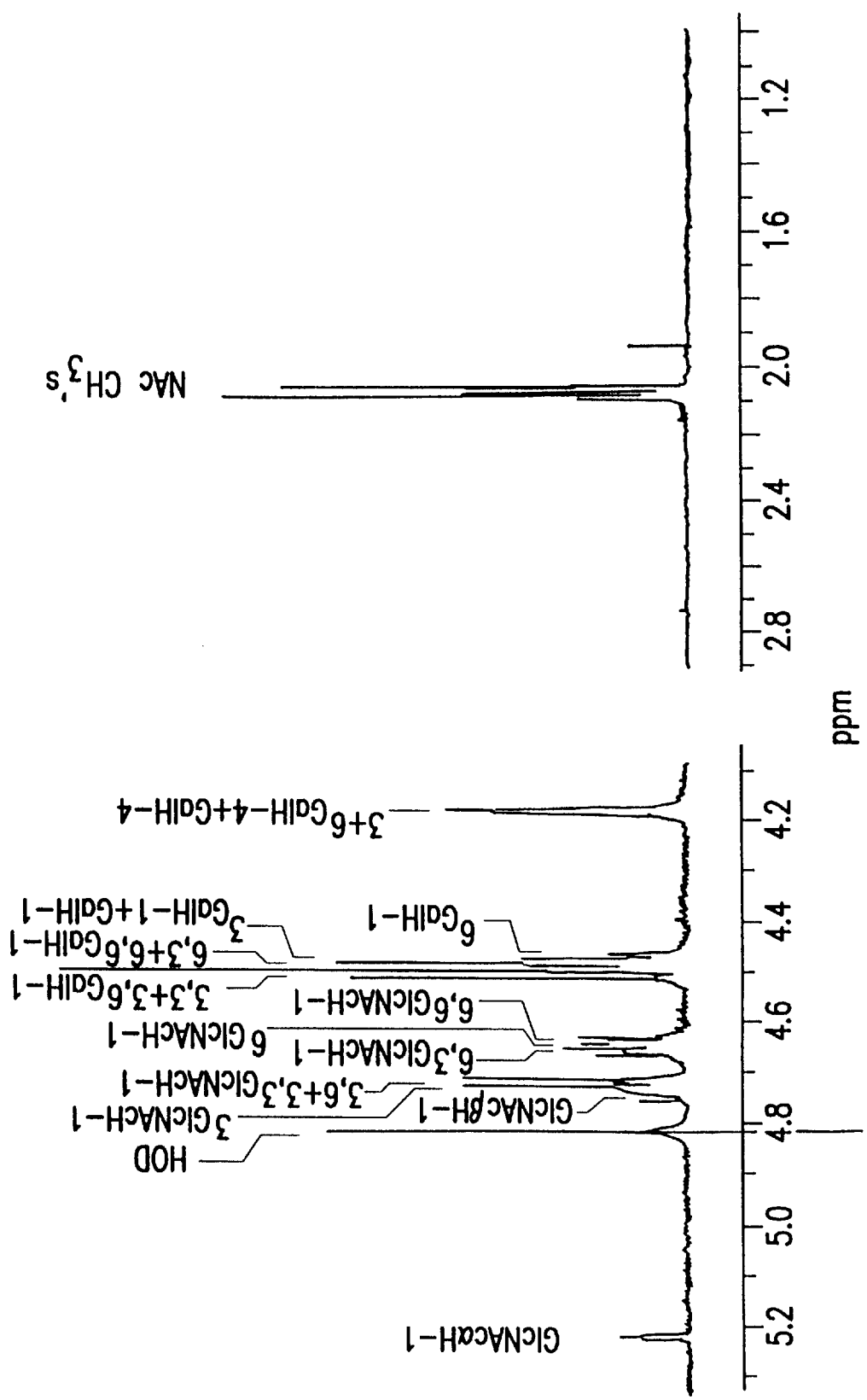
FIG. 6 (panels A–C). Expansions of 500 MHz $^1$H-NMR spectra of tetra-antennary glycans. A) Spectrum of saccharide 7. B) Spectrum of saccharide 8. C) Spectrum of saccharide 9. Signals marked with an asterisk arise from an impurity present in deuterated water. Intensity in the left expansions is twice the intensity in the right expansions. Lines in the figure point to the chemical shift of signal multiplet. For exact chemical shift values see Table 4.
Figure 6B:
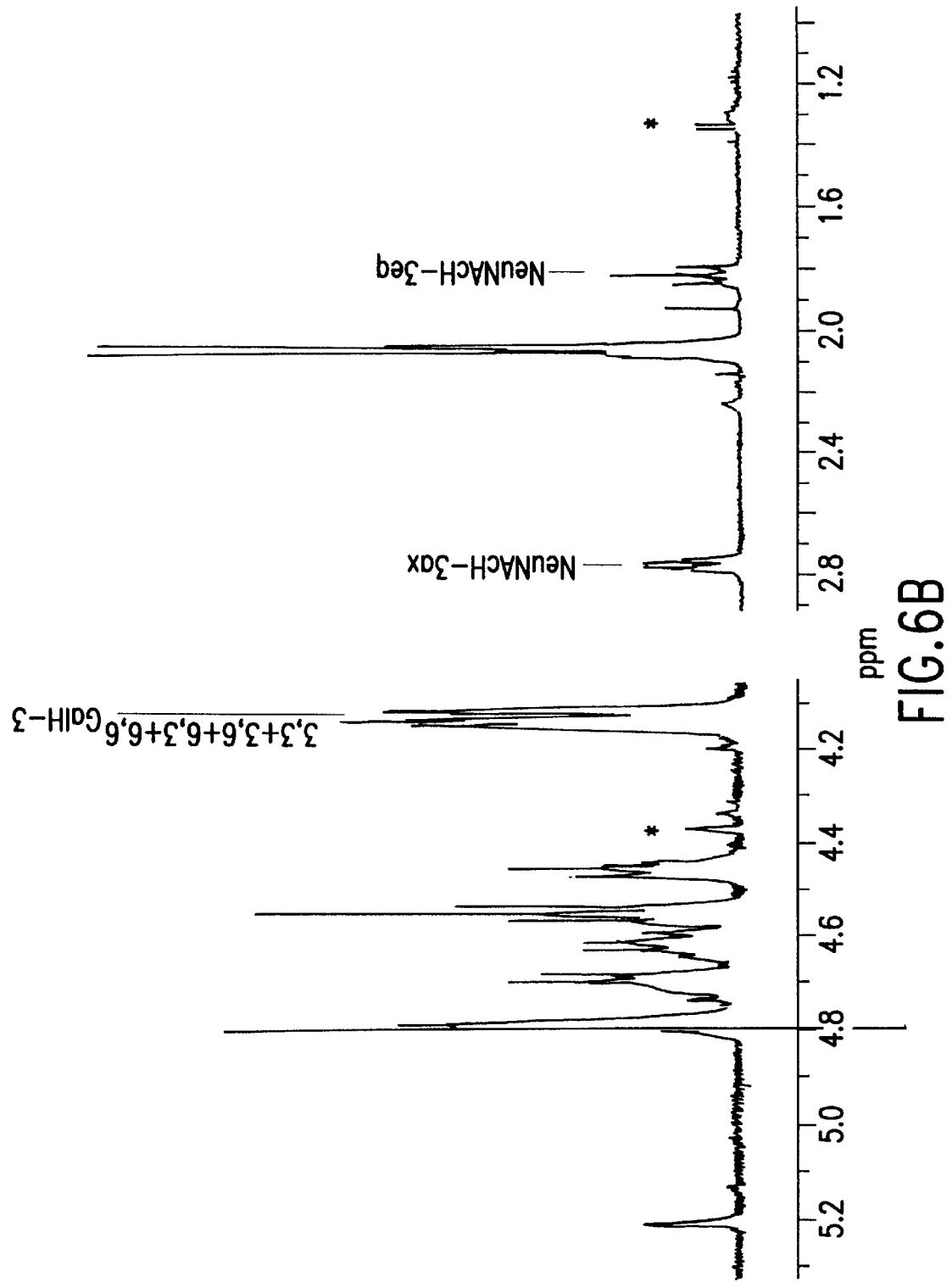

The $^1$H-NMR-spectrum of the major product confirms its identity as compound 8 (FIG. 6B, Table 4). In comparison to a spectrum of the acceptor glycan 7 (FIG. 6A), the spectrum of 8 reveals clearly the transfer of four equivalents of NeuNAc in $\alpha$2,3 linkage. The appearance of NeuNAc H-3ax signal at 1.803 ppm and H-3eq signal at 2.756 ppm, four equivalents both, shows that the newly added NeuNAc residues indeed are in $\alpha$2,3 linkage (Vliegenthart, J. F. G. et al., *Adv. Carbohydr. Chem. Biochem.* 41:209–374 (1983); Kamerling & Vliegenthart, *Biol. Magn. Res.* 10:1–287 (1992); Machytka, D. et al., *Carbohydr. Res.* 254:289–294 (1994)). This notion is supported by the appearance of a four peak pattern at 4.119 ppm which can be assigned to H-3s of the penultimate galactoses. Characteristically, the H-1 signals of the penultimate galactoses are also shifted downfield +0.080 ppm as in 3, pinpointing the acceptor sites in the molecules.

TABLE 4

$^1$H-NMR Chemical shifts[a] of structural reporter group signals of synthetic glycans 7–9.

| Residue[b] | proton | Glycan 7[c] | Glycan 8 | Glycan 9 |
|---|---|---|---|---|
| GlcNAc | H-1 | 5.207/4.725 | 5.210/4.725 | 5.210/4.727 |
| Gal | H-1 | 4.459 | 4.460 | 4.456 |
| $^3$GlcNAc | H-1 | 4.705 | 4.703 | 4.709 |
| $^6$GlcNAc | H-1 | 4.626 | 4.620[d] | 4.623[e] |
| $^3$Gal | H-1 | 4.459 | 4.460 | 4.456 |
| $^6$Gal | H-1 | 4.445 | 4.445 | 4.440 |

TABLE 4-continued $^1$H-NMR Chemical shifts$^a$ of structural reporter group signals of synthetic glycans 7–9.

| | | Glycan | | |
|---|---|---|---|---|
| Residue$^b$ | proton | 7$^c$ | 8 | 9 |
| $^{3,3}$ + $^{3,6}$GlcNAc | H-1 | 4.697 | 4.689 | 4.695 |
| $^{6,3}$GlcNAc | H-1 | 4.638 | 4.620$^d$ | 4.604$^e$ |
| $^{6,6}$GlcNAc | H-1 | 4.614 | 4.598$^d$ | 4.556$^e$ |
| $^{3,3}$ + $^{3,6}$Gal | H-1 | 4.480 | 4.559 | 4.534 |
| | H-3 | N.D. | 4.119 | 4.089 |
| $^{6,3}$ + $^{6,6}$Gal | H-1 | 4.464 | 4.544 | 4.517 |
| | H-3 | N.D. | 4.119 | 4.089 |
| NeuNAc | H-3ax | — | 2.756 | 2.762 |
| | H-3eq | — | 1.803 | 1.798 |
| $^{3,3}$ + $^{3,6}$Fuc | H-1 | — | — | 5.118 |
| | H-6 | — | — | 1.668 |
| $^{6,6}$ + $^{6,3}$Fuc | H-1 | — | — | 5.084 |
| | | | 5.077$^f$ | |
| | H-6 | — | — | 1.668 |

$^{a)}$Chemical shifts are given in ppm scale by reference to internal acetone signal set to 2.225 ppm. If two values for a resonance are given, they refer to α/β anomers of the molecule in question, respectively
$^{b)}$Pinpointing the monosaccharide residues see the materials and methods section.
$^{c)}$Data from (27).
$^{d,e)}$Assignments may have to be exchanged.
$^{f)6,6}$FucH-1 and $^{6,3}$FucH-1 signals could not be assigned individually.
N.D. Not determined.

Sythesis of glycan 9

Glycan 8 was incubated with GDP-Fuc and α1,3 fucosyltransferase from human milk. The reaction mixture was fractionated by HPAE-chromatography (FIG. 5B) and two major peaks eluting earlier than the starting material were obtained. Peak T1 proved to be the tetrasialo-tetrafucoglycan 9 whereas peak T2 represented an almost pure single isomer of tetrasialo-trifuco-glycans. The minor peak T3 is believed to be a mixture of tetrasialo-difuco-glycans.

The T1 glycan was desialylated with sialidase from *A. ureafaciens* and then subjected to concomitant β-galactosidase and β-N-acetylhexosaminidase treatments. Subsequent gel filtration followed by HPAE-chromatography revealed that desialylated T1 had remained intact. These data established that four fucoses were present in T1, linked to the sialylated Galβ1-4GlcNAc units at the non-reducing ends of the acceptor glycan 8. Hence T1 saccharide represented glycan 9.

Figure 6C:
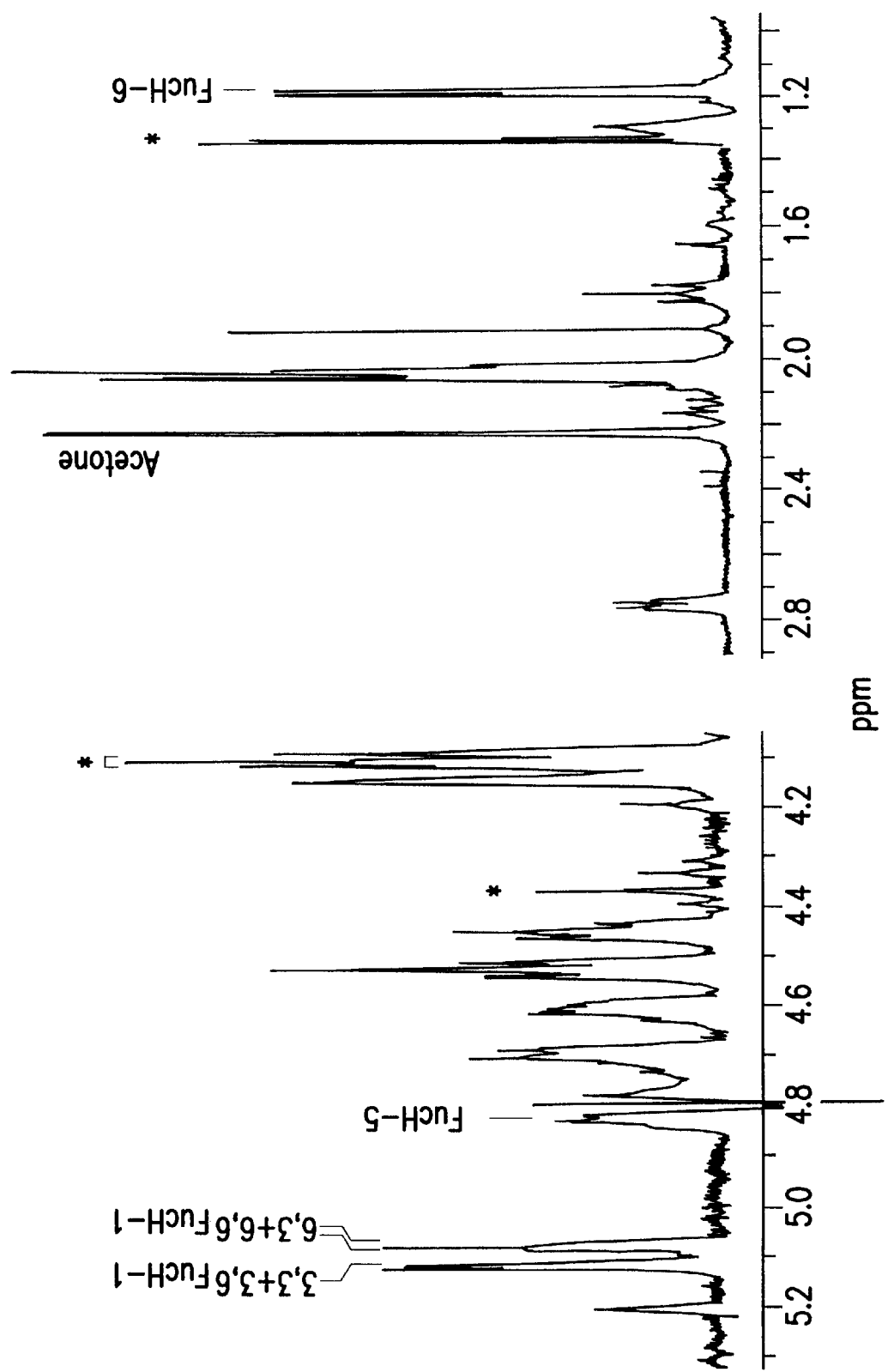

$^1$H-NMR-spectrum of T1 saccharide (FIG. 6C; Table 4) confirms that the four α-linked fucoses were present. This can be seen as four Fuc H-1 signals at 5.119 ppm (two equivalents), 5.084 ppm and 5.076 ppm (one equivalent each), respectively, and as a Fuc H-6 signal at 1.668 ppm (12 equivalents). The Fuc H-5 signal at around 4.81 ppm cannot be precisely positioned and measured due to the severe overlap with the residual HDO peak. Among the H-1 signals of galactoses in 8, only those of the penultimate, sialylated residues were shifted upon fucosylation. These shifts (−0.025 ppm for $^{3,3}$Gal+$^{3,6}$Gal and −0.027 ppm for $^{6,3}$Gal+$^{6,6}$Gal) confirm that fucosylation and sialylation had occurred solely at the distal Galβ1-4GlcNAc units of 7. We did not detect any signs of α2,6-bonded NeuNac in 8 or 9. Even if small amounts of α2,6-NeuNAc in 8 had escaped our NMR-analysis, they would have been eliminated from the tetrafucosyl gylcan 9 because of their inability to become fucosylated (Paulson, J. C. et al., *J. Biol. Chem.* 253:5617–5624 (1978)).

Characterization of the synthetic glycan representing 10 or 11

Most of the T2 material (FIG. 6C, Table 4) represented a single isomer where Fuc was missing at a single distal branch but was present at the three others. In comparison to the spectrum of glycan 9 the Fuc H-1 signal at 5.084 ppm was very strongly reduced in T2 saccharide. In glycan 9 this signal is assigned to H-1 of the fucose linked either to $^{6,6}$GlcNAc or $^{6,3}$GlcNAc. Accordingly, the T2 saccharide represents either glycan 10 or glycan 11 in almost pure form.

Figure 7A:
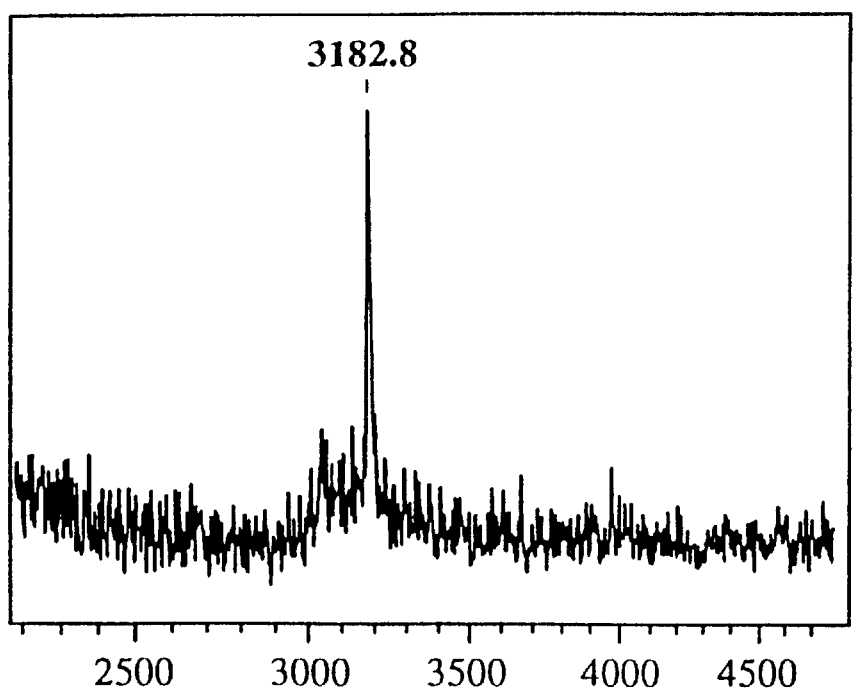
FIG. 7 (panels A–B). Mass spectroscopy (MALDI-MS) of desialylated tetra-antennary oligosaccharides. A) Mass spectrum of desialylated saccharide from peak T1, FIG. 5B B) Mass spectrum of desialylated saccharide from peak T2, FIG. 5B.
Figure 7B:
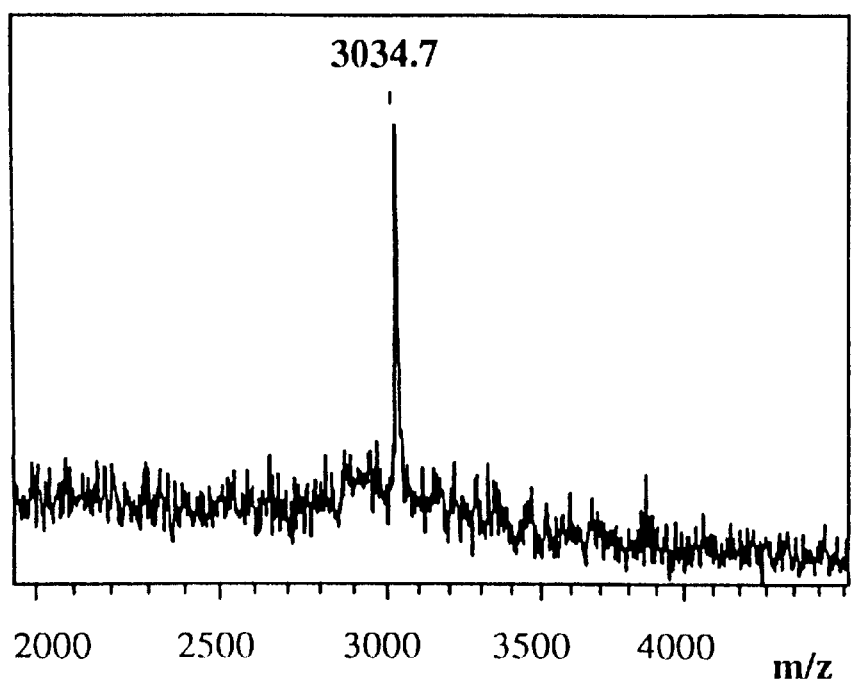

The number of Fuc residues in desialylated T1 and T2 saccharides was confirmed by matrix assisted laser desorption mass spectrometry (MALDI-MS). Desialylated T1 saccharide (FIG. 7A) revealed a single peak with m/z=3183 Da (calculated for [Fuc$_4$Hex$_7$HexNAc$_7$+NA$^+$] 3183 Da) whereas desialylated T2 saccharide (FIG. 7B) revealed a single peak with m/z=3035 Da (calculated for [Fuc$_3$Hex$_7$HexNA$_{c7}$+Na$^+$] 3035 Da).

Example 3

All Enzymatically Synthesized Sialyl Lewis x-type Oligosaccharides Inhibit Lymphocyte Adhesion to Endothelium of Rejecting Cardiac Transplants.

Heart transplant rejection is characterized by a heavy infiltration of lymphocytes into the graft (Renkonen, R. et al., *Cell Immunol.* 77:188–195 (1983); Häyry, P. et al., *Immunol. Rev.* 77:85–142 (1984); Turunen, J. P. et al., *Transplantation* 54:1053–1058 (1992)). This application shows that cardiac endothelium, which does not express sLea and sLex in normal animals, can be induced to express these oligosaccharide epitopes during transplant rejection episodes. This de novo expression of sialylated Lewis oligosaccharides leads to enhanced lymphocyte adhesion to endothelium in a sLea-, sLex- and L-selectin-dependent manner. The endothelium of rejected heart grafts, but not that of normal hearts or syngeneic grafts, stains directly with the L-selectin-IgG fusion protein.

Figure 1G:
FIG. 1 (panels A–L). Binding of lymphocytes to endothelial structures in normal and transplanted heart tissue in the Stamper-Woodruff assay. The microphotographs have been taken so that the lymphocytes (round and black) are in focus and the underlying (gray) tissue is slightly out-of focus. Bound lymphocytes are marked by small black arrows. Panel (A) shows that only very few lymphocytes are bound to endocardium of normal hearts. In the (B) syngeneic grafts as well as in (C) allograft the number of bound lymphocytes is also at a very low level. The same observation was done in arterioles; these structures in (D) normal hearts practically did not adhere lymphocytes at all and the binding in (E) syngeneic grafts and (F) allografts was at a very low level. Venules (marked by a dashed line) from (G) normal hearts and (H) syngeneic grafts adhered only a few lymphocytes but, on the contrary, the venules in the (I) allografts adhered an increased number of lymphocytes. Intermuscular capillaries adhered some lymphocytes in (J) the normal tissue as well as in (K) the syngeneic grafts. Panel (L) shows that there was a clear enhancement in the lymphocyte adherence to intramuscular capillaries in the allografts. A large number of cross and longitudinal sections of intermuscular capillaries are seen in this panel and only a few of the lymphocytes adhering to these structures are marked by arrows. Note that in all panels there are also some lymphocytes adhering directly on top of the myocardium and are not lying on top of any endothelial structures (marked by white arrows in panels A and L).
Figure 1H:
Figure 1I:
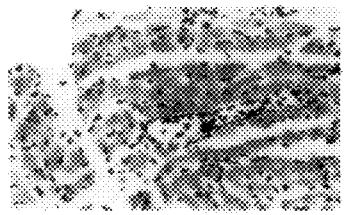
Figure 1J:
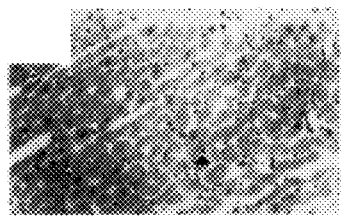
Figure 1K:
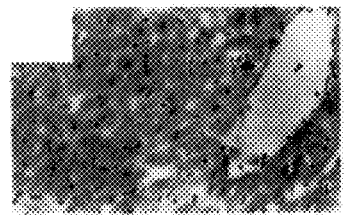
Figure 1L:
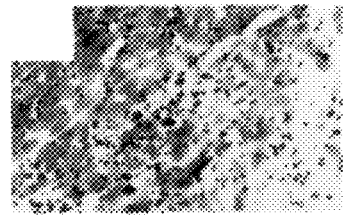
Figure 2:
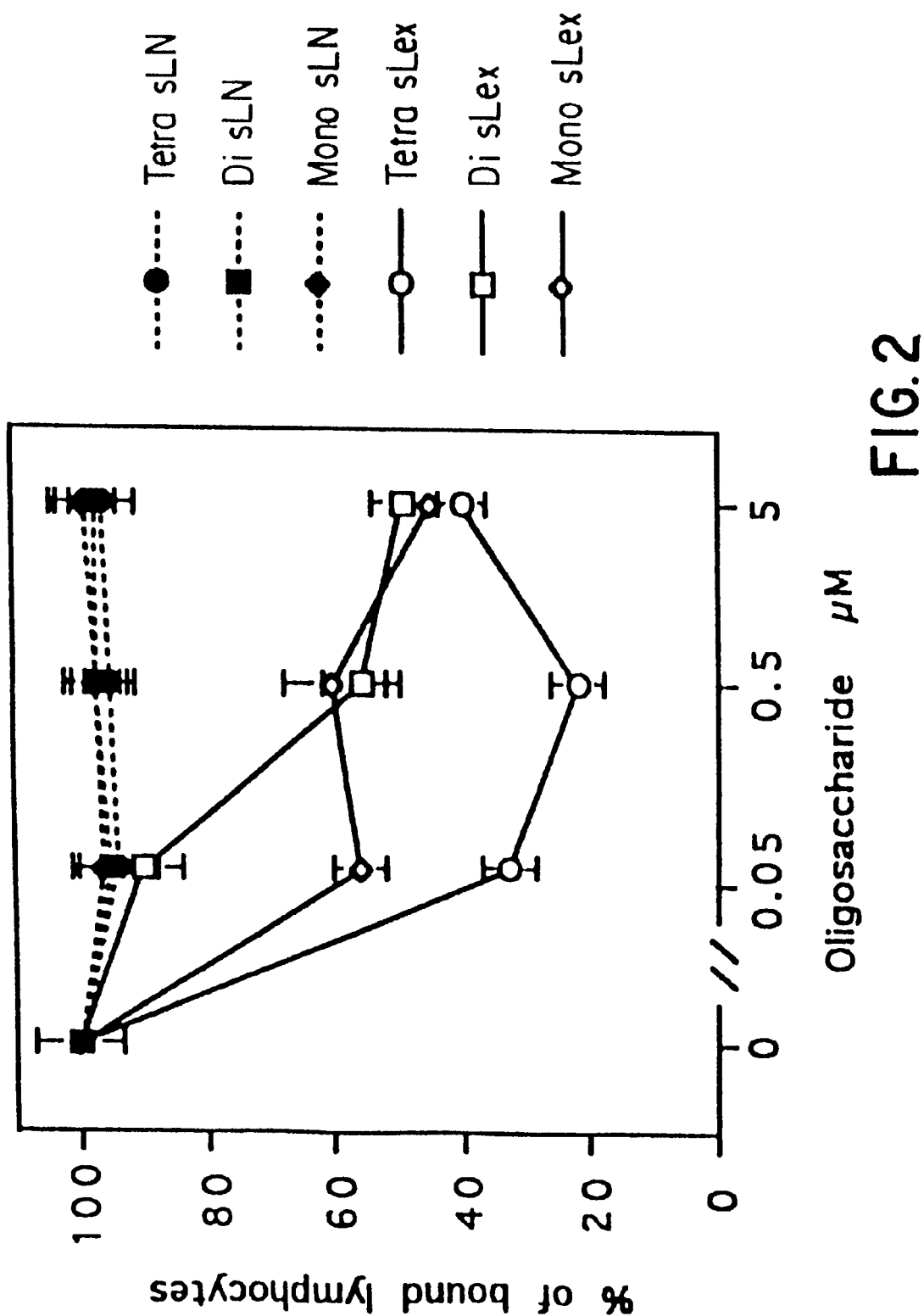
FIG. 2. Effect of various enzymatically synthesized branched oligosaccharide constructs on lymphocyte adhesion to allograft endothelium. While all the oligosaccharides in the sLe$^x$ family reduced lymphocyte binding, the inhibitory capacity of tetravalent sLe$^x$ was significantly superior to other sLe$^x$-oligosaccharides. All the sLN's lacking fucose were without effect. The mean±SEM of one representative experiment out of three is presented.

The inhibition of lymphocyte adhesion to cardiac endothelium during acute rejection episodes by oligosaccharides was examined using the family of oligosaccharides synthesized by enzyme-aided synthesis in Example 2: monovalent sLex tetrasaccharide (1), divalent sLex decasaccharide (4) and tetravalent sLex 22-meric oligosaccharide (9) and their non-fucosylated sialyl lactosamine analogues (3, 8). The lymphocytes were preincubated for 30 min with various concentrations of the oligosaccharides and placed thereafter into the Stamper-Woodruff binding assay without further washings. These oligosaccharides did not significantly alter the lymphocyte binding to syngeneic grafts which was only slightly above the binding to normal heart tissue (Table 1 and data not shown). On the other hand, all members of the sLex-family were effective in inhibiting lymphocyte adhesion to cardiac endothelium, but the tetravalent sLex was clearly superior compared to the other sLex oligosaccharides (FIG. 2). Concomitantly the non-fucosylated sialyl-lactosamine glycans were without effect.

The results show that the tetravalent sLex (a 22-meric oligosaccharide) is superior in inhibiting the L-selectin-dependent lymphocyte adhesion to heart endothelium compared to di- or monovalent sLex oligosaccharides (deca- and tetramers, respectively). On the contrary, the sLN oligosaccharides did not have any effect on lymphocyte adhesion. Taken together these data show that the upregulation of the endothelial expression of sLea and sLex is of crucial importance in the generation of L-selectin dependent lymphocyte inflammation in the rejecting cardiac allograft, and that oligosaccharides can inhibit this process.

Example 4
Multivalent sLex-oligosaccharides are High-affinity Inhibitors of Lymphocyte Adhesion (Bolded numbering corresponds to glycan structures in Table 2)

Using the animal model described in Example 1, kidney grafts were removed at day 3 after transplantation when they were undergoing acute rejection. The lymphocytes were, or were not, pretreated for 30 min with various oligosaccharide constructs and added to the Stamper-Woodruff binding assay. After a 30 min binding assay the loose cells were washed away and the number of bound cells were determined. As can be seen from FIG. 8 all α2,3-sialic acid- and α1,3-fucose-containing polylactosamines (i.e. mono-, di- and tetravalent sLex, structures 1, 4 and 9 respectively) were able to inhibit the lymphocyte binding to PTCE significantly. Lymphocyte adhesion decreased 39% with 0.5 $\mu$M monovalent sLex (1), and the $IC_{50}$ values for di- and tetravalent sLex (4 and 9) were 1.0 $\mu$M and <0.05 $\mu$M respectively. At the most effective concentration used, the glycan 9 inhibited lymphocyte adhesion up to 73%, which is slightly better than the 60% inhibition obtained in this same assay with a functionally active anti L-selectin antibody HRL-1 (Turunen, J. et al., Eur. J. Immunol. 24:1130–1136 (1994)).

None of the fucose-free structures, i.e. sialyllactosamine, and glycans 3 and 8, nor the non-functional anti L-selectin antibody inhibited the lymphocyte adhesion, indicating the crucial role of fucose in this assay. Clearly the tetravalent glycan 9 was the most potent inhibitor, suggesting that it might bind to several L-selectin molecules on the lymphocyte surface.

It has previously been shown that this assay measures mainly L-selectin dependent adhesion. The α1,3-linked fucosyl residues represent an essential structural feature in the inhibitory saccharides in the binding assay. This is characteristic also to the oligosaccharides capable of L-selectin binding (Foxall, C. et al., J. Cell Biol. 117:895–902 (1992); Imai, Y. et al., Glycobiology 2:373–381 (1992)). Even though one cannot exclude the role of E- and P-selectin-dependent adhesion in this assay, it is not likely to occur, since the lymphocytes used were sLex negative.

Among the synthetic sLex glycans, the tetravalent 9 was clearly the most potent inhibitor of lymphocyte adhesion ($IC_{50}$<50 nM). The dose range of the sLex-glycans used in this study was 1000-fold lower than the ones reported in the literature for monovalent sLex and recombinant selectins fixed on microtiter plates (Foxall, C. et al., J. Cell Biol. 117:895–902 (1992)). Probably the two assays used (Stamper-Woodruff and fixed recombinant selectins on plates) can not be directly compared since the binding forces are so different (Varki, A., Proc. Natl. Acad. Sci. 91:7390–7397 (1994)).

The high affinity of glycan 9 for L-selectin is very likely generated by the multiplicity of the binding sLex epitopes. This raises the possibility that one molecule of 9 may bind in the Stamper-Woodruff assay to several carbohydrate recognition domains (CRDs) of L-selectin on lymphocyte surface. The crosslinking of L-selectin CRDs on the cell surface may take place regardless of the monomer-oligomer status of the protein. Even monomeric receptors immobilized by interaction with other surface constituents may become crosslinked on cell surface with individual hemagglutinin trimers in intact influenza viruses by bivalent sialosides (Glick, G. D. et al., J. Biol. Chem. 266:23660–23669 (1991)).

Of potential importance is also the length of the saccharide chains linking the sLex determinants together in glycan 9. The sLex epitopes in 9 are interlinked by chains consisting of as many as five monosaccharide units. In addition, all of these chains contain at least one GlcNAcβ1-6Gal bond lending them extra length and flexibility. It is conceivable that the long and flexible saccharide chain spacers joining the binding epitopes enhance the possibility of multisite binding of 9, leading to crosslinking of lectin domains of L-selectin.

Figure 8:
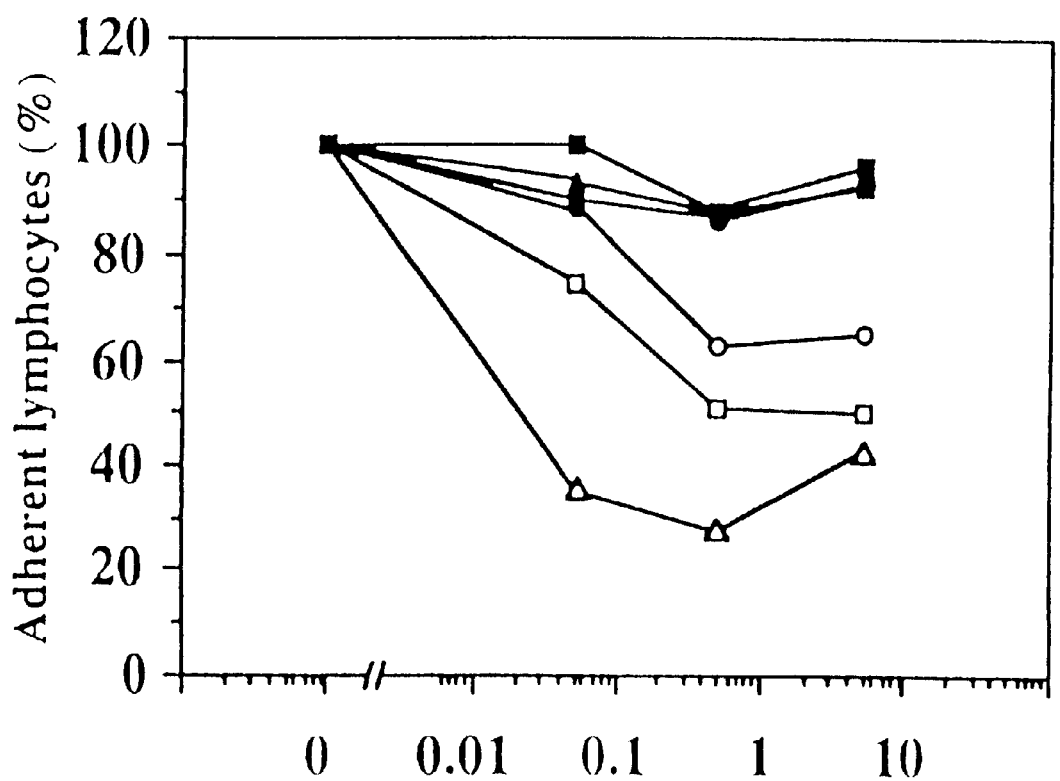
FIG. 8. Effect of enzymatically synthesized sLex (open symbols) and sLN (closed symbols) oligosaccharides on the lymphocyte adhesion to renal graft endothelium. Open circle (○) mono SLe$^x$ (glycan 1), closed circle (●) mono sLN, open square (□) di SLe$^x$ (glycan 4), closed square (■) di sLN (glycan 5), open triangle (Δ) tetra sLe$^x$ (glycan 9), closed triangle (▲) tetra sLN (glycan 8). The lymphocyte-blocking capacity of tetravalent sLe$^x$ was clearly superior to other sLe$^x$-oligosaccharides. The mean of three experiments is presented, the SEM never exceeded 10%; for clarity it is not marked.

A consistent enhancement in the inhibitory efficiency of 9 was observed when the 5 $\mu$M primary solution was diluted (FIGS. 2 and 8). This suggests that at 5 $\mu$M the abundant tetravalent ligand might bind to the L-selectin molecules mostly in a monovalent manner, whereas the probability of multisite binding of 9 increased upon dilution of the ligand. Whether representing true or "functional" oligomers (e.g. monomers that are interconnected by other cell surface constituents), L-selectin appears to be less available for PTCE binding in the state involving multivalently bound inhibitors than univalently bound ligands. There are several examples of multivalent saccharide ligands that possess particularly high affinities for the appropriate membrane-bound lectins. The classical work of Lee et al. (Lee, R. T. et al., Biochemistry 23:4255–4261 (1984); Lee, R. T. et al., Biochemistry 28:8351–8358 (1989)) showed that oligomeric lectins bind multivalent saccharide ligands with a particularly high affinity. It has been shown elsewhere that a tetravalent oligosaccharide containing four distal Galα1-3Gal residues efficiently inhibits mouse sperm adhesion to eggs, while the analogous monovalent pentasaccharide Galα1-3Galβ1-4GlcNAcβ1-3Galβ1-4GlcNAc does not (Litscher, E. et al., Biochemistry 34:4662- (1995)). It has also been observed that oligovalent sLex ligands of E-selectin are better adhesion inhibitors than monovalent sLex (DeFrees, S. A. et al., J. Am. Chem. Soc. 115:7549–7550 (1993); Welply, J. K. et al., Glycobiol 4:259–265 (1994)), but so far the present work is the first demonstration of enhanced potency of multivalent ligands in inhibiting lymphocyte adhesion in a L-selectin-dependent model system.

The synthetic glycan 9 inhibited L-selectin mediated cell adhesion in the Stamper-Woodruff binding assay of the present experiments in remarkably low concentrations. Data from in vivo injection experiments with rats and cats have also demonstrated the value of low concentrations of sLex in inhibiting short-term P-selectin mediated inflammation (Mulligan, M. S. et al., J. Exp. Med. 178:623–631 (1993); Mulligan, M. S. et al., Nature 364:149–151 (1993); Buerke, M. et al. J. Clin. Invest. 93:1140–1148 (1994)). Even long-term (48 h) inflammatory responses can be inhibited by continuous infusion of anti L-selectin mAb to animals. Interestingly, these animals did not generate alterations in the differential count of peripheral blood leukocytes (Arbones, M. L. et al., Immunity 1:247–260 (1994); Pizcueta & Luscinskas, Am. J. Pathol. 145:461–469 (1994)).

The enzymatic synthesis of the oligosaccharides (glycan 9 and glycan 17) described in Examples 2 and 6, respectively, represents the largest pure glycans so far synthesized starting from monosaccharides. Moreover, glycan 9, a tetravalent, tetra-antennary sLex is a superior inhibitor of lymphocyte adhesion to endothelium in a model which is for the major part L-selectin-dependent, suggesting that L-selectin might act as a "functional oligomer" on lymphocyte surface.

The dose range of the monovalent sLex-glycan used in this study was 1000-fold lower than the one reported for inhibition of the binding between soluble recombinant L-selectin and immobilized sLex glycolipids (Foxall, C. et al., *J. Cell Biol.* 117:895–902 (1992)). Obviously, the data of the two assays cannot be directly compared (Varki, A., *Proc. Natl. Acad. Sci.* 91:7390–7397 (1994). Interestingly, Stamper-Woodruff data obtained in binding experiments performed with lymphocytes and rejecting rat heart endothelium (Turunen, J. P. et al., *J. Exp. Med.* 182(4):1133–1141 (1995)) with the saccharides 1, 4 and 9 were quite similar to the present ones. The similarity probably reflects decisive interactions between the saccharides and L-selectin on lymphocyte surface in both sets of experiments.

Data from in vivo injection experiments with rats and cats have also demonstrated the value of low concentrations of monovalent sLex in inhibiting short-term P-selectin mediated inflammation (Buerke, M. et al., *J. Clin. Inv.* 93:1140–1148, (1994); Mulligan, M. S. et al., *J. Exp. Med.* 178:623–631 (1993); Mulligan M. S. et al., *Nature* 364:149–151 (1993)). Even long-term (48 h) inflammatory responses can be inhibited by continuous infusion of anti L-selectin mAb to animals. Interestingly, neither these animals nor L-selectin knockout mice generated alterations in the differential count of peripheral blood leukocytes (Arbones, M. L. et al., *Immunity*, 1:247–260 (1994); Pizcueta and Luscinskas, *Am. J. Pathol.*, 145:461–469 (1994)).

Example 5
Treatment of a Patient with sLEX

A patient diagnosed with an inflammatory condition is treated with a composition comprising a multivalent sLex, e.g. the tetravalent sLex 22-saccharide. The composition is in a pharmaceutically acceptable excipient at a sufficient dose to block lymphocyte binding to the correspondent oligosaccharides on the endothelial cell surface. The composition is given in a regime such that a serum concentration is achieved in about the nanomolar to micromolar range until the condition is sufficiently ameliorated.

When administered to the patient, the composition is formulated in any manner which makes it suitable for oral, parenteral, nasal, enteric or rectal administration with a pharmaceutically acceptable excipient or vehicle, e.g., isotonic saline, in accordance with conventional pharmaceutical practice. The dosage level of the reagent is sufficient to provide an anti-inflammatory effect by the blocking of selectin-mediated, and especially L-selectin-mediated, adhesion events in the patient.

The composition and method of the invention are suitable for treating any condition involving a selectin, and especially an L-selectin-mediated adhesion increased inflammatory reaction. Thus, the reagent is useful for treating such conditions as tissue rejection, arthritis, an infection, especially local infections, dermatoses, inflammatory bowel diseases, autoimmune diseases, etc.

By an "efficacious level" of a composition of the invention is meant a level at which some relief is afforded to the patient who is the recipient of the treatment. By an "abnormal" host inflammatory condition is meant a level of inflammation in the subject at a site which exceeds the norm for the healthy medical state of the subject, or exceeds a desired level. By "secondary" tissue damage or toxic effects is meant the tissue damage or toxic effects which occurs to otherwise healthy tissues, organs, and the cells therein, due to the presence of excessive selectin, and especially L-selectin, adhesion events, including as a result of a "primary" stimulus elsewhere in the body.

Infusion of the compositions of the invention into a patient is thought to result in a lessening of the ability of selectin-expressing leukocytes to "roll" and thus attach to the endothelium, thus preventing or inhibiting adherence of such cells to the site of the inflammation and the localized damage to the endothelium, and thus preventing undesired lymphocyte trafficking or influx into the affected tissues or cells.

Accordingly, the pharmaceutical compositions of the invention are administered in amounts sufficient to antagonize (fully or partially) the patient's native selectin, and especially L-selectin, binding to biological targets of such selectin in such patient, and specifically to endothelial cells.

Amounts and regimens for the administration of selectin-binding carbohydrates and compositions of the invention can be determined readily by those with ordinary skill in the clinical art of treating inflammation-related disorders such as arthritis, tissue injury and tissue rejection. Generally, the dosage of the composition of the invention will vary depending upon considerations such as: type of synthetic carbohydrate employed; age; health; medical conditions being treated; kind of concurrent treatment, if any, frequency of treatment and the nature of the effect desired; extent of tissue damage; gender; duration of the symptoms; and, counterindications, if any, and other variables to be adjusted by the individual physician. A desired dosage can be administered in one or more applications to obtain the desired results.

Figure 9A:
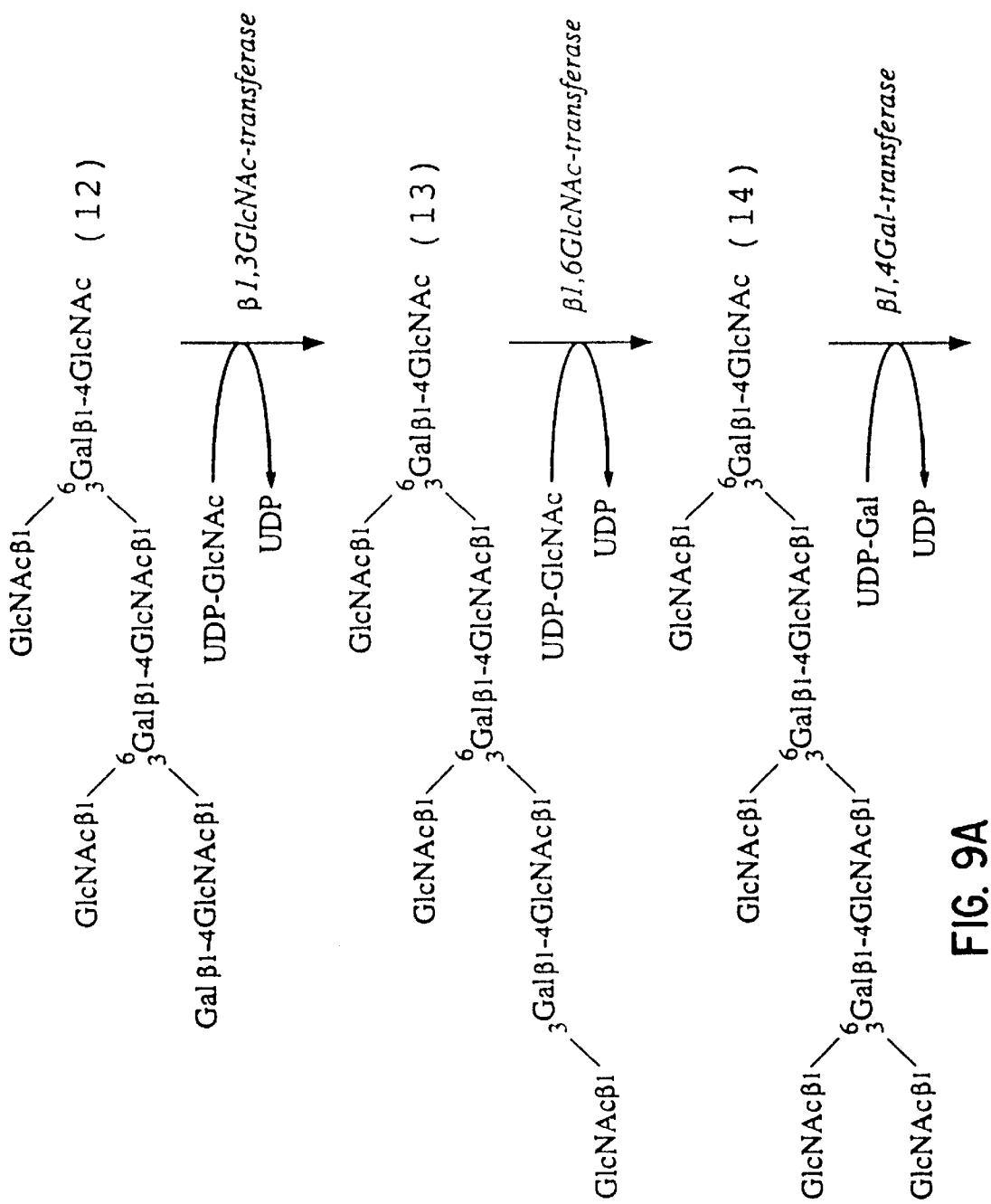
FIG. 9. Outline of the synthesis route from glycan 12 to the tetravalent sialyl Lewis x saccharide 17 of a linear backbone, and further to the sialyl Lewis x saccharide 18.
Figure 9B:
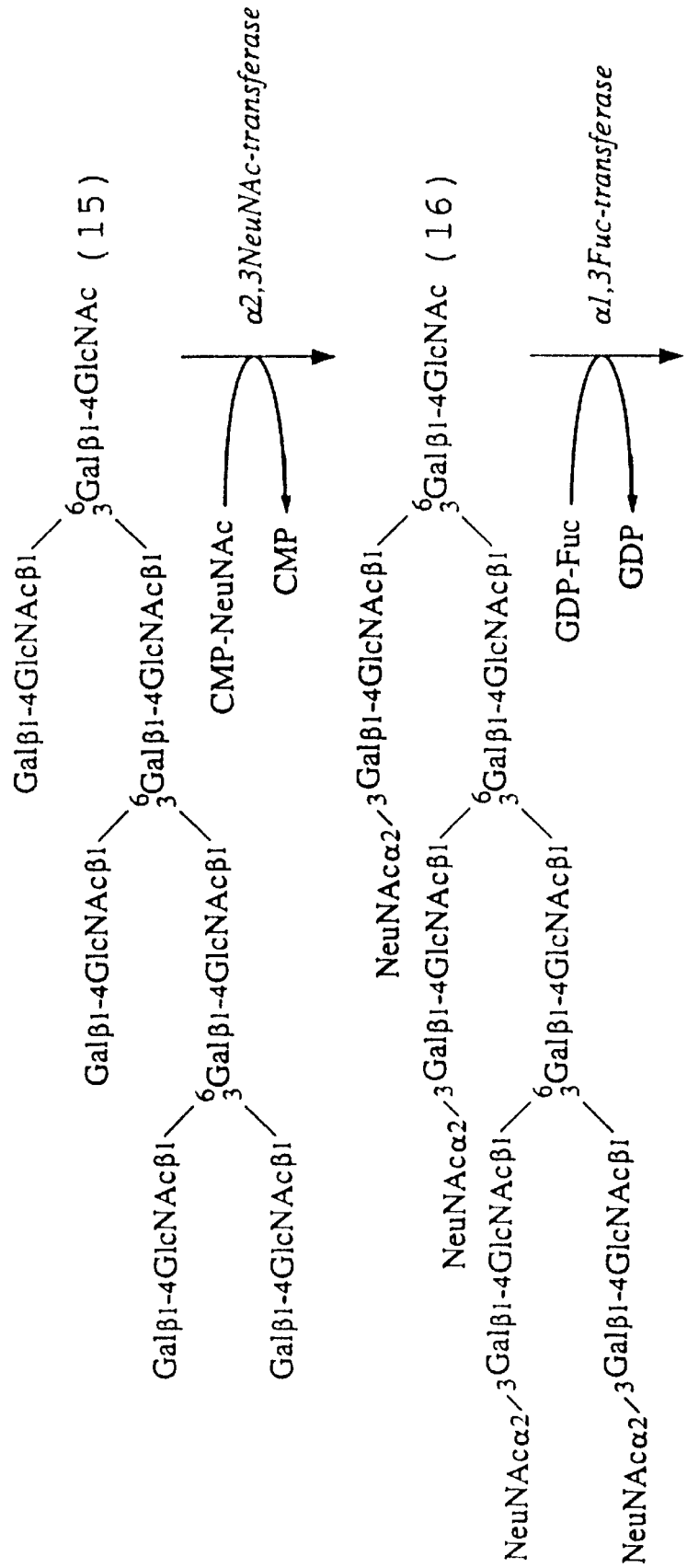

Example 6
Synthesis and Characterization of Tetravalent sLex Glycan, having a Linear Polylactosamine Backbone (An outline of the synthesis route employed in the present example is shown in FIG. 9 and the bolded numbering corresponds to glycan structures in FIG. 9)

Material and Methods

Synthesis of the octasaccharide glycan 12

The hexasaccharide LacNAcβ1-3'LacNAcβ1-3'LacNAc was decorated by the two β1,6-bonded GlcNAc branches by incubating it with UDP-GlcNAc and the centrally-acting β1,6-GlcNAc transferase (GlcNAc to Gal), present in rat serum (Gu et al., *J. Biol. Chem.* 267: 2994–2999 (1992)). The resulting glycan 12 was purified by chromatography and extensively characterized by degradative experiments as well as $^1$H-NMR and MALDI-TOF mass spectrometry.

$^1$H-NMR-spectroscopy

Prior to NMR-experiments the saccharides were twice lyophilized from $^2$H$_2$O and then dissolved in 600 ml $^2$H$_2$O (99.996%, Cambridge Isotope Laboratories, Woburn, Mass., USA). The NMR-experiments were performed on a Varian Unity 500 spectrometer at 23° C. In recording the proton spectra, a modification of WEFT sequence (Hård et al., *Eur. J. Biochem.* 209:895–915 (1992)) was used. The $^1$H chemical shifts were referenced to acetone, 2.225 ppm.

Matrix-assisted laser desorption/ionization time-of-flight mass spectrometry (MALDI-TOF.

MALDI-TOF mass spectrometry was performed in the positive ion reflector mode with irradiation from a nitrogen laser (337 nm) and 2,5-dihydroxybenzoic acid as the matrix with the Finnigan Vision 2000 time-of-flight instrument (Thermo BioAnalysis, Ltd., Hemel Hempstead, UK), operated at 5 kV accelerating voltage and with 4 kV postacccleration at the detector. External calibration was used. Mass assignments are reported as average mass values, unless noted otherwise.

Transferase reactions

The reactions with hog gastric β1,6-GlcNAc transferase (Piller et al., *J. Biol. Chem.* 259:13385–13390 (1984)), bovine milk β1,4-galactosyltransferase (Brew et al., *Proc. Natl. Acad. Sci. USA* 59: 491–497 (1968)), human serum β1,3-GlcNAc transferase (Yates and Watkins, *Carbohydr. Res.* 120: 251–268 (1983)), human placenta α2,3- sialyltransferase (Nemansky and van den Eijnden, *Glycoconjugate J*. 10:99–108 (1993)) and human milk α1,3-fucosyltransferase (Eppenberger-Castori et al., *Glycoconjugate J*. 6:101–114 (1989); Natunen et al., *Glycobiology* 4:577–83 (1994)) were performed essentially as described (Maaheimo et al., *Eur. J. Biochem*. 234:616–625 (1995)).

Chromatographic methods

Gel permeation chromatography on Superdex 75 HR (Pharmacia Sweden) was performed on two consecutive columns (10×300 mm) run at 0.5 ml/min with water (neutral saccharides) or 0.05M $NH_4HCO_3$ (sialic acid-containing saccharides). The effluent was monitored at 214 nm and the oligosaccharides were quantified against external GlcNAc and Neu5Ac.

For anion exchange chromatography, a MonoQ (5/5) column (Pharmacia) was eluted at a rate of 1 ml/min, first isocratically with water for 4 min, then with a linear gradient of 0 to 0.05M NaCl over 8 min, and finally with a linear gradient of 0.05 to 0.5M NaCl over 8 min.

High-pH anion exchange chromatography with pulsed amperometric detection (HPAEC-PAD) was performed on a (4×250 mm) Dionex CarboPac PA-1 column at a flow rate of 1 ml/min., first isocratically with 100 mM sodium acetate in 100 mM NaOH for 5 min, then with a linear gradient of 100 to 200 mM sodium acetate in 100 mM NaOH over 55 min. The fractions collected were neutralized with 0.4M aqueous acetic acid, and desalted by using gel permeation chromatography on a Superdex HR 75 column.

Exoglycosidase digestions

For cleavage with *A. ureafaciens* sialidase (Boehringer, Mannheim, Germany), saccharide samples were incubated overnight with 80 mU of the enzyme in 40 μl of 100 mM sodium acetate, pH 5.0. Incubation with jack bean β-galactosidase was performed as described (Renkonen et al., *Glycoconjugate J*. 6:129–140 (1989)). In parallel β-galactosidase reactions, the disaccharide ($^3$H)Galβ1-4GlcNAc was completely degraded, releasing ($^3$H)Gal.

Enzymatic Synthesis of a Tetravalent sLex Glycan having a Linear Polylactosamine Backbone (Glycan 17)

The five-step synthesis was started from the octameric polylactosamine LacNAcβ1-3'(GlcNAcβ1-6')LacNAcβ1-3'(GlcNAcβ1-6')LacNAc (12)

Figure 10A:
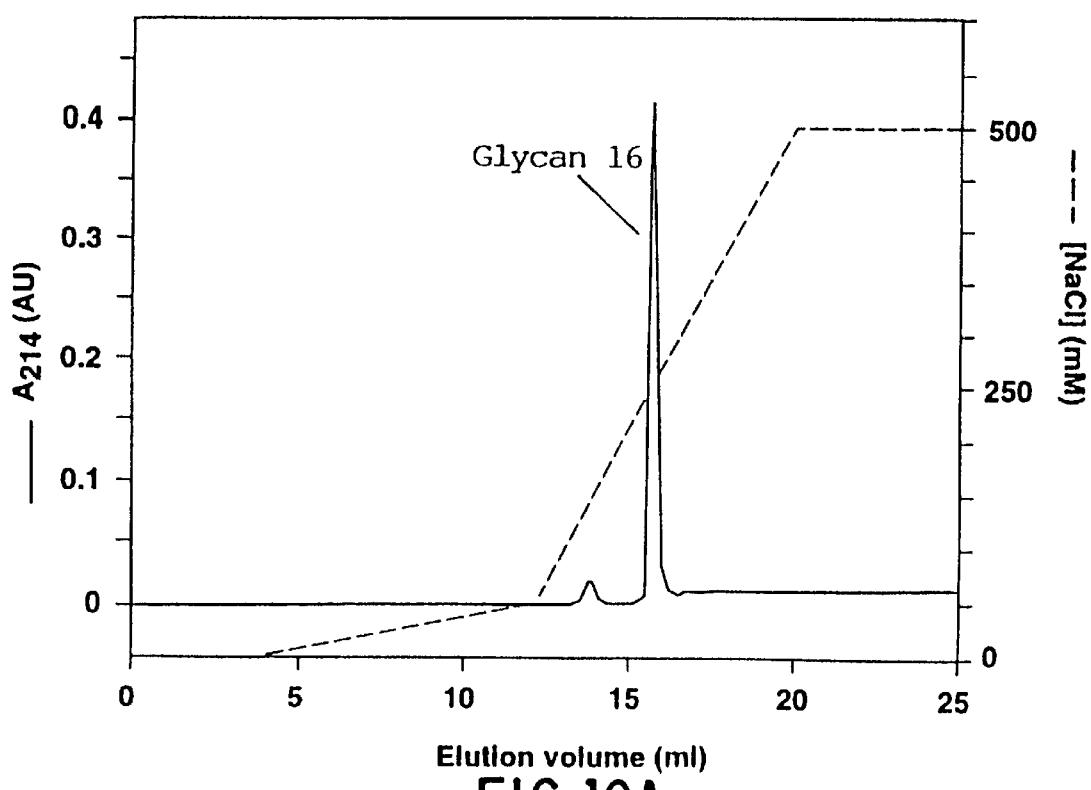
FIG. 10. A. Anion exchange (MonoQ) chromatography of glycan 16. B. HPAE-PAD chromatography of glycan 17, isolated from the synthesis mixture by gel filtration. The major peak eluting at 8 min. represents glycan 17, while the peak at 12 min. is believed to contain its reducing end-ManNAc analog. The latter was probably formed by base-catalyzed epimerization at C2 of the reducing end-GlcNAc of glycan 17 and/or the precursors. No oligosaccharide eluting at 15–17 min, the expected eluting area of the trifucosyl analogs of glycan 17, was observed.
Figure 11A:
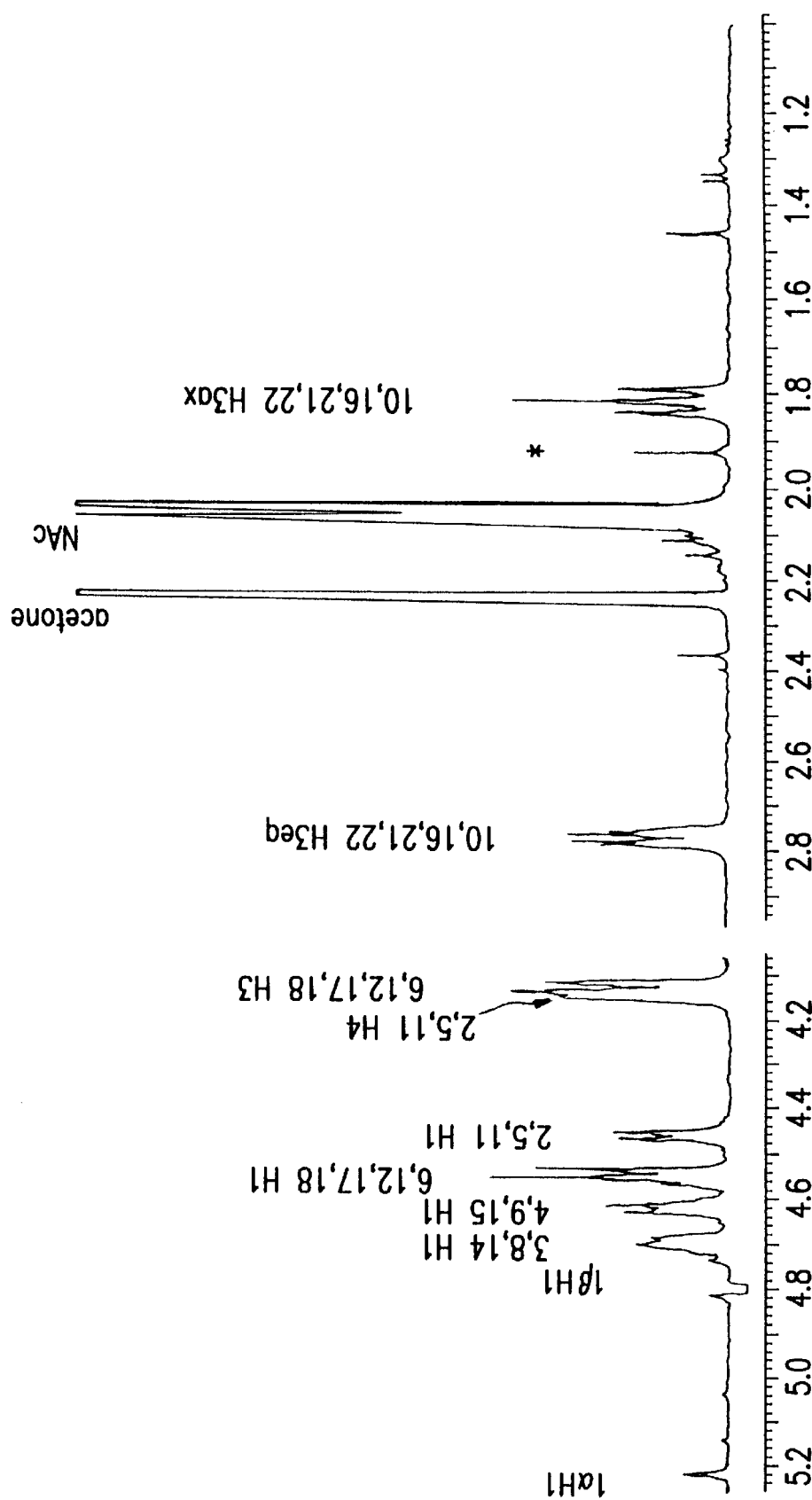
FIG. 11 (panels A, B and C). A) Expansions of $^1$H-NMR spectra of glycan 16. B) $^1$H-NMR spectrum of glycan 17. The resonances marked by an asterisk (*) arise from unknown impurities. C) $^1$H-NMR chemical shifts of structural reporter groups of glycans 16 and 17 at 23° C.

The octasaccharide 12 (150 nmol) was first elongated in β1,3-GlcNAc transferase reaction. The nonasaccharide 13 and some unreacted 12 were isolated as a mixture by Superdex 75 HR chromatography, and subjected as such to a reaction catalyzed by β1,6-GlcNAc transferase from hog gastric mucosa. The resulting oligosaccharides revealed five components in matrix assisted laser desorption/ionization time-of-flight (MALDI-TOF) mass spectrometry, ranging from $GlcNAc_7Gal_3$ (Glycan 5, 48%) and $GlcNAc_6Gal_3$ (23%) down to $GlcNAc_4Gal_2$ (2.6%). The complex mixture was generated notably by β-galactosidase and β-N-acetylglucosaminidase activities known to be present in the crude β1,6-GlcNAc transferase extract of hog gastric mucosa (Helin et al., *FEBS Lett*. 335:280–284 (1993)). Superdex 75 HR chromatography of the product mixture gave two fairly well separated peaks (not shown). According to MALDI-TOF mass spectrometry the major peak, eluting at 60.94 min, had two major components: (M+Na)$^+$ m/z 1949.5 (65%) represented $GlcNAc_7Gal_3$ (calc. m/z 1949.8) and (M+Na)$^+$ m/z 1746.7 (30%) represented $GlcNAc_6Gal_3$ (calc. m/z 1746.6). The most abundant ion in the molecular ion region of the mass spectrum of the minor peak at 62.94 min. had (M+Na)$^+$ m/z 1380.5 (monoisotopic), indicating that it contained mainly (70%) $GlcNAc_5Gal_2$ (calc. monoisotopic m/z 1380.5). Low abundance peaks of monoisotopic m/z 1177.4, 1542.5 and 1746.0 could be assigned to the $GlcNAc_4Gal_2$, $GlcNAc_5Gal_3$ and $GlcNAc_6Gal_3$ species, respectively (calculated monoisotopic values m/z 1177.4, 1542.6 and 1745.6). In the Superdex HR 75 run, the separation between glycan 5 and $GlcNAc_5Gal_3$, missing two GlcNAc residues, was about two minutes.

β1,4-Galactosyl transferase reaction converted 14 into 15, the branched array of seven LacNAc units. Superdex 75 HR chromatography revealed a well-shaped oligosaccharide peak, emerging 2.2 min earlier than the acceptor 5 (not shown). On Biogel P-4 columns, too, four additional galactose residues retard oligosaccharide migration as much as two additional GlcNAc residues (Yamashita et al., *Methods Enzymol*. 83:105–126 (1982)). The MALDI-TOF mass spectrum of the galactosylated oligosaccharide showed signals at m/z 2598.1, assigned as (M+Na)$^+$ of $GlcNAc_7Gal_7$, the Glycan 15, (calc. m/z 2598.4) (65%) and m/z 2233.0, assigned as (M+Na)$^+$ of $GlcNAc_6Gal_6$ (calc. m/z 2233.0) (35%).

α2,3-Sialyltransferase reaction converted 15 to 16; a concentrate of the latter was isolated by using gel permeation chromatography on Superdex 75 HR (not shown). For further purification the concentrate was subjected to anion exchange chromatography on a MonoQ-column. (FIG. 10A). Glycan 16 chromatographed in these experiments like the isomeric tetrasialo glycan 9, described in Example 2. After desalting on Superdex 75 HR, 45 nmol of pure glycan 16 was obtained. $^1$H-NMR spectrum of glycan 16 (FIG. 11A and FIG. 11C) confirms its structure.

Figure 10B:
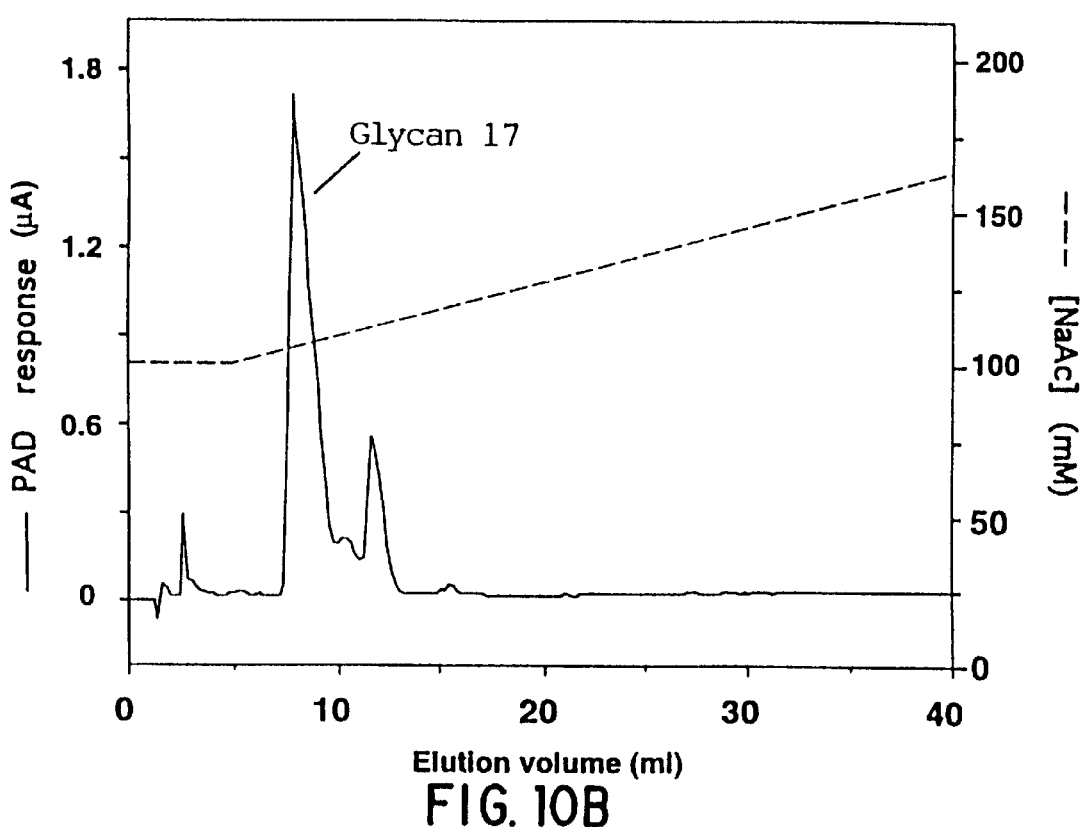

A small sample of glycan 16 was subjected to HPAE-PAD chromatography on a Dionex column of CarboPac PA-1. It emerged at 43 min (not shown), at a position equivalent to that of the isomeric tetrasialo compound 8 described in Example 2.

α1,3-Fucosyltransferase reaction converted glycan 16 (38 nmol) to the tetravalent sLex saccharide 17. Preliminary purification of 17 was effected by chromatography on Superdex 75 HR. Subsequent HPAE chromatography on the CarboPac PA-1 column gave 8 as a well-shaped peak emerging at 8 min (FIG. 10B). The presence of four fucosyl residues reduced the affinity of Glycan 17 to CarboPac PA-1 dramatically, compared to glycan 16. This is known to be characteristic to fucosylated saccharides (Hardy, M. R. & Townsend, R. R., *Carbohydr. Res*. 188:1–7 (1989)). Parallel experiments with the tetravalent sLex glycan 9 (see Table 2) revealed that 1 nmol samples of glycan 9 and 17 co-chromatographed on CarboPac PA-1 at 9 min; the trifucosyl analog of the glycan 9 (glycan 10 described in Example 2) emerged in these experiments much later, at 16 min. Desalting on the Superdex 75 HR column yielded 24 nmol of glycan 17.

Structural characterization of glycan 17

Figure 11B:
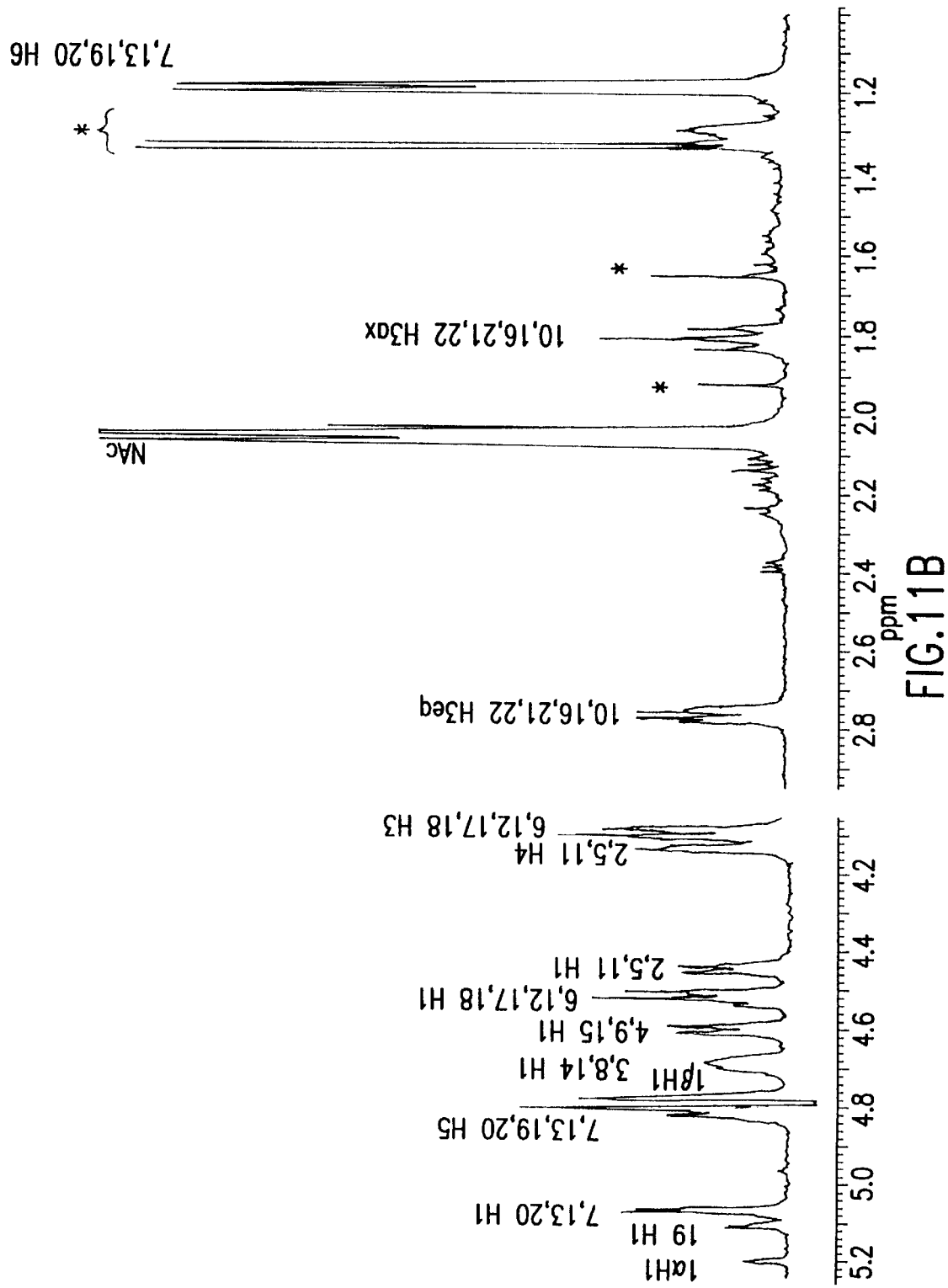

$^1$H-NMR spectrum of glycan 17 (FIG. 11B and FIG. 11C) confirms the structure. Besides the reducing end GlcNAc, H-1 signals of three β1,3-linked GlcNAc residues at 4.684–4.696 ppm are visible and accompanied by H-1 signals of three β1,6-bonded GlcNAc units at 4.603 ppm. The six GlcNAc residues are bonded to three galactoses, which reveal H-4 resonances at 4.133 ppm, the characteristic chemical shift for H-4 of a galactose that is disubstituted by GlcNAc units at positions 3 and 6 (Koenderman et al., *Eur. J. Biochem*. 166: 199–208 (1987)). The galactose H-1 region reveals signals of the three branching galactoses at 4.452 ppm, those of sialylated galactoses of the three β1,6-bonded sLex determinants at 4.517 ppm and those of the β1,3-bonded sLex at 4.533 ppm. The H-3 signals of these galactoses are characteristically (Kamerling & Vliegenthart, *Biological Magnetic Resesonance*, Berliner & Reuben, editors, vol. 10, Plenum Press, New York & London (1992), pp. 1–287)) at 4.089 ppm. The equatorial and axial H-3 resonances of Neu5Ac at 2.762 and 1.798 ppm, respectively, confirm the presence of four equivalents of α2,3-bonded Neu5Ac (Kamerling & Vliegenthart, *Biological Magnetic Resonance*, Berliner & Reuben, editors, vol. 10, Plenum Press, New York & London (1992), pp. 1–287). The signals of the methyl protons at 2.04 ppm corresponded to the presence of 11 N-acetyl groups. The H-1 of the fucose residue in the β1,3-bonded sLex determinant resonated at 5.119 ppm, while those of the three β1,6-bonded sLex units resonated at 5.076 ppm. The H-5 and H-6 signals of the fucoses resonated characteristically (de Vries et al., *FEBS Lett.*, 330:243–248 (1993); Vliegenthart et al., *Adv. Carbohydr. Chem. Biochem.*, 41:209–374(1983)) at 4.820 and 1.166 ppm, respectively. The integrals of the H-1 and H-6 protons indicated the presence of four fucoses.

The presence of four fucose residues in glycan 17 was confirmed by degradation experiments and ensuing MALDI-TOF mass spectrometry. A sample of glycan 17 (2 nmol) was treated with *Arthrobacterium ureafaciens* sialidase. The desalted reaction mixture was subjected to MonoQ chromatography, which revealed that 1 nmol of the neutral asialo-oligosaccharide 18 had been formed. In the MALDI-TOF mass spectrum of glycan 18, a major (M+Na)$^+$-peak, representing 80% of the polylactosamine signals, was observed at m/z 3182.8 (calculated for $Fuc_4Gal_7GlcNAc_7$, 3182.9). Two minor components, evident in the spectrum, behaved as $Fuc_3Gal_7GlcNAc_7$ (12%) and $Fuc_3Gal_6GlcNAc_6$ (8%). The minor signals may represent degradation products generated during desialylation or mass spectrometry, because repeated HPAE-PAD chromatographic runs of intact 8 on CarboPac PA-1 failed to reveal any significant amounts of material eluting at 16 min, around the expected position of $Neu5Ac_4Fuc_3Gal_7GlcNAc_7$.

Glycan 18 resisted jack bean β-galactosidase treatment. The unchanged MALDI-TOF mass spectrum had the $Fuc_4Gal_7GlcNAc_7$ (M+Na)$^+$ signal (calc. m/z 3182.9) as the major component, measured at m/z 3182.8 before and m/z 3183.2 after the treatment. The β-galactosidase resistance is characteristic to terminal Galβ1-4(Fucα1-3)GlcNAc sequences (Kobata A., *Anal. Biochem.* 100:1–14 (1979)). Hence, all fucose residues of glycan 17 were bonded to the distally located, sialylated N-acetyllactosamine units The data confirm and extend previous findings, showing that α1,3-fucosyltransferases from human milk do not react with LacNAc residues that carry branches at the 6'-position (Niemelä, R et al., *Glycoconjugate J.* 12:36–44 (1995); Maaheimo, H. et al., *Eur. J. Biochem.*, 234:616–625 (1995); Seppo, A. et al., *Glycobiology* 6:65–71 (1996)).

Example 7
Tetravalent sLex Glycans, Derived from a Linear or Branched Polylactosamine Backbone, as Inhibitors of L-selectin-dependent Lymphocyte Adhesion to Endothelium Transplantations and lymphocyte adhesion assay Ten to twelve weeks old rats of inbred WF (RT1$^V$) and DA (RT1$^a$) strains were used for the transplantations and lymphocyte adhesion assays as described in Example 1. The binding assays consisted of three experiments performed on separate days. Each experiment involved incubation of lymphocytes with six individual sections of the rejecting heart in the presence of the saccharides at a given concentration.

Inhibition of L-selectin mediated lymphocyte adhesion

In parallel experiments the capacity of the tetravalent sLex glycans 9 and 17, and of the nonfucosylated analogs glycan 8 and glycan 16, were compared in inhibiting L-selectin-dependent lymphocyte adhesion to cardiac endothelium during acute rejection. The lymphocytes were preincubated for 30 min with varying concentrations of the oligosaccharides and used thereafter in the Stamper-Woodruff binding assay in the incubation media as described in Example 1.

Figure 12:
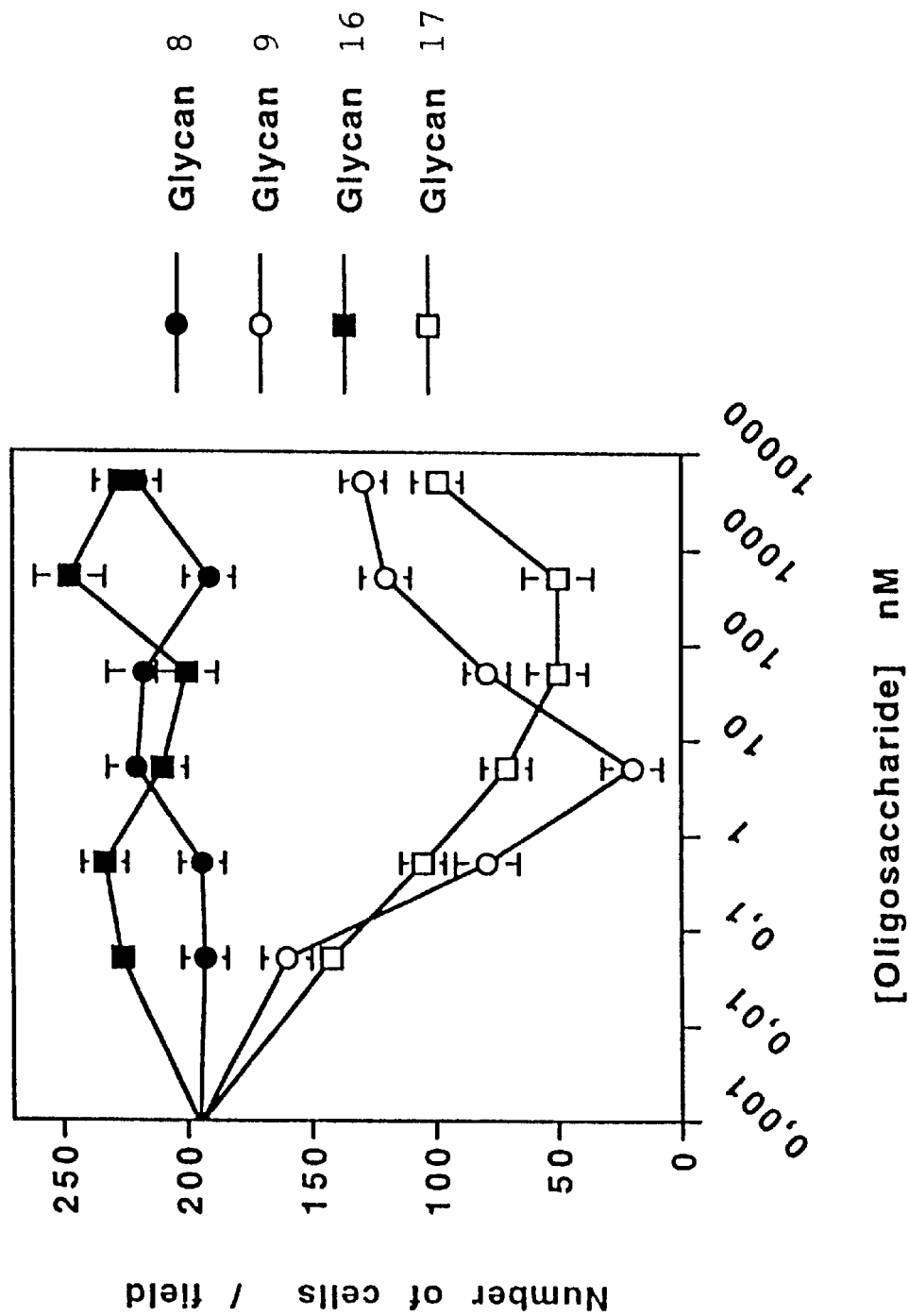
FIG. 12. L-selectin-dependent binding of lymphocytes on endothelium of rejecting cardiac transplants of rats in the presence of synthetic oligosaccharides. The mean±SEM of one representative experiment out of three is presented. The tetravalent sialyl Lewis glycans 9 and 17 inhibited the lymphocyte adhesion strongly, revealing IC$_{50}$ values around 1 nM. The nonfucosylated analogs 8 and 16 revealed no inhibitory properties.

The two sLex bearing glycans 9 and 17 were effective in inhibiting lymphocyte adhesion to activated cardiac epithelium, the $IC_{50}$-values being around 1 nM for both sLex glycans (FIG. 12). The crucial control saccharides 8 and 16, having the same charge, the same overall structure and approximately the same size, but being devoid of fucose, did not alter the lymphocyte binding from background levels. These data indicate that both the branched and linear tetravalent sLex glycans are extremely efficient in inhibiting the L-selectin-dependent lymphocyte adhesion to endothelium and thereby reducing the rejection associated inflammation.

The biological properties of the linear-backbone glycan 17 resembled those of the isomeric branched-backbone glycan 9 Both of these glycans were very potent L-selectin antagonists in the present Stamper-Woodruff adhesion experiments: Glycan 17 revealed strong inhibitory effect down to 0.5 nM, and glycan 9 was an equally potent L-selectin antagonist (see FIG. 12). It is remarkable that both 17 and 9 show high-affinity binding to L-selectin. This is analogous to the data of (Crottet et al., *Glycobiology*, 6:191–208 (1996)), showing that subsets of mucins of diverse origins are high-affinity selectin ligands. Obviously, neither unique backbone arrays nor rigidly defined binding determinants are required for high-affinity recognition by L-selectin. Rather, clusters of sLex/sLea-related determinants, "properly presented" on backbones of polylactosamine or polypeptide nature, are important. In the present examples, the activities of glycans 17 and 9 were completely dependent on the presence of the intact sLex sequences in the binding determinants; the presence of the α1,3-bonded fucose residues was required for recognition.

The low nanomolar concentration range of multivalent sLex glycans reported here is several orders below the inhibitory range of monovalent sLex. Other conventional high affinity inhibitors of L-selectin include mucins of endothelial and other origins (Baumhueter, S. et al., *Science* 262:436–438 (1993); Berg, E. L. et al., *Nature* 366:695–698 (1993); Crottet, P. et al., *Glycobiology* 6:191–208 (1996); Hemmerich, S. et al., *Biochemistry* 33:4820–4829 (1994); Hemmerich S. et al., *J. Biol. Chem.*, 270:12035–12047 (1995); Hemmerich, S. and Rosen, S. D., *Biochemistry* 33:4830–4835 (1994); Imai, Y. and Rosen, S. D., *Glycoconjugate J.* 10:34–39 (1993); Imai Y. et al., *J. Cell Biol.* 113:1213–1222 (1991); Lasky, L. A. et al., *Cell* 69:927–938 (1992)).

Interestingly, the O-linked oligosaccharides released from these mucins by alkaline borhydride did not show any detectable binding to L-selectin in affinity chromatography experiments (Crottet et al., *Glycobiology* 6:191–208 (1996)). The data of the present invention show, however, that oligosaccharides of proper structure can be recognized by L-selectin with high affinity.

The high biological activity of glycans 17 and 9, compared to the monovalent sLex, is based on their multivalency. The multivalent sLex glycans crosslink two or several L-selectin molecules, known to be clustered on the tips of lymphocyte microvilli (Hasslen, S. R. et al., *Histochem. J.* 27:547–554 (1995); von Andrian et al., *Cell* 82.989–999 (1995)). The segmental flexibility of L-selectin is helpful in the presentation of the carbohydrate recognizing domains (Rosen, S. D. and Bertozzi, C. R., *Curr. Opin. Cell Biol.* 6:663–673 (1994)), allowing crosslink-formation despite the vicinity of the individual sLex determinants in a given ligand molecule. The proximal ends of two sLex determinants of 9, for example, are at most only 2 nm apart, even in the maximally extended conformation of the polylactosamine backbone (Renouf, D. V. and Hounsell, E. F., *Int. J. Biol. Macromol.* 15:37–42 (1993)). However, high-affinity binding to cell surfaces has been observed with soluble monomeric P-selectin (Ushiyama, S. et al., *J. Biol. Chem.* 268:15229–15237 (1993)) and E-selectin (Hensley, P. et al., *J. Biol. Chem.* 269:23949–23958 (1994)), indicating that multivalent sLex glycans acquire their high affinity by binding to two distinct sites within a L-selectin monomer. Furthermore, recent data (Malhotra, R. et al, *Biochem. J.* 314:297–303 (1996)) suggest that the interaction of L-selectin and its endothelial ligands requires occupancy of both the sLex-recognizing site (CRS), which is monovalent, and a distict adjacent binding site recognizing acidic determinants (ARS). This arrangement is similar to the clustered patch, involving tyrosine sulfate residues immediately adjacent to sialylated oligosaccharides, generating P-selectin recognition in PSGL-1 (Sako, D. et al, *Cell* 83:323–331 (1995); Wilkins, P. P. et al., *J. Biol. Chem.* 270:22677–22680 (1995)). Hence, the tetravalent sLex glycans 17 and 9 bind to monomeric L-selectin in two ways, a specific joint between one sLex-determinant and the CRS, and a less specific binding between the sialic acid of another sLex-residue in the ligand and the ARS of L-selectin. This requires that even partially fucosylated derivatives of the tetrasialoglycan 16, for instance, are particularly good adhesion inhibitors. Regardless of the binding mode, the saccharide antagonists of L-selectin, exemplified by glycans 17 and 9, are potential anti-inflammatory drugs, because they are much less antigenic than the mucins or neoglycoprotein ligands of selectins (Welply, J. K. et al., *Glycobiology* 4:259–265 (1994)).

In addition to L-selectin-mediated processes, glycans 17 and 9 inhibit adhesion phenomena involving other selectins. For example, the data of Nelson, R. M. et al. *Blood* 82:3253–3258 (1992) show that E-selectin-dependent adhesion may be even more effectively inhibited than L-selectin-mediated processes by sLex-saccharides.

Example 8
Synthesis and Characterization of Oligosaccharide Alditols
(Bolded numbering corresponds to glycan structures in FIG. 13)
Materials and Methods
Enzymes Hog gastric β1,6 N-acetylglucosaminyltransferase (EC 2.4.1.148), bovine milk β1,4 galactosyltransferase (EC 2.4.1.90), human serum β1,3 N-acetylglucosaminyltransferase (EC 2.4.1.149), human placenta α2,3 sialyltransferase and human milk α1,3/4-fucosyltransferase.

Saccharides and monosaccharide nucleotides

Galβ1-3GalNAc, UDP-GlcNAc, UDP-Gal, CMP-NeuAc and GDP-Fuc were purchased from Sigma, St Louis, Mo., USA.

NeuAcα2-3Galβ1-4(Fucα1-3)GlcNAc (sialyl Le$^x$) 1 and NeuAcα2-3Galβ1-4(Fucα1-3)GlcNAcβ1-3(NeuAcα2-3Galβ1-4(Fucα1-3)GlcNAcβ1-6)Galβ1-4GlcNAc 4 were synthesized enzymatically in vitro as described in Example 2.

Transferase reactions

The reactions with hog gastric β1,6 N-acetylglucosaminyltransferase (EC 2.4.1.148) (Seppo, A. et al., *Biochem. Cell Biol.* 68:44–53 (1990)), bovine milk β1,4 galactosyltransferase (EC 2.4.1.90) (Sigma) (Brew, K. et al., *Proc. Natl. Acad. Sci. USA* 59:491–497 (1968)) and human serum β1,3 N-acetylglucosaminyl-transferase (EC 2.4.1.149) (Seppo, A. et al., *Biochem. Cell Biol.* 68:44–53 (1990)) were carried out essentially as described in the cited references.

The human placental microsomes used, containing α2,3 sialyltransferase activity, were prepared as described in Example 2 The transferase reactions were carried out in 50 μl of the buffer, by incubating 100 nmol of the saccharide (corresponding to 200 nmol of acceptor sites) with 2 μmol of CMP-NeuAc and 25 μl of human placental microsomes for 17 h at 37° C. The reaction was terminated by heating in a boiling water bath for 5 min. The precipitating protein was removed and the combined supernatant and washings were lyophilized.

α1,3/4-Fucosyltransferase (8 mU/ml of total fucosyltransferase; 0.79 mg/ml of protein) was extracted from human milk as described in Example 2 and the transferase reaction was carried out as described (Palcic, M. M. et al., *Carbohydr. Res.* 190:1–11 (1989)).

Reduction of the tetrasaccharide Galβ1-4GlcNAcβ1-6 (Galβ1-3)GalNAc (22) was carried out with NaBH$_4$ essentially as described (Rasilo & Renkonen, *Hoppe Seyler's Z. Physiol. Chem.* 363:89–93 (1982)). The completeness of the reaction was controlled by subjecting the borate free saccharide to $^1$H NMR.

Chromatographic methods

Gel permeation chromatography on a column of Bio-Gel P-2 (Bio-Rad Richmond, Calif., USA) (1×144 cm) or Bio-Gel P-4 (1×145 cm) was carried out with 0.02% aqueous NaN$_3$.

Gel permeation chromatography on a column of Superdex 75 HR (10×300 mm) (Pharmacia, Sweden) was run with water (neutral saccharides) or 0.05M NH$_4$HCO$_3$ (sialic acid containing saccharides) at 1 ml/min. The effluent was monitored at 205 or 214 nm and the oligosaccharides were quantified against external GlcNAc and NeuAc.

High-pH anion-exchange chromatography with pulsed amperometric detection (HPAEC-PAD) was carried out on a (4×250 mm) Dionex CarboPac PA-1 column at a flow rate of 1 ml/min. Neutral saccharides were chromatographed as previously described (Maaheimo, H. et al., *FEBS Lett.* 349:55–59 (1994)). The sialylated saccharides were eluted with a linear gradient of NaAc from 100 mM NaOH, 25 mM NaAc at 0 min to the final composition of 100 mM NaOH, 100 mM NaAc at 20 min. The fractions collected were neutralized with 0.4M acetic acid and desalted by Superdex chromatography.

Anion exchange chromatography on a MonoQ (5/5) column (Pharmacia) Sweden was performed as follows: The column was eluted isocratically 1 ml/min with water for 4 min, then with a linear gradient of NaCl to the concentration of 0.05M at 12 min and then with a linear gradient of NaCl to the final concentration of 0.5M at 20 min. The effluent was monitored at 214 nm.

$^1$H -NMR spectroscopy

Prior to NMR experiments, the saccharides were twice lyophilized from $^2$H$_2$O and then dissolved in 600 μl of $^2$H$_2$O (99.996 atom %, Cambridge Isotope Laboratories, Woburn, Mass., USA). The NMR experiments were carried out on a Varian Unity 500 spectrometer at 300° K. In recording 1D proton spectra, a modification of WEFT sequence (Hård, K. et al., *Eur. J. Biochem.* 209:895–915 (1992)) was used. The overlapping resonances were assigned by DQFCOSY (Marion & Whthrich, *Biochem. Biophys. Res. Commun.* 117:967–974 (1985)) and TOCSY (Bax & Davis, *J. Magn. Reson.* 65:355–360 (1985)). For these experiments, a matrix of 4 k×512 points was collected, typically, and a 90° shifted sine-bell weighting function was employed in both dimensions prior to the Fourier transformation. A relaxation delay of 1 s was used between scans, and, in TOCSY, spin-lock times between 80 and 300 ms (MLEV-17) were used. The $^1$H chemical shifts were referenced to internal acetone, 2.225 ppm.

Synthesis of Oligosaccharide Alditols

The hexasaccharide alditol GlcNAcβ1-3(GlcNAcβ1-6) Galβ1-4GlcNAcβ1-6(Galβ1-3)GalNAc-ol 24 was synthesized as previously described (Maaheimo, H. et al., *FEBS Lett.* 349:55–59 (1994)).

Octasaccharide alditol 25

Figure 14A:
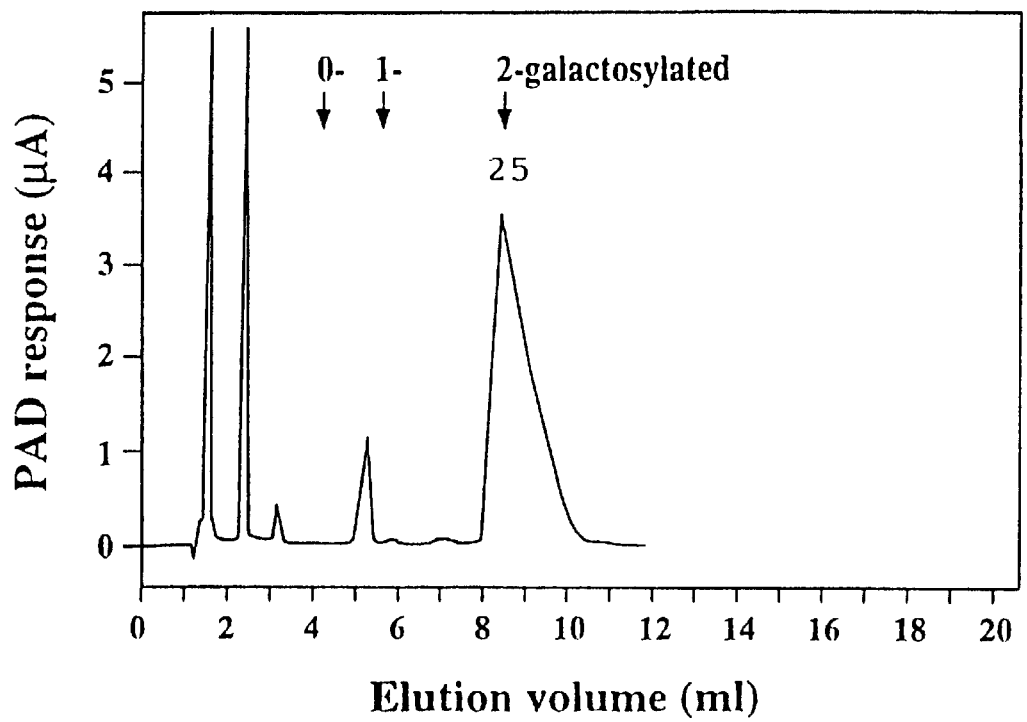
FIG. 14 (panels A–C). Chromatographic analysis of the saccharides after glycosyltranferase reactions. The numbers of the peaks refer to the saccharides in FIG. 15E.
Figure 15A:
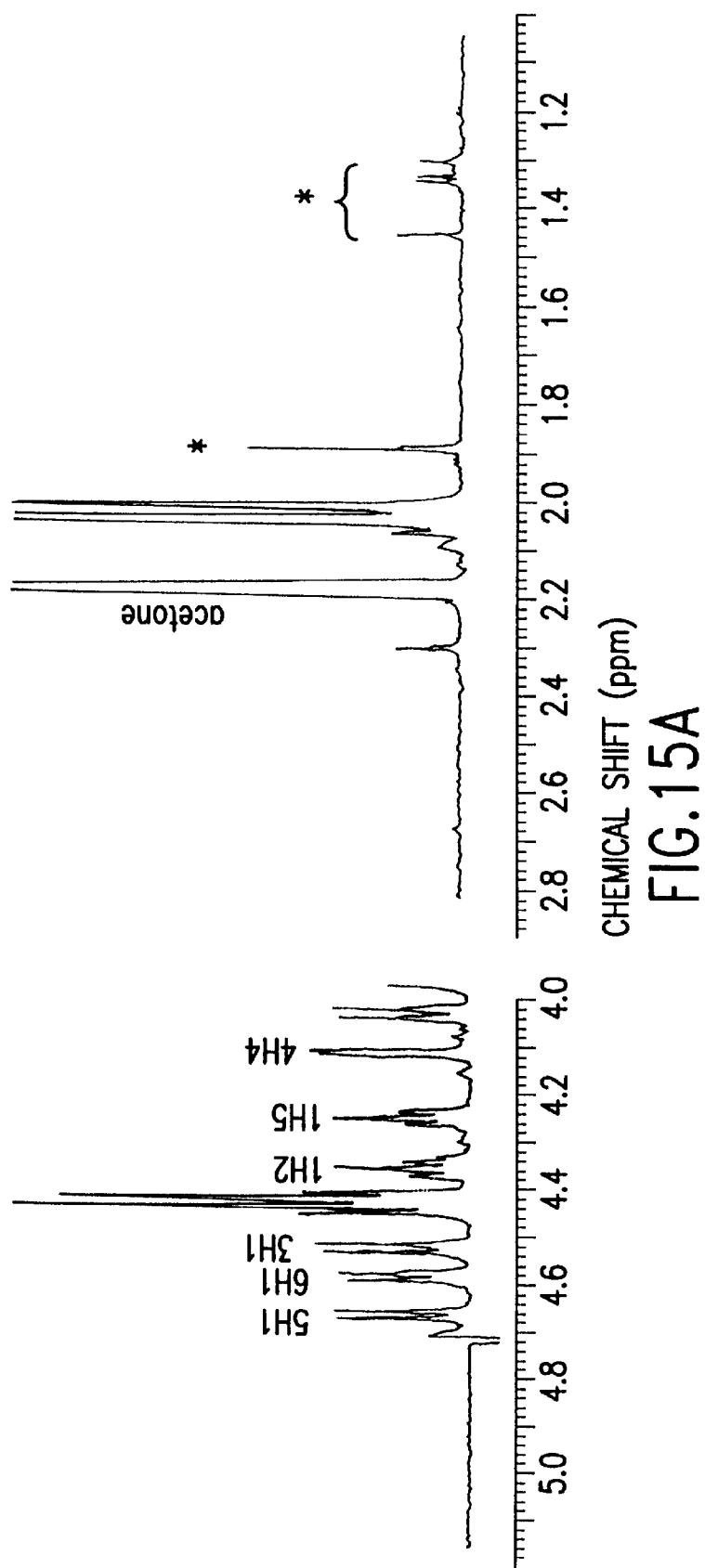
Figure 15B:
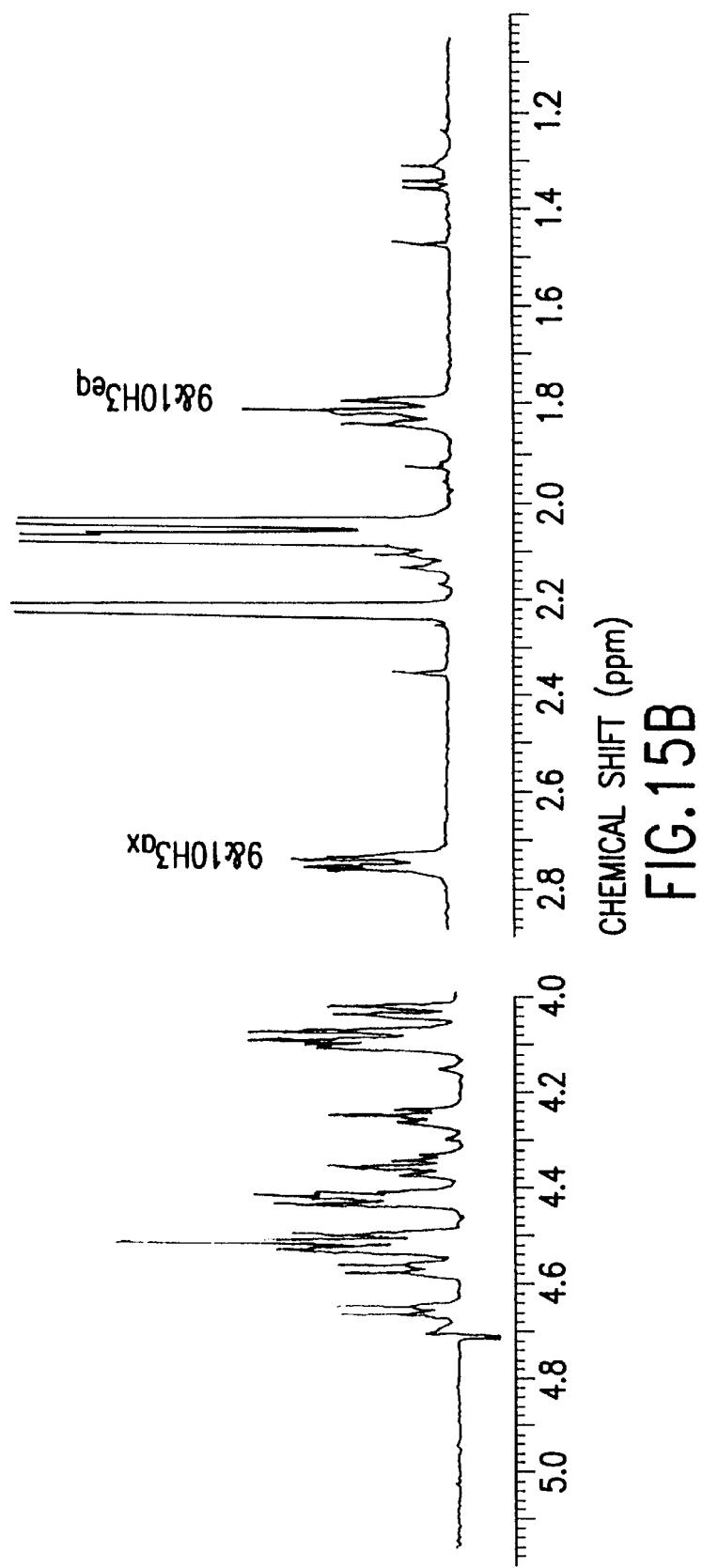
Figure 15D:
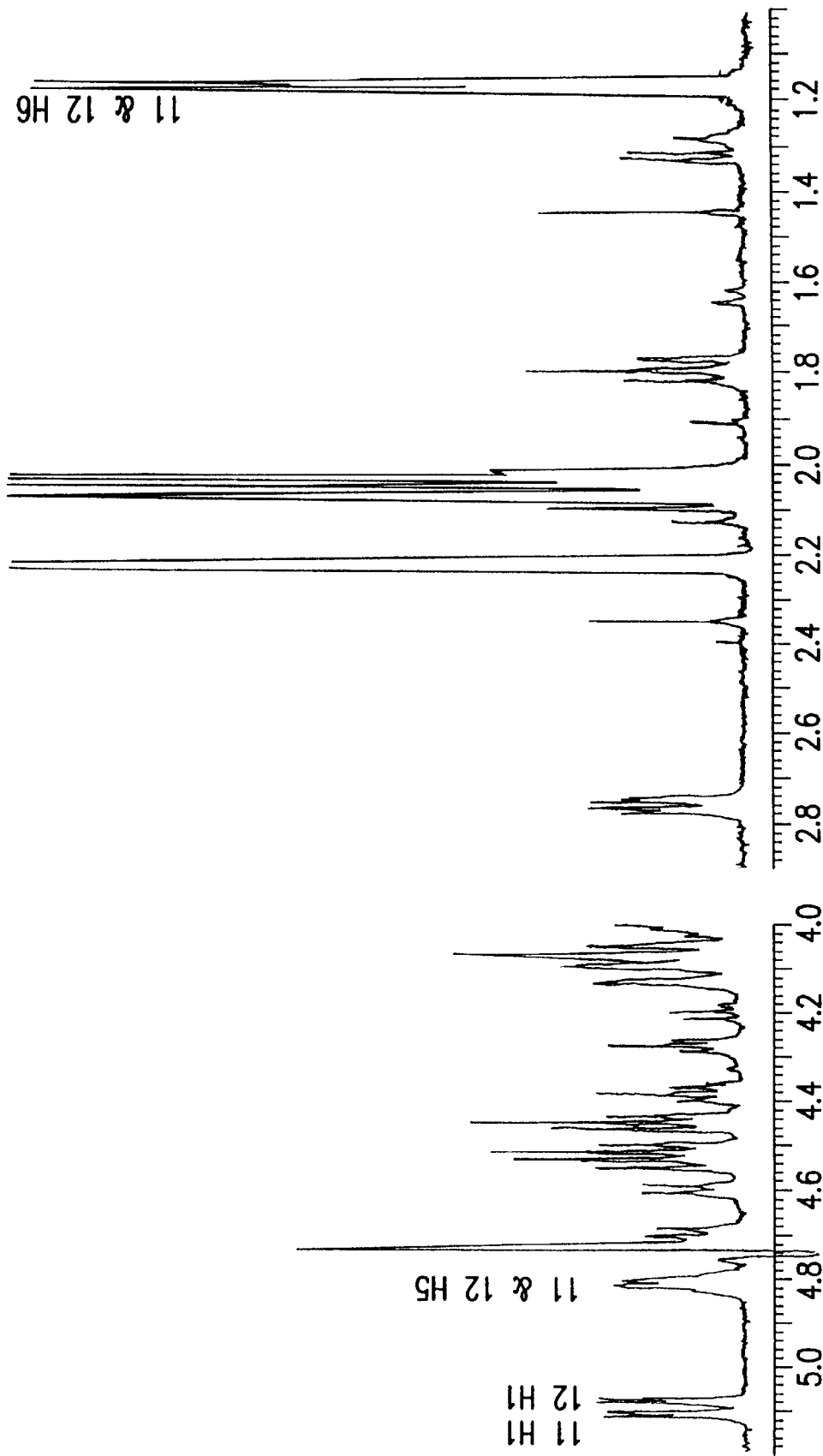

The hexasaccharide alditol 24 was galactosylated by incubating with bovine milk β1,4 galactosyltransferase and 4-fold molar excess of UDP-Gal. The octasaccharide alditol product Galβ1-4GlcNAcβ1-3 (Galβ1-4GlcNAcβ1-6) Galβ1- 4GlcNAcβ1-6(Galβ1-3)GalNAc-ol 25 was purified by HPAEC (FIG. 14A). 400 nmol of 25 was obtained from several reactions. Compared to the $^1$H-NMR spectrum of 24, the anomeric region of spectrum the 25 revealed two new one proton doublets at 4.480 and 4.465 ppm (FIG. 15A). Based on our earlier assignments of partially galactosylated 24 (Maaheimo, H. et al., *FEBS Lett.* 349:55–59 (1994)) these can be assigned to as residues 7 and 8, respectively (see FIG. 13 for the denotation system). The H-3 and H-4 resonances of distal GlcNAc residues 5 and 6 also experience a dramatic downfield shift (FIG. 15E), characteristic to β1,4 galactosylation (Whitfield, D. M. et al., *Can. J. Chem.* 68:942–952 (1990)). Interestingly, also the H-1 and H-2 of GlcNAc residue 3 experience a slight upfield shift upon galactosylation of the distal GlcNAc residues.

Disialodecasaccharide alditol 26

Figure 14B:
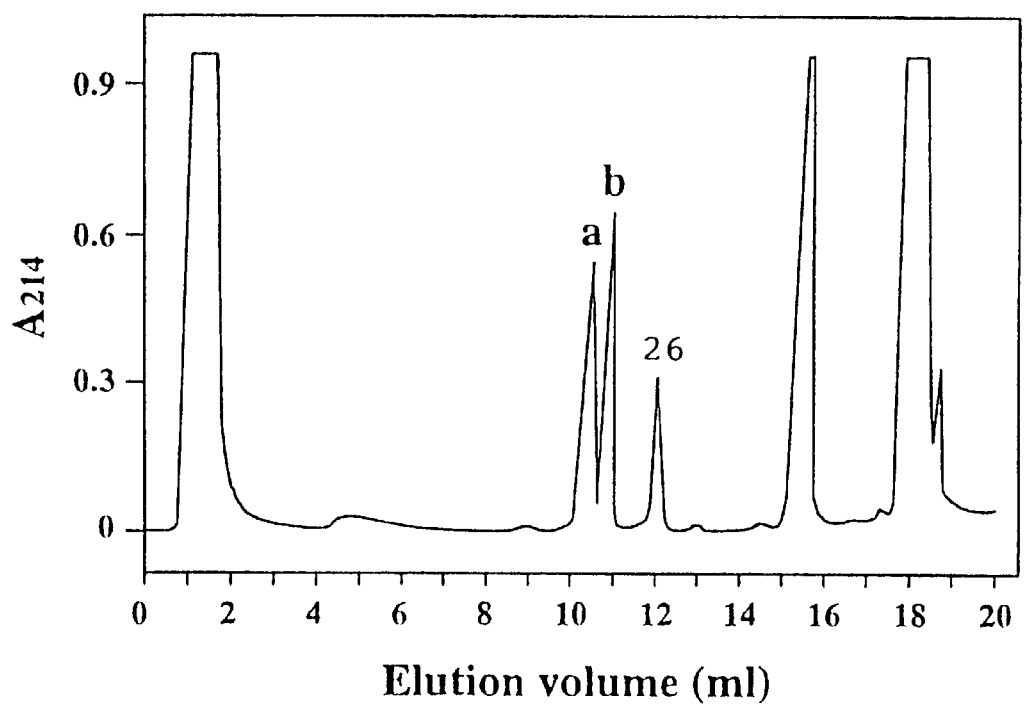

For synthesis of disialyldecasaccharide alditol 26, four batches of 25, 100 nmol each, were incubated at 37° C. for 17 h with 2 μmol of CMP-NeuAc and 25 μl of human placental microsomes containing α2,3 sialyltransferase activity. The reaction mixtures were then fractioned by ion-exchange chromatography on a MonoQ 5/5 column (FIG. 14B) and the product eluting like disialyloligosaccharide (26) was desalted by Superdex 75 chromatography. The NMR spectrum of this material (FIG. 15B) revealed the signals of axial and equatorial H-3 of NeuAc at 2.756 and 1.800 ppm, respectively, the area of both signals corresponding to two protons. These chemical shifts are characteristic of α2,3 linked NeuAc (Kamerling & Vliegenthart, *Biological Magnetic Resonance*, Berliner & Reuben, editors, vol. 10, Plenum Press, New York & London (1992), pp. 1–287), whereas no signals were detected at 2.71 or 1.74 ppm, indicating, that no detectable amount of α2,6 linked NeuAc was present in the sample. Also the large downfield shift of the H-3 resonances of the galactoses 7 and 8 (FIG. 15E), confirm that the NeuAc residues are α2,3 linked to the distal galactoses (Ichikawa, Y. et al., *J. Am. Chem. Soc.* 114:9283–9298 (1992)). As the resonances of galactose 2 were virtually unaffected, the β1,3 linked galactose of the core was not sialylated (Oehrlein, R. et al., *Carbohydr. Res.* 244:149–159 (1993)). Thus, according to the NMR-data the structure of this material is NeuAcα2-3Galβ1-4GlcNAcβ1-3(NeuAcα2-3Galβ1-4GlcNAcβ1-6)Galβ1-4GlcNAcβ1-6 (Galβ1-3)GalNAc-ol 26. From the four reactions, 357 nmol of 26 was obtained.

Mono- and difucosylation of disialyldecasaccharide alditol 26 to alditols 27and28

Figure 14C:
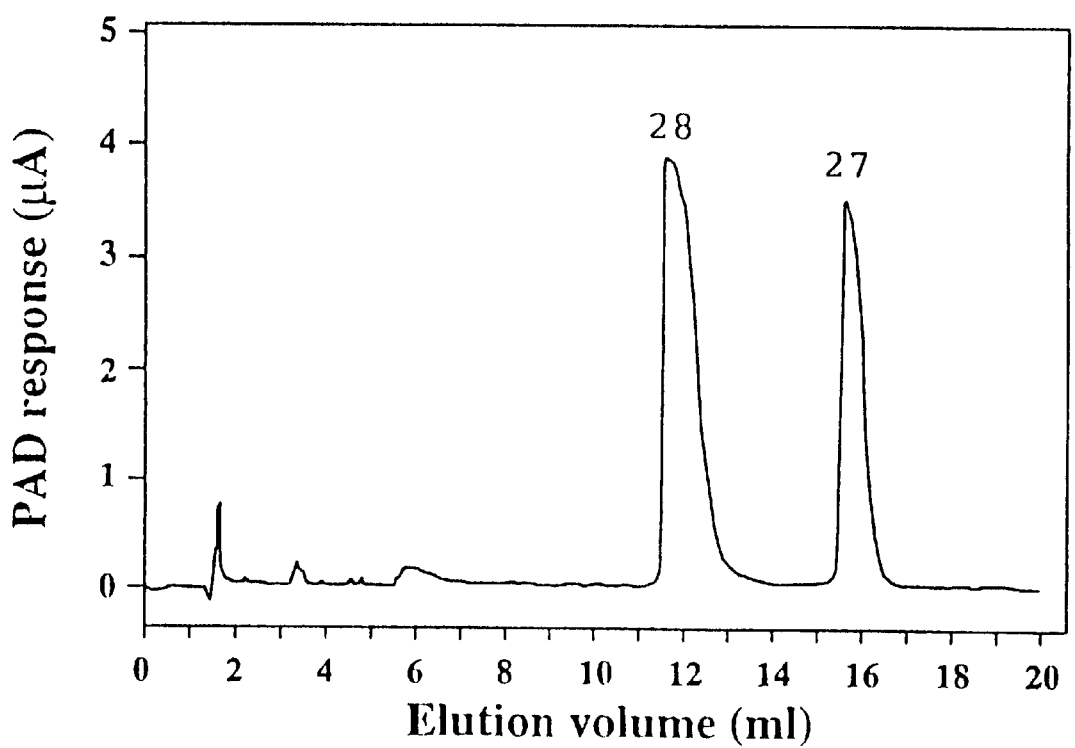

A 347 nmol sample of 26 was subjected to a transferase reaction with 700 nmol of GDP-Fuc and 625 μU of human milk α1,3 fucosyltransferase. The reaction mixture was incubated at 37° C. for 64 h and the reaction was terminated by passing the mixture through a Superdex 75 HR column. When the degree of fucosylation was studied by NMR, integration of the two doublets at 5.086 and 5.117 ppm (the H-1 resonances of the incoming fucoses) revealed that 100% of one of the branches was fucosylated, but only about 40% of the other Branch (not shown). To maximize the amount of difucosylated material, the mixture was subjected to a second round of fucosyl transferase reaction with 600 nmol of GDP-Fuc and 540 μU of the enzyme. The resulting mixture of mono- and difucosylated alditols was then fractioned by HPAEC and two peaks were revealed, corresponding to the di- and monofucosylated products 28 (125 nmol) and 27 (60 nmol), respectively (FIG. 14C).

Characterization of the fucosylated saccharide alditols 27 and 28 by $^1$H-NMR

As compared to that of 26 (FIG. 15B), the anomeric region of the spectrum of the monofucosylated material (FIG. 15C) revealed a new one proton doublet at 5.116 ppm, while the spectrum of the difucosylated material (FIGS. 15D and 17) revealed two doublets at 5.117 and 5.086. These are the H-1 resonances of the incoming fucoses. The structure of the monofucosylated glycan was established by comparison to NMR data from partially fucosylated NeuAcα2-3Galβ1-4GlcNAcβ1-3(NeuAcα2-3Galβ1-4GlcNAcβ1-6)Galβ1-4Gl cNAc, where the H-1 of a fucose bound to the 3-linked arm resonates at 5.116 ppm, while that bound to the 6-linked arm resonates at higher field. Hence, it was concluded, that the fucose in the present monofucosylated glycan (5.116 ppm) is α1-3 linked to the GlcNAc residue 5. That the fucose indeed was bound to the 3-linked arm was also revealed by a slight downfield shift of H-1 resonance of the β1,3 linked GlcNAc (5), while the H-1 signal of β1,6 bonded GlcNAc (6) was unchanged. The structural reporter group signals of galactose 7 and NeuAc 9, too, experience small changes in chemical shift, while those of residues 8 and 10 are unchanged. These data establish the structure of the monofucosylated material as glycan 27.

In the difucosylated material 28, the H-1 signal of GlcNAc residue 6, the one to which the second fucose binds, is almost unshifted (4.606 vs. 4.608 ppm), whereas that of the core GlcNAc (3) experiences an upfield shift, from 4.561 to 4.552 ppm (FIG. 15E). That the second incoming fucose was bound to residue 6, however, was established by assignments of the other protons of GlcNAc residues 3 and 6 (FIGS. 16 and 17). Comparison of the chemical shifts with those of 26 revealed that while also the H-2 of GlcNAc 3 has shifted to somewhat higher field, the H-2, H-3 and H-4 of GlcNAc 6 experience a major downfield shift characteristic to α1-3 fucosylation (Ichikawa, Y. et al., *J. Am. Chem. Soc.* 114:9283–9298 (1992); Wormald, M. R. et al., *Biochem. Biophys. Res. Commun.* 180:1214–1221 (1991)). Knowing that the fucose in the monofucosylated material was bound to residue 5, it was also possible to assign the H-1 resonances of distal galactoses 7 and 8 in 28.

Example 9

Figure 13:
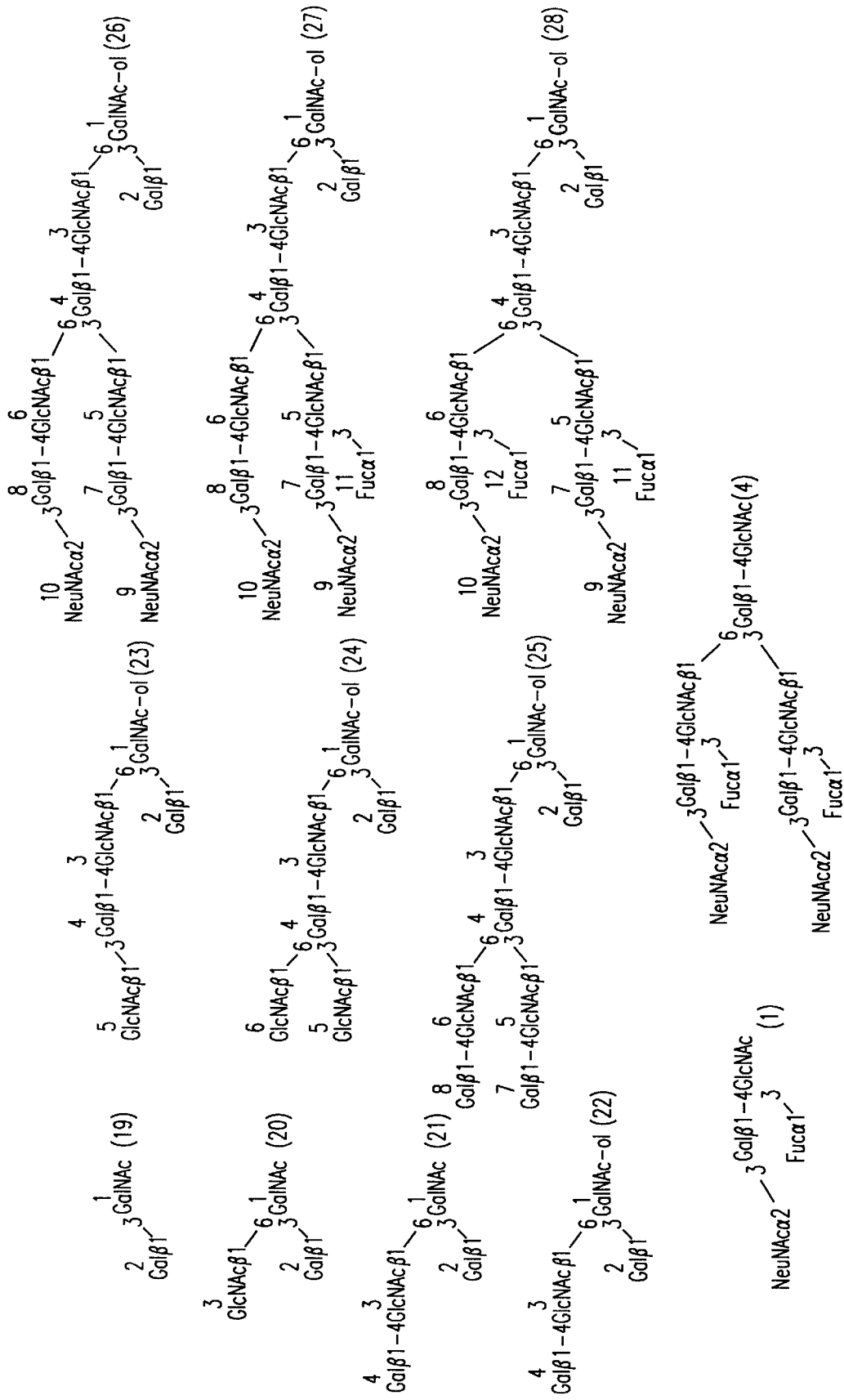
FIG. 13. Structures of the saccharides of the alditol series and denotation of the monosaccharide residues.

Alditol Inhibition of L-selectin-mediated Lymphocyte Adhesion (Bolded numbering corresponds to glycan structures in FIG. 13)

The O-glycosidic, branched oligosaccharides carrying zero, one or two terminal sialyl Le$^x$ motifs (glycans 26, 27, and 28 described in Example 8) were studied as an inhibitor of L-selectin-dependent lymphocyte adhesion to peritubular capillary endothelium of rejecting kidney allografts.

Ten to twelve weeks old rats of inbred WF (RT1$^v$) and DA (RT1$^a$) strains were used for the transplantations and lymphocyte adhesion assays as described in Example 1. The binding assays consisted of three experiments performed on separate days. Each experiment involved incubation of lymphocytes with three individual sections of the rejecting kidney in the presence of the saccharides at a given concentration; twenty separate fields were analyzed from all incubations.

The dodecasaccharide alditol 28 carrying two sialyl Le$^x$ determinants proved to be an efficient inhibitor of L-selectin dependent lymphocyte adhesion to the endothelium of rejecting rat kidney with $IC_{50}$ of 0.15 μM (FIG. 18). Concomitantly, the glycan 27, with only the 3-linked arm fucosylated, was a considerably weaker inhibitor, while the glycan 26, lacking both fucoses, was practically devoid of inhibitory activity. While these results indicate that net charge is not an explanation for increased affinity of the divalent sialyl Le$^x$ glycans for L-selectin, they also underline the importance of the fucose moiety in the oligosaccharide binding to selectins, as shown previously (Turunen, J. P. et al., *J. Exp. Med.* 182(4):1133–1141 (1995); Imai, Y. et al., *Glycobiology* 2:373–381 (1992); Mulligan, M. S. et al., *Nature* 364:149–151 (1993)). High affinity for E-selectin was previously demonstrated with divalent sialyl Le$^x$ glycans (DeFrees, S. A. et al., *J. Am. Chem. Soc.* 115:7549–7550 (1993); DeFrees, S. A. et al., *J. Am. Chem. Soc.* 117:66–79 (1995)) and with BSA conjugated sialyl Le$^x$ (Welply, J. K. et al., *Glycobiology* 4:259–265 (1994)), and for L-selectin with di- and tetravalent sialyl Le$^x$ constructs (Turunen, J. P. et al., *J. Exp. Med.* 182(4):1133–1141 (1995)).

The physical basis of the enhanced inhibitory potency of di- and multivalent oligosaccharides is still open. Selectins have been suggested to occur as multimers (Rosen & Bertozzi, *Curr. Opin. Cell Biol.* 6:663–673 (1994); Ushiyama, S. et al., *J. Biol. Chem.* 268:15229–15237 (1993)), which could explain the higher affinity of multivalent ligands. In glycan 28, however, the two sialyl Le$^x$ determinants are separated only by one monosaccharide moiety, making it unlikely that they could bind independently to different subunits of a multimeric protein if these are presented side-by-side on the cell surface. On the other hand, the B cell sialic acid-binding protein CD22, which binds specifically the trisaccharide NeuAca2-6GalB1-4GlcNAc, forms noncovalent oligomers, and has significantly higher affinity for an analogous divalent glycan than for the monovalent trisaccharide (Powell, L. D. et al., *J. Biol. Chem.* 270:7523–7532 (1995)).

In a recent work, DeFrees et al. studied inhibition of E-selectin mediated adhesion by positional isomers of two sialyl Le$^x$ groups linked by a galactose and found the 3,6-linked sialyl Le$^x$ dimer to be the most potent inhibitor (DeFrees, S. A. et al., *J. Am. Chem. Soc.* 117:66–79 (1995)). As pointed out by Graves et al. the x-ray structure of E-selectin does not rule out a dimeric form of sialyl Le$^x$ as a ligand, although the authors considered the increase in binding affinity to be small (Graves, B. J. et al., *Nature* 367:532–538 (1994)).

The inhibitory ability of the monovalent sialyl Le$^x$ undecamer 27, having fucose in the 3-linked arm, was the same as that of the monovalent sialyl Le$^x$ tetrasaccharide 1 (described in Example 2) at optimal concentrations (FIG. 18). This demonstrates that increasing the glycan size does not automatically increase the affinity for L-selectin. The inhibitory ability of a positional isomer of 27, having a monovalent 6-linked sialyl Le$^x$ group, is not known; in principle it is possible, that in the divalent glycan 28 mainly the 6-linked sialyl Le$^x$ group binds to the selectin and the increased affinity simply reflects the difference between the two branches.

Although it has been recently reported that the N-glycans of the E-selectin-ligand ESL-1 are required for the binding (Steegmaler, M. et al., *Nature* 373:615–620 (1995)), most biological ligands for L- and P-selectins are O-glycans (Schimizu & Shaw, *Nature* 366:630–631 (1993)). The glycoprotein ligands of L-selectin carry large numbers of closely spaced sialylated O-linked oligosaccharides (Lasky, L. A. et al., *Cell* 69:927–938 (1992); Baumhueter, S. et al., *Science* 262:436–438 (1993); Berg, E. L. et al., *Nature* 366:695–698 (1993); Norgard, K. E. et al., *J. Biol. Chem.* 268:12764–12774 (1993)), that present the distal sialyl Le$^x$ groups to the selectin in a manner similar to a branched poly-N-acetyllactosamine scaffold.

Here, the inhibitory ability of the dodecasaccharide alditol 28 has been compared with that of glycan 4 (described in Example 2), which lacks the reduced O-glycosidic core sequence (FIG. 18). As 28 appeared to be a little better inhibitor than 4, the core sequence may enhance the affinity for L-selectin. It is noteworthy that in 28, the NMR signals of the fucose and galactose residues of the two sialyl Le$^x$ groups have different chemical shifts, whereas the difference between the branches is very small, when the two sialyl Le$^x$ groups are bound to ethyl glycoside of galactose (DeFrees, S. A. et al., *J. Am. Chem. Soc.* 117:66–79 (1995)). This indicates, that the proximal part of 28 influences the properties of the distal sialyl Le$^x$ groups. Accordingly, the core structure of 28 does not have to be directly involved in the binding, while enhancing the affinity for L-selectin.

This is the first time that the inhibitory potency of complete sialyl Le$^x$-containing O-glycans has been tested in an L-selectin-dependent lymphocyte adhesion model. The inventors have established that the divalent sialyl Le$^x$ O-glycan is a significantly better inhibitor than the analogs lacking one or both of the fucoses.

Example 10

Treatment of a sLe$^x$ Positive Tumor Metastasis with sLEX

Carbohydrate-containing molecules have been implicated in many disease states, including auto-immune diseases, inflammatory conditions, peptic ulcers, infectious diseases and cancer. Indeed, changes in the surface carbohydrate molecules on human tumor cells has made it possible to identify human glycoprotein "cancer antigens" for many tumor types, including melanomas, gliomas, neuroblastomas and breast, pancreatic, lung, prostate and kidney cancers. One member of the lectin family of carbohydrate binding proteins has been strongly associated with both metastasis and shortened survival in breast cancer patients. The terminal sugar of the carbohydrate molecule to which the lectin binds has been identified as N-acetyl galactosamine. Moreover, the same N-acetyl galactosamine sugar has been found on several other tumor types, including prostate, stomach, and colorectal cancer cells, and has been associated with increased metastasis or reduced survival in each case. (Hughes, S., *Scrip*, April 1994, pp28–31) Other studies have shown that colon-carcinoma cell lines adhere to certain selectins via sialyl Lewis x and sialyl Lewis a oligosaccharides. (Majuri, M.-L. et al., *Int. J. Cancer* 63:551–559 (1995); Majuri, M.-L. et al., *Biochem. Biophys. Res. Comm.* 182(3):1376–1382 (1992)).

Accordingly, the synthetic multivalent sLe$^x$ containing polylactosamines of the present invention can be used to inhibit the metastasis of sLe$^x$ positive tumor cells. Briefly, a patient diagnosed with such a tumor is treated with a composition comprising a multivalent sLex, e.g. the tetravalent sLex 22-saccharide. The composition is in a pharmaceutically acceptable excipient at a sufficient dose to inhibit the metastasis of the sLe$^x$ positive tumor cells by blocking the binding of the tumor cells to natural sLe$^x$. An efficacious level of the composition is given in a regime such that a serum concentration is achieved in about the nanomolar to micromolar range until the condition is sufficiently ameliorated.

When administered to the patient, the composition is formulated in any manner which makes it suitable for oral, parenteral, nasal, enteric or rectal administration with a pharmaceutically acceptable excipient or vehicle, e.g., isotonic saline, in accordance with conventional pharmaceutical practice. The dosage level of the reagent will be sufficient to provide an anti-metastasis effect by the blocking of selectin, and especially L-selectin-mediated adhesion of the tumor cells in the patient.

By an "efficacious level" of a composition of the invention is meant a level at which some relief is afforded to the patient who is the recipient of the treatment.

The pharmaceutical compositions of the invention are administered in amounts sufficient to antagonize (fully or partially) the patient's native selectin, and especially L-selectin, binding to biological targets of such selectin in such patient, and specifically to sLe$^x$ positive tumor cells.

Amounts and regimens for the administration of selectin-binding carbohydrates and compositions of the invention can be determined readily by those with ordinary skill in the clinical art of treating cancer-related disorders. Generally, the dosage of the composition of the invention will vary depending upon considerations such as: type of synthetic carbohydrate employed; age; health; medical conditions being treated; kind of concurrent treatment, if any, frequency of treatment and the nature of the effect desired; extent of tissue darnage; gender; duration of the symptoms; and, counterindications, if any, and other variables to be adjusted by the individual physician. A desired dosage can be administered in one or more applications to obtain the desired results.

Example 11
Treatment of an Infection with sLEX

The use of sLe$^x$ as an anti-infective is based on the observation that oligosaccharides are present on the surface of all mammalian cells, and are used by bacteria, viruses, and other infectious micro-organisms to enter those cells. (Hughes, S., *Scrip*, April 1994, pp. 28–32) For example, human sialyl Lewis x antigen is highly expressed on the cell surface of Streptococcus gallolyticus, which is a cause of infective endocarditis in humans. (Hirota, K. et al., *Lancet* 347:760 (1996); Hirota, K. et al., *FEMS Immunol. & Med. Microbiol.* 12:159–164 (1995). Thus, flooding the body with one particular type of oligosaccharide is one possible therapeutic approach to particular infectious diseases. (Hughes, S., *Scrip*, April 1994, pp. 28–32). One advantage that oligosaccharides have over conventional anti-infectives is that they are effective in prevention, as well as treatment, of the infectious disease. In contrast, the use of antibiotics in the prophylaxis of infection may lead to the development of resistance. Moreover, since oligosaccharides do not kill the bacteria, but instead merely inhibit their binding to human tissue, they will not provide any selection pressure for the growth of resistant organisms. (Hughes, S., *Scrip*, April 1994, pp. 28–32).

The synthetic multivalent sLe$^x$ containing polylactosamines of the present invention may be used to treat or prevent infectious diseases. Briefly, a patient diagnosed with such an infection is treated with a composition comprising a multivalent sLex, e.g., the tetravalent sLex 22-saccharide. The composition is in a pharmaceutically acceptable excipient at a sufficient dose to block infectious microorganisms, e.g. bacteria, from binding to the correspondent oligosaccharides on the corresponding, e.g. endothelial, cell surface. The composition is given in a regime such that a serum concentration is achieved in about the nanomolar to micromolar range until the condition is sufficiently ameliorated.

When administered to the patient, the composition is formulated in any manner which makes it suitable for oral, parenteral, nasal, enteric or rectal administration with a pharmaceutically acceptable excipient or vehicle e.g., isotonic saline, in accordance with conventional pharmaceutical practice. The dosage level of the reagent will be sufficient to provide an anti-infective effect by the blocking of selectin, and especially L-selectin-mediated adhesion events in the patient.

By an "efficacious level" of a composition of the invention is meant a level at which some relief is afforded to the patient who is the recipient of the treatment.

Accordingly, the pharmaceutical compositions of the invention are administered in amounts sufficient to antagonize (fully or partially) the patient's native selectin, and especially L-selectin, binding to biological targets of such selectin in such patient, and specifically to endothelial cells.

Amounts and regimens for the administration of selectin-binding carbohydrates and compositions of the invention can be determined readily by those with ordinary skill in the clinical art of treating infectious diseases. Generally, the dosage of the composition of the invention will vary depending upon considerations such as: type of synthetic carbohydrate employed; age; health; medical conditions being treated; kind of concurrent treatment, if any, frequency of treatment and the nature of the effect desired; extent of tissue damage; gender; duration of the symptoms; and, counterindications, if any, and other variables to be adjusted by the individual physician. A desired dosage can be administered in one or more applications to obtain the desired results.

All references mentioned herein are incorporated by reference in the disclosure.

Although the foregoing refers to particular preferred embodiments, it will be understood that the present invention is not so limited. It will occur to those ordinarily skilled in the art that various modifications may be made to the disclosed embodiments and that such modifications are intended to be within the scope of the present invention.

What is claimed is:

1. A synthetic sLe$^x$ oligosaccharide, essentially free of contaminants, having a polylactosamine backbone (LacNAc)$_n$, wherein n≧1 and having interresidual links that are β1-3' and/or β1-6', to which at least two NeuNAcα2-3Galβ1-4(Fuc1-3) GlcNAc epitopes are linked by β1-3' and/or β1-6' bonds.

2. The synthetic sLe$^x$ oligosaccharide of claim 1, wherein said polylactosamine backbone is branched.

3. The synthetic sLe$^x$ oligosaccharide of claim 1, wherein said polylactosamine backbone is linear.

4. The synthetic sLe$^x$ oligosaccharide of claim 1, wherein said oligosaccharide is a tetravalent 22-meric oligosaccharide.

5. The synthetic sLe$^x$ oligosaccharide of claim 2, wherein said sLe$^x$ oligosaccharide has an O-glycosidic core containing a Galβ1-3GalNAc-ol sequence, and wherein said GlaNAcα2-3Galβ1-4(Fuc1-3)epitopes are bonded by β1,3'-, β1,6'-, or β1,6 linkage.

6. The synthetic sLe$^x$ oligosaccharide of claim 5, wherein said sLe$^x$ is divalent.

7. The synthetic sLe$^x$ oligosaccharide of claim 6, wherein said oligosaccharide is a dodecameric O-glycosidic core 2 type oligosaccharide alditol with a branched polylactosamine backbone carrying two distal α2,3' sialylated and α1,3 fucosylated N-acetyllactosamine groups.

8. A pharmaceutically acceptable composition comprising the synthetic sLe$^x$ oligosaccharide of claim 1 in combination with at least one pharmaceutically acceptable excipient, carrier, solvent or vehicle.

9. A pharmaceutically acceptable composition comprising the synthetic sLe$^x$ oligosaccharide of claim 5 in combination with at least one pharmaceutically acceptable excipient, carrier, solvent or vehicle.

10. A method of ameliorating a condition in a patient diagnosed with said condition, wherein said condition is an inflammatory condition or a cancer, and wherein said inflammatory condition is selected from the group consisting of tissue rejection, organ rejection, arthritis, a chronic inflammatory disease, reperfusion injury, septic shock, traumatic shock, asthma, an infection, a dermatosis, inflammatory bowel disease, and an autoimmune disease, said method comprising administration of the composition of claim 8 to said patient.

11. A method of protecting against rejection of a transplanted tissue or organ, said method comprising administering the composition of claim 8 to a patient who received a transplant.

12. A method for blocking deleterious migration of leukocytes in an abnormal inflammatory condition in a patient comprising administration of the composition of claim 8 to said patient.

13. The method of claim 10, wherein said condition is cancer.

14. The method of claim 13, wherein said cancer comprises metastasis of sLe$^x$ positive tumor cells.

15. The method of claim 10, wherein said condition is an infection.

16. The method of claim 10, wherein said patient is an animal.

17. The method of claim 16, wherein said animal is human.

18. A method for synthesizing sLe$^x$ oligosaccharides having a branched polylactosamine backbone which utilizes N-acetyllactosamine, the hexasaccharide Galβ1-4GlcNAcβ1-6(Galβ1-4GlcNAcβ1-3)Galβ1-4GalNAc, and the tetradecasaccharide Galβ1-3GlcNAcβ1-6(Galβ1-4GlcNAcβ1-3)Galβ1-4GlcNAcβ1-6[Galβ1-4GlcNAcβ1-6(GalB1-4GlcNAcβ1-3)Galβ1-4GlcNAcβ1-3]Galβ1-4GlcNAc, as acceptors for mono-, di-, and tetravalent sLe$^x$ saccharides, respectively, said method comprising:

(i) incubating said acceptors with CMP-NeuNAc and α2,3 sialyltransferase from human placenta to yield isolated, fully α2,3 sialylated saccharides; and (ii) incubating the product of step (i) with GDP-Fucose and a partially purified preparation of human milk α1,3 fucosyltransferase to yield isolated, fully sialylated, α1,3 fucosylated saccharides.

19. A method for synthesizing a tetravalent sLe$^x$ 22-meric oligosaccharide having a linear polylactosamine backbone from an octameric polylactosamine having the structure LacNAcβ1-3'(GlcNAcβ1-6 ')LacNAcβ1-3'(GlcNAcβ1-6') LacNAc, where LacNAc is the disaccharide Galβ1-4GlcNAc, said method comprising the steps of:

(i) elongating said octameric polylactosamine by treatment with β1,3-GlcNac transferase to produce an isolated saccharide mixture;

(ii) treating said isolated saccharide mixture from step (i) with β1,6-GlcNac transferase from hog gastric mucosa;

(iii) treating the saccharide product from (ii) with β1,4 galactosyl transferase to yield a branched array of seven LacNac units;

(iv) sialylating the oligosaccharide product from step (iii); and (v) fucosylating the oligosaccharide product from step (iv) to yield the tetravalent sLe$^x$ saccharide.

20. A synthetic sLe$^x$ oligosaccharide produced by the method of either claim 18 or claim 19.

21. A pharmaceutical composition comprising the synthetic sLe$^x$ oligosaccharide of claim 20 in combination with at least one pharmaceutically acceptable excipient, carrier, solvent or vehicle.

22. A method of ameliorating a condition in a patient diagnosed with said condition, wherein said condition is an inflammatory condition or a cancer, and wherein said inflammatory condition is selected from the group consisting of tissue rejection, organ rejection, arthritis, a chronic inflammatory disease, reperfusion injury, septic shock, traumatic shock, asthma, an infection, a dermatosis, inflammatory bowel disease, and an autoimmune disease, said method comprising administration of the composition of claim 9 to said patient.

23. A method of protecting against rejection of a transplanted tissue or organ, said method comprising administering the composition of claim 9 to a patient who received a transplant.

24. A method for blocking deleterious migration of leukocytes in an abnormal inflammatory condition in a patient comprising administration of the composition of claim 9 to said patient.

25. The method of claim 22, wherein said condition is cancer.

26. The method of claim 25, wherein said cancer comprises metastasis of sLe$^x$ positive tumor cells.

27. The method of claim 22, wherein said condition is an infection.

28. The method of claim 22, wherein said patient is an animal.

29. The method of claim 28, wherein said animal is human.

30. The synthetic sLe$^x$ oligosaccharide of claim 1, wherein said oligosaccharide is divalent.

31. The synthetic sLe$^x$ oligosaccharide of claim 30 having the formula:

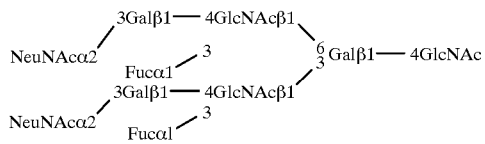

wherein

Gal is galactose;

Fuc is fucose;

GlcNAc is N-acetylglucosamine; and

NeuNAc is sialic acid.

32. The synthetic sLe$^x$ oligosaccharide of claim 4 having the formula:

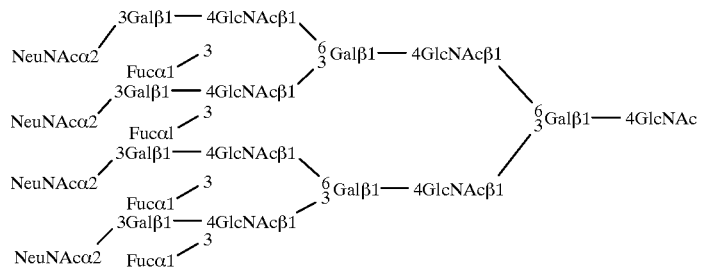

wherein

Gal is galactose;

Fuc is fucose;

GlcNAc is N-acetylglucosamine; and

NeuNAc is sialic acid.

33. The synthetic sLe$^x$ oligosaccharide of claim 4 having the formula:

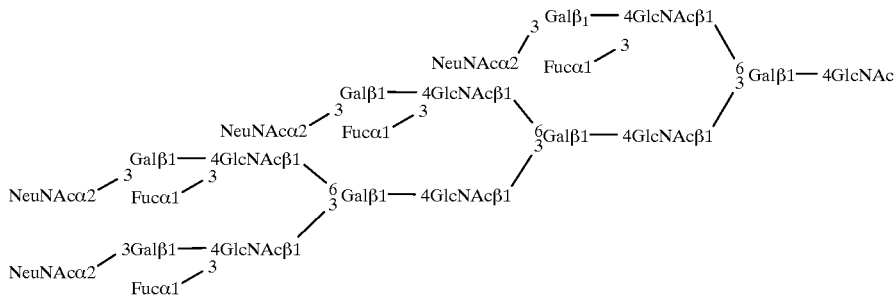

wherein

Gal is galactose;
Fuc is fucose;
GlcNAc is N-acetylglucosamine; and
NeuNAc is sialic acid.

34. The synthetic sLe$^x$ oligosaccharide of claim 7 having the formula:

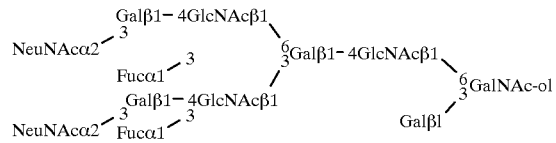

wherein

Gal is galactose;
Fuc is fucose;
GlcNAc is N-acetylglucosamine; and
NeuNAc is sialic acid.

35. The method of claim 10, wherein said chronic inflammatory disease is psoriasis or rheumatoid arthritis.

36. The method of claim 22, wherein said chronic inflammatory disease is psoriasisor rheumatoid arthritis.

* * * * *

UNITED STATES PATENT AND TRADEMARK OFFICE
CERTIFICATE OF CORRECTION

PATENT NO. : 5,965,544
DATED : October 12, 1999
INVENTOR(S) : Renkonen et al.

It is certified that error appears in the above-identified patent and that said Letters Patent is hereby corrected as shown below:

Column 6,
Line 19, delete "FIG. 9" and insert therefor --FIG. 9 (panels A-C).--.
Line 50, delete "15E" and insert therefor --15E-15H--.
Line 66, delete "(panels A-E)" and insert therefor --(panels A-H)--.

Column 7,
Line 1, delete "(E)" and insert therefor --(E-H)--.
Line 4, delete "FIG. 16" and insert therefor --FIG. 16 (panels A-B).--.
Line 47, delete "9" and insert therefor --9A-C--;
line 49, delete "9" and insert therefor --9A-C--.

Column 26,
Lines 29 and 30, delete "9" and insert therefor --9A-C--.

Column 33,
Line 15, delete "15E" and insert therefor --15E-H--.
Line 37, delete "15E" and insert therefor --15E-H--.

Column 34,
Line 26, delete "15E" and insert thereof --15E-H--.
Line 29, delete "16" and insert therefor --16A-B--.

UNITED STATES PATENT AND TRADEMARK OFFICE
CERTIFICATE OF CORRECTION

PATENT NO. : 5,965,544
DATED : October 12, 1999
INVENTOR(S) : Renkonen et al.

It is certified that error appears in the above-identified patent and that said Letters Patent is hereby corrected as shown below:

Column 38,
Line 33, claim 5,
Please delete "G1aNAc$\alpha$2-3Gal$\beta$1-4(Fuc1-3)" and insert therein
--NeuNAc$\alpha$2-3Gal$\beta$1-4(Fuc1-3)G1cNAc--.

Signed and Sealed this

Third Day of July, 2001

*Attest:*

NICHOLAS P. GODICI
*Attesting Officer*  *Acting Director of the United States Patent and Trademark Office*